United States Patent
Holmes et al.

(10) Patent No.: US 7,648,452 B2
(45) Date of Patent: Jan. 19, 2010

(54) APPARATUS FOR BLOOD COMPONENT SEPARATION

(75) Inventors: Brian M. Holmes, Lakewood, CO (US); Johan-Petter Hagström, Hägersten (SE); Per-Olov Lundberg, Karlskoga (SE); Geert Van Waeg, Brussels (BE); Peter Nordgren, Stockholm (SE)

(73) Assignee: CardianBCT, Inc., Lakewood, CO (US)

( * ) Notice: Subject to any disclaimer, the term of this patent is extended or adjusted under 35 U.S.C. 154(b) by 33 days.

(21) Appl. No.: 12/167,441

(22) Filed: Jul. 3, 2008

(65) Prior Publication Data

US 2008/0314822 A1 Dec. 25, 2008

Related U.S. Application Data

(60) Continuation of application No. 11/611,567, filed on Dec. 15, 2006, now Pat. No. 7,413,665, and a continuation of application No. 11/611,682, filed on Dec. 15, 2006, now Pat. No. 7,396,451, said application No. 11/611,567 is a division of application No. 10/648,559, filed on Aug. 25, 2003, now Pat. No. 7,166,217, said application No. 11/611,682 is a division of application No. 10/648,559, filed as application No. PCT/US03/11764 on Apr. 16, 2003, now Pat. No. 7,166,217.

(60) Provisional application No. 60/373,083, filed on Apr. 16, 2002, provisional application No. 60/405,667, filed on Aug. 23, 2002, provisional application No. 60/405,474, filed on Aug. 23, 2002.

(51) Int. Cl.
*B04B 7/12* (2006.01)

(52) U.S. Cl. .................. 494/45; 210/380.1; 210/782; 494/69; 604/410

(58) Field of Classification Search .................. 210/782, 210/380.1; 494/45, 69; 604/410
See application file for complete search history.

(56) References Cited

U.S. PATENT DOCUMENTS

| | | | |
|---|---|---|---|
| 3,297,244 A | 1/1967 | Hein | |
| 3,326,458 A | 6/1967 | Meryman et al | |
| 3,679,128 A | 7/1972 | Unger et al | |
| 3,708,110 A | 1/1973 | Unger et al. | |
| 3,724,747 A | 4/1973 | Unger et al. | |
| 3,737,096 A | 6/1973 | Jones et al. | |
| 3,858,796 A | 1/1975 | Unger et al. | |
| 3,987,961 A | 10/1976 | Sinn et al. | |

(Continued)

FOREIGN PATENT DOCUMENTS

EP 0499891 8/1992

(Continued)

OTHER PUBLICATIONS

International Search Report for PCT/US03/26768, mailed Apr. 1, 2004.

*Primary Examiner*—David A Reifsnyder
(74) *Attorney, Agent, or Firm*—Edna M. O'Connor; John R. Merkling; Laura B. Arciniegas

(57) ABSTRACT

A device for loading a set of bags into the rotor of a centrifuge including a loading container having an annular rim extending outwardly such that the annular rim rests on the turn table of the rotor.

5 Claims, 38 Drawing Sheets

U.S. PATENT DOCUMENTS

| | | |
|---|---|---|
| 4,389,207 A | 6/1983 | Bacehowski et al. |
| 4,405,079 A | 9/1983 | Schoendorfer |
| 4,421,503 A | 12/1983 | Latham, Jr. et al. |
| 4,482,342 A | 11/1984 | Lueptow et al. |
| 4,720,284 A | 1/1988 | McCarty |
| 4,850,995 A | 7/1989 | Tie et al. |
| 4,990,132 A | 2/1991 | Unger et al. |
| 5,114,396 A | 5/1992 | Unger et al. |
| 5,427,695 A | 6/1995 | Brown |
| 5,632,906 A | 5/1997 | Ishida et al. |
| 5,723,050 A | 3/1998 | Unger et al. |
| 5,738,644 A | 4/1998 | Holmes et al. |
| 5,874,208 A | 2/1999 | Unger |
| 5,964,724 A | 10/1999 | Rivera et al. |
| 6,261,217 B1 | 7/2001 | Unger et al. |
| 6,296,602 B1 | 10/2001 | Headley |
| 6,315,706 B1 | 11/2001 | Unger et al. |
| 6,348,031 B1 | 2/2002 | Unger et al. |
| 6,656,105 B2 | 12/2003 | Hogberg et al. |
| 2002/0119880 A1 | 8/2002 | Hogberg et al. |
| 2004/0026341 A1 | 2/2004 | Hogberg et al. |

FOREIGN PATENT DOCUMENTS

| | | |
|---|---|---|
| EP | 0771569 | 5/1997 |
| WO | WO 92/00145 | 1/1992 |
| WO | WO 01/02037 | 1/2001 |
| WO | WO 01/97943 | 12/2001 |
| WO | WO 03/089027 | 10/2003 |
| WO | WO 2004/018021 | 3/2004 |

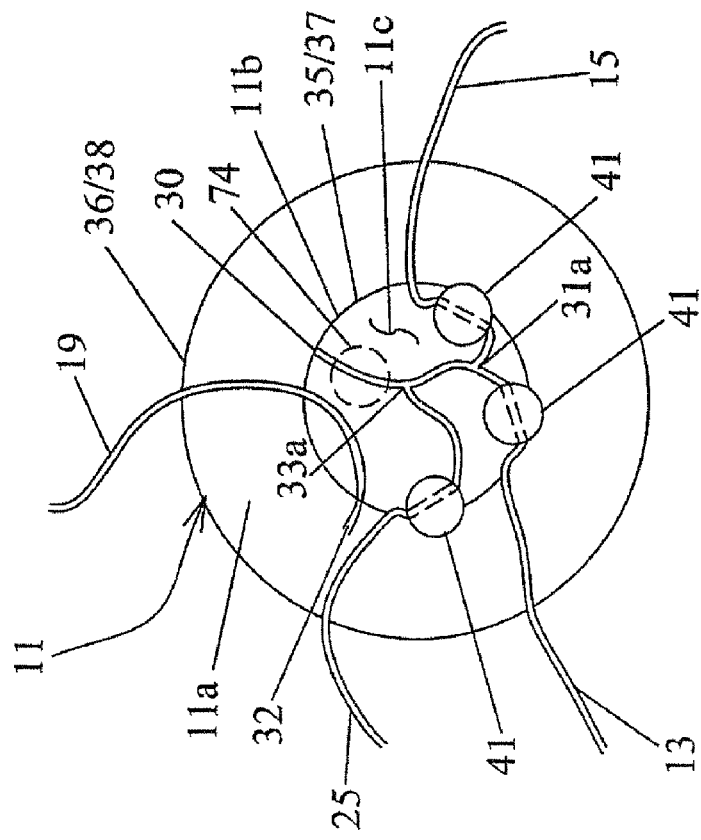
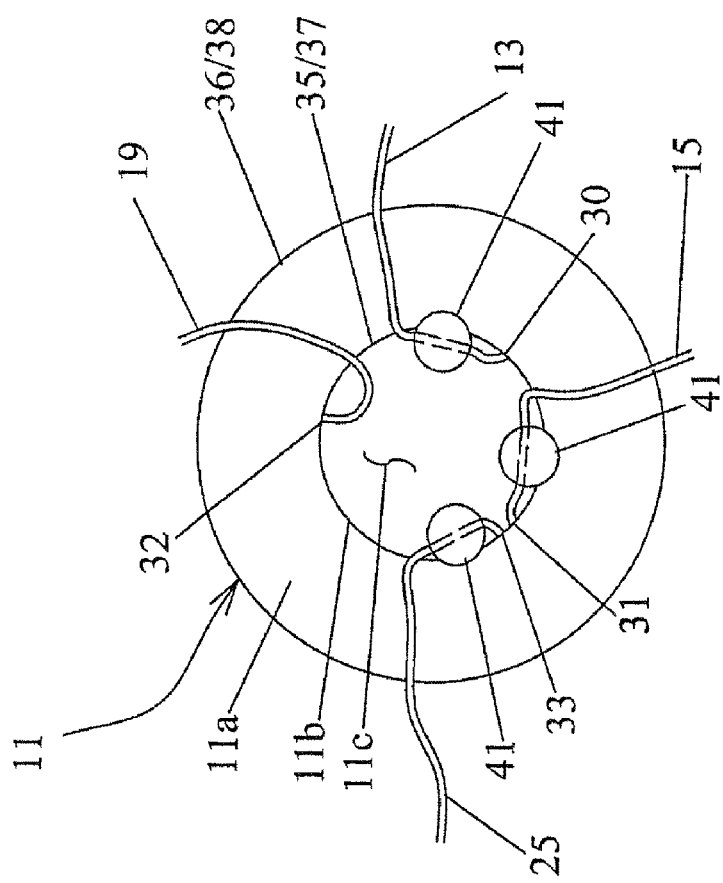
Fig. 4B
Fig. 4A

APPARATUS FOR BLOOD COMPONENT SEPARATION

PRIORITY CLAIM

This application is a continuation of U.S. patent application Ser. No. 11/611,567, filed Dec. 15, 2006, now U.S. Pat. No. 7,413,665 and U.S. patent application Ser. No. 11/611,682, filed Dec. 15, 2006, now U.S. Pat. No. 7,396,451 both of which are divisionals of U.S. patent application Ser. No. 10/648,559 filed Aug. 25, 2003, now U.S. Pat. No. 7,166,217 which is the national phase of International Patent Application No. PCT/US03/11764 filed Apr. 16, 2003, which claims the benefit under 35 USC § 119(e) of U.S. Provisional Application Nos. 60/373,083 filed Apr. 16, 2002 and 60/405,667 filed Aug. 23, 2002.

Application Ser. No. 10/648,559 also claims the benefit of Provisional Application No.: 60/405,474, filed Aug. 23, 2002.

Application Ser. No. 10/648,559 also claims the benefit of U.S. patent application Ser. No. 10/414,475 filed Apr. 16, 2003, now U.S. Pat. No.: 7,279,107.

Application Ser. No.: 10/414,475 also claims the benefit under 35 USC §119(e) of U.S. Provisional Application No. 60/405,474 filed Aug. 23, 2002.

BACKGROUND OF THE INVENTION

1. Field of the Invention

The present invention relates to fluid separation systems and/or methods. Particular examples include separation systems and/or methods for blood component processing and/or preparation. Such separation systems and/or methods may take place in a centrifuge of a type, which may generally have a rotor with an annular separation compartment and a substantially open central compartment that may be arranged generally concentrically about the axis of rotation of the rotor.

2. Description of the Related Art

Today's blood centers face formidable challenges. Doctors, hospitals and blood banks demand greater quantities and more specific and higher quality blood component products for the patients they serve. An optimal general solution is to maximize the quantity and the quality of blood components processed from each collection.

A review of conventional blood processing reveals that in the preparation of blood component products, blood is often separated into one or more components such as plasma, a buffy coat and/or platelets and red blood cells by centrifugation. Conventional so-called manual and apheresis (automated separation) processes are both used. However, since the present invention is generally directed to processing manually collected discrete portions or units of whole blood, and since apheresis has taken on the general meaning that it avoids this initial step of manual collection of one or more discrete units of whole blood, conventional apheresis as a general process will not be discussed further here.

In conventional manual collection processes, a sterile set of interconnected flexible containers or bags is typically used. The presently most common mode of operation is to use a sterile set of interconnected substantially rectangular blood bags, one bag being the initial collection container and often also the separation container, into which whole blood is collected. The other interconnected bags are then the resulting processed blood component containers, to which the separated components are transferred after processing/separation. The entire set is typically centrifuged in a swing-out centrifuge bucket or cup and, during centrifugation, the separating and separated blood components form layers in the separation container according to the respective increasing specific weights. A plasma layer, a buffy coat layer and a layer of red blood cells are thus formed, and these usually remain stratified even after centrifugation is complete. Then in this conventional process, the set of bags is typically manually removed from the centrifuge and moved to a pressing or expresser device for expressing or pressing out the plasma layer and/or the red blood cell layer to associated interconnected component containers. This would then usually leave the buffy coat layer in the original bag or, the buffy coat could also be expressed to its own interconnected container or otherwise to a pooling container. Great care must be used during the manual handling of the bags when the layers are separated/stratified in this manner, yet still in contact with each other in the original separation bag, because such manual handling often results in some undesirable re-mixing of the components which would then result in a lower quality product or an inefficiency in the overall process by necessitating a re-centrifugation of that unit of blood.

Moreover, it is generally inevitable in conventional centrifugation and expression operations that a certain amount of interfacing components will remain incompletely separated, at least in so far as being incapable of complete separation and pure collection after a single centrifugal process, as for example when a quantity of red blood cells will remain with the buffy coat after expression. Thus, conventional whole blood to buffy coat to platelet processing usually includes further processing steps after the initial whole blood separation process. This often includes at least four post-donation, post-initial separation processes/steps; namely; pooling of a plurality of buffy coats, then centrifugation of these pooled buffy coats, then expressing of the plasma and/or platelets therefrom and usually also a leukoreduction step. These tasks are generally carried out with manual, labor-intensive steps and blood centers are challenged with time-consuming, error-prone manual operations for such buffy coat processing, and these processes with their associated risks are in addition to the initial manual processing problems such as the inadvertent re-mixing as suggested above.

Still further, successful modern blood component therapy is dependent on high purity blood component fractions, i.e. these components should be contaminated as little as possible by each other. Particularly troublesome is contamination of any component product by the intermediate buffy coat fraction which contains the potentially contaminated white blood cells that would or could in turn contaminate the other interfacing component product or products. Controlled expression of the various fractions from the separation container to thereby reduce any re-mixing of the buffy coat with any other product has thus presented a fairly important, if not critical operation with respect to the achievement of pure or substantially pure end component products.

Thus, different techniques of achieving high purity separated fractions have been contemplated. Some suggestions have involved the use of a centrifuge rotor having an annular separation area for holding a generally annularly or ring-shaped separation container. Such a centrifuge may have provided for subjecting such a separation container to compression forces in the separation compartment of the rotor during centrifugal rotation to force fluids disposed therein to flow generally out of the ring container, and thus one or more of the separated layers may then have been pressed out and toward a central compartment of the rotor and into one or more secondary containers disposed therein even while they remain subjected to the prevailing centrifugal force field.

Even so, success with such ring-shaped separation containers and centrally disposed secondary containers has heretofore been limited.

SUMMARY OF THE INVENTION

The new automated systems and/or methods of the present invention provide efficient, reliable, cost-effective solutions to these and other as yet unnamed challenges. The present invention provides automated component processing of manually collected whole blood. Such whole blood can be processed into two (2) and/or three (3) component (hereafter 2/3 components) products, inter alia. Specifically, whole blood may typically be separated into two component products; namely, red blood cells (also known as RBCs) and plasma in what may be known as a two (2) component or RBC/plasma process, and/or separated into three components; namely RBCs, plasma and platelets (or buffy coat) in a three (3) component RBC/platelet/plasma (or RBC/buffy coat/plasma) process. In a particular set of embodiments, a charge or unit of whole blood can be supplied to a system of the present invention, which can then substantially automatically process that whole blood into the two or three components, and have those two or three components moved to discrete component storage containers, fully processed (or nearly fully processed; e.g. leukoreduction may be online or offline), and thence removable from the system of the present invention immediately ready for storage or use in transfusion/infusion.

Various processes or methods may be used to accomplish these goals. For example, a process may involve a substantially constant spin rate with a consequent removal of two (or three) components from the continually spinning ring bag. Or, in one alternative, a first hard spin may be used in conjunction with a subsequent softer spin to provide a desirable three blood component separation process, with three resultant blood component products. Such a process may thus also automate a platelet production process in and/or during a single overall procedure and avoid separate buffy coat processing. More details of these and other alternatives will be set forth hereinbelow.

The present invention is flexible to meet the needs of a blood bank or center, with the potential to accommodate future changes in clinical, regulatory or other requirements. Protocols can also be added or changed to create a flexible platform for blood component production. Efficiency may be provided to the user/operator through use of a single system for the production of either two or three end component products. The present invention also allows for integration of multiple processes, combining the conventionally separate processes of pooling, centrifugation, expression, leukoreduction and sealing of separated blood component products now all in one machine/instrument during one overall automated process. The present invention also provides the advantage of providing an automated hands-off solution that is therefore simpler and less time-consuming for the operator to use. Moreover, safety is also provided whereby the present invention may be disposed as a closed system safe for the operators and ultimately also for the patients receiving the high quality end products produced hereby. Quality may be highly controlled by the automated systems and methods hereof so that the highest quality standards can be achieved and the highest rates of consistency in component processing can be delivered which lead to consistent high quality outcomes. Such quality outcomes may include achieving greater yields than conventional manual preparation methods. The present invention may further provide control in using one or more eyes or optical sensor(s) in the process and such integral monitoring provides accurate, automated control of any or all processes.

An aspect of the present invention is to provide a method and/or system that solves the above-mentioned problems and affords effective and timely preparation of blood components of high purity. This may be achieved using a centrifuge and a set of containers as parts of the system adapted each to the other. The set of containers may preferably include a substantially flat and/or conical, round or ring-like separation container. A set of containers according to the invention may further include at least one component container connected by a tube to an outlet from the ring-like separation container. One or more of the container(s) in the set of containers may be made of one or more flexible materials and/or thus be like bags used in otherwise conventional blood processing. The separation container or bag set may further include various features such as tubing line positioning which may be adapted for operative relationship(s) with one or more corresponding clamp or pinch valves optionally mounted in and/or on the separation rotor of the centrifuge.

A loading device may also be included in one or more embodiments for receiving and holding the container or bag set and assist or improve operator handling during insertion and/or loading of the container or bag set in, as well as providing better maneuverability of the bag set outside, the centrifuge system. Such a loading device may be single use or may be reused and thus applied to use with a new separation container and bag set after transfer or removal therefrom of the previously finished component products; plasma, red blood cells and/or platelets (or buffy coats).

In use, the method and/or system may involve control over the centrifuge rotational characteristics, such as speed, as well as control over the flows in and/or out of respective containers using, for example, one or more optical or pressure sensors and controlled valves. Moreover, the transfer of the separated component products, e.g., plasma, platelets (or buffy coat) and/or red blood cells to their respective secondary component containers can be carried out inside the centrifuge system, either after, and/or during the centrifuging separation process, i.e., during continued centrifuge rotation but preferably after a certain minimal separation has been achieved. Note, in most embodiments herein, the displacement of any separated components to an associated container may be made to preferably take place during continued centrifugal rotation while the fluid layers thus remain subjected to the centrifugal forces. In this type of process as described generally herein, one charge or unit of blood will usually (though not necessarily) be processed in each centrifugation, which means that a short process time in the centrifuge would be highly desirable in routine preparation of blood components therefrom.

As an example of one alternative process herein, a charge of whole blood disposed within a round, annular separation container or bag in a centrifuge may be spun at a first rotational speed, e.g., 3200 rpm's with no flow occurring in or out of the round bag. Then, after a period of centrifugal separation at this first rotational speed, yet while the rotation is maintained at this first speed, a selected valve may be opened by the system and a flow of a first separated component such as, for example, plasma, may be started out of the round annular container through a connecting tube to a first component container which may be residing in a central compartment of the centrifuge. A substantial amount, though perhaps not all of the first component will be moved out of the separation container to the product container.

Then, according to an embodiment of the present invention, one or more selected valves may be opened and closed to consecutively provide for expressing a second component product, e.g., a buffy coat or the red blood cells (with the buffy coat therein or filtered or to be filtered therefrom) in a two component process, to a second container, and if in three component mode, then the third component may be moved to a third component container. Alternatively, according to another embodiment of the present invention, after the expression of the first component product, a second, slower rotational speed may be imparted on the centrifuge rotor and the annular separation bag. This slower speed may then coact with the momentum of the remaining second and third component products to strip the previously settled second component, such as a buffy coat/platelet product, off the interface with the third component layer, for example a red blood cell layer, to re-suspend the second component, e.g., platelets, in a remainder portion of the first component, e.g., plasma. Coriolis forces may be involved (though not necessarily) in this process of stripping and re-suspending the second component. Then, after a period of second component or platelet re-suspension (and third component, e.g., RBC, re-settling out of suspension, if any), but also during continued rotation, the suspended second product, e.g., platelet fluid suspension, may be pressed out of the separation container into a second product, e.g., platelet product container. After this, the third product remainder, e.g., the red blood cell (RBC) remainder, may be moved or expressed into a separate third product, RBC, product container. The end product containers may then be valved closed and/or sealed off by the system during or after centrifugation, and then, upon stoppage of the centrifugal rotation, the discrete plasma, platelet and RBC product containers may be separately removed from the central portion of the centrifugal chamber. These end products are thus simply producible in a high quality, repeatable, automated fashion and are then ready for storage or direct transfusion/infusion or are ready for other use or processing.

Leukoreduction of these products may also be performed. In one embodiment, the whole blood may be leukoreduced prior to centrifugal separation using a whole blood leukoreduction filter. A platelet-sparing whole blood leukoreduction filter may be used to allow for a greater recovery of platelets in a platelet product. Alternatively, a platelet-sacrificing filter could be used, with a typical goal of then only obtaining two end blood component products, e.g., plasma and RBCs. As a further alternative, leukoreduction filtration may be achieved after separation either in a substantially conventional manner after removal of the end-product containers from the centrifugal system, or filtration may occur in the centrifugal system during the expression of respective products, e.g., platelets and/or RBCs (and/or plasma), from the centrifugal separation container. In such a case one or two (or more) leukoreduction filters may be used. For example, a single platelet and RBC sparing in-line leukoreduction filter may be disposed in the flow path from the separation container to the end product containers. Platelets and/or RBCs (and possibly also plasma) may be made to flow sequentially through such a single filter during the expression process. Or, if two (or more) filters may be used, these may each be respectively disposed in separate exit flow paths from the separation container to the respective end product containers. Thus, discrete types of filters may be used for the respective products, e.g., platelets and RBCs (and/or plasma). As a result, the present invention may thus provide highly pure plasma, red blood cells and/or platelets or buffy coat components, leukoreduced or otherwise.

In a further set of alternatives, if a buffy coat product is a desired (end or intermediate) product, the buffy coat layer may be removed as mentioned above, sequentially after the plasma and before the RBCs in a standard spin process. Or, the buffy coat may be separated during a first spin rate which may not be as hard (for example 1500 or 2000 rpm's) as that described for the RBC/platelet/plasma process, and thus the buffy coat may favorably be affected to only a small overall extent and may be mixed to a minimum extent with the neighboring layers during the displacement of those other components to the central section of the separation rotor. The buffy coat layer can then be displaced radially inwardly toward the center of the rotor uniformly from all directions (as the other products would also be) and may (but need not) be expressed through an outlet. As an alternative, the buffy coat can remain residing in the ring bag after expression of separated plasma and/or RBCs, and then the buffy coat can be pooled into a subsequent separation container from the ring bag itself. In such a case, RBCs would preferably have been removed during the centrifugal process using for example either a port in the outer circumference of the ring bag, or an elongated port structure disposed or defined in the ring bag extending from the inner circumference outwardly toward the outer circumference.

Several different embodiments of the invention will now be described in more detail with reference to the accompanying drawing figures in which like elements are identified with like reference numerals throughout the several views.

BRIEF DESCRIPTION OF THE DRAWINGS

In the drawings:

FIG. 4 includes sub-part FIGS. 4A and 4B which are schematic, substantially plan views of alternative ring-like separation containers according to the present invention;

DETAILED DESCRIPTION OF THE PREFERRED EMBODIMENTS

The present invention is generally intended for separation of a fluid into fractional or component parts thereof, and may be particularly useful in the separation of whole blood into fractions, also known as blood components, or simply, components. Separation can be performed to obtain either two component products; for an example from blood, these two components may typically be plasma and red blood cells (RBCs), or to obtain three (or more) component products; for another example from blood, typical three component separations will include plasma, RBCs and either a buffy coat or a platelet product. Note, even though blood, and particularly whole blood, is used as the principal example of the fluid being separated and/or processed in the present invention, the principles hereof are also suited for separation and/or processing of other composite fluids or cell suspensions into two or three or more fractions particularly when it may be preferred for such a process to be carried out in a closed, automated system. In other words, the present systems and methods may be desirable particularly when the components are desired to be separated and then isolated or isolatable in separate containers without opening the system. Further, these systems and methods are particularly useful when maintained sterility is preferred, as will often be the preference with cell compositions or other bodily or biological fluids. Such fluids are desirably maintained in sterile condition as for example when they may be subject to rigorous or sensitive diagnostic testing or may be destined for future infusion or transfusion to a patient.

Figure 1A:
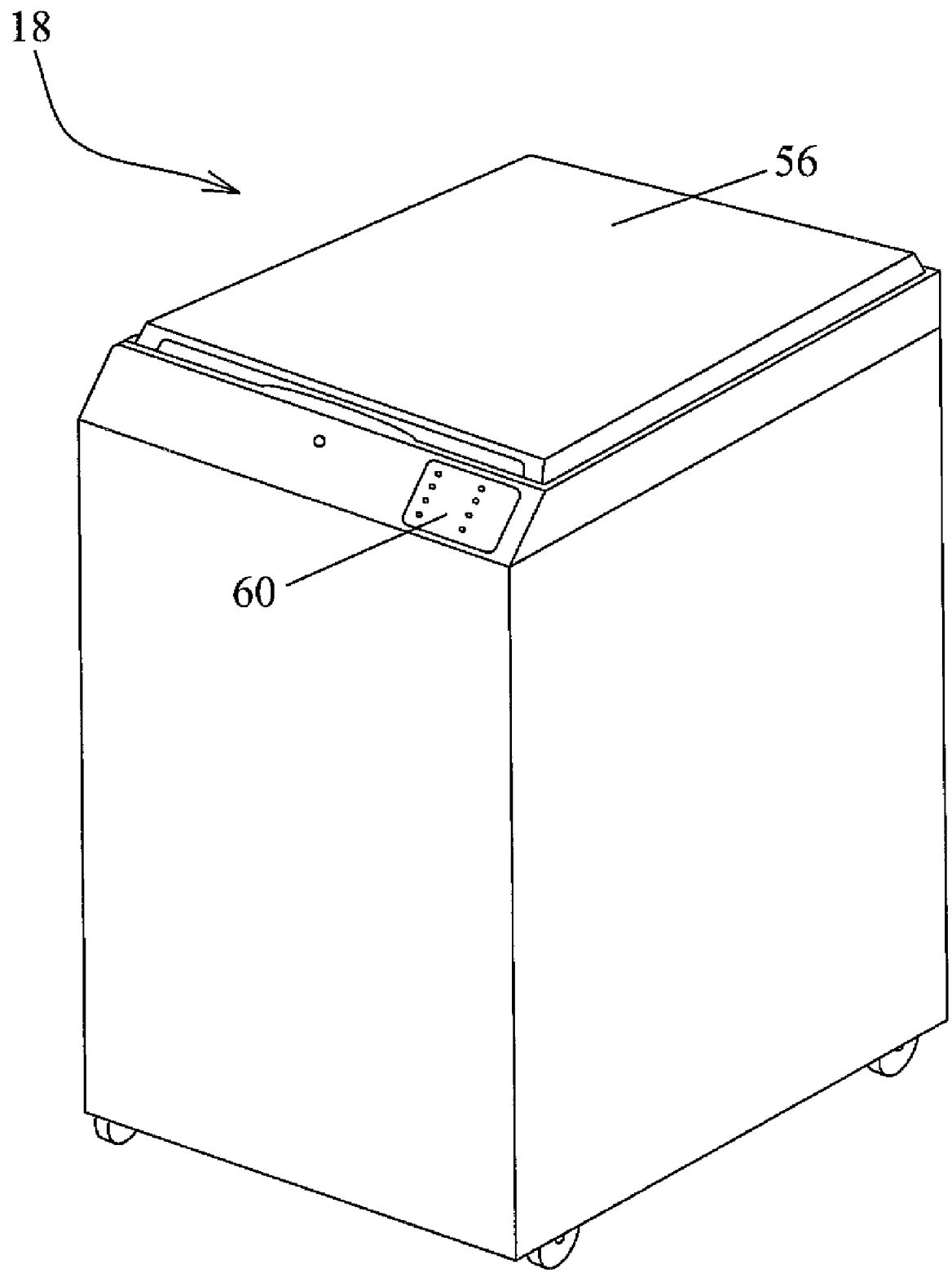
FIG. 1 includes sub-part FIGS. 1A, 1B and 1C which are isometric views (FIGS. 1B and 1C being partially cut-away) of an embodiment of a system according to the present invention.
Figure 1B:
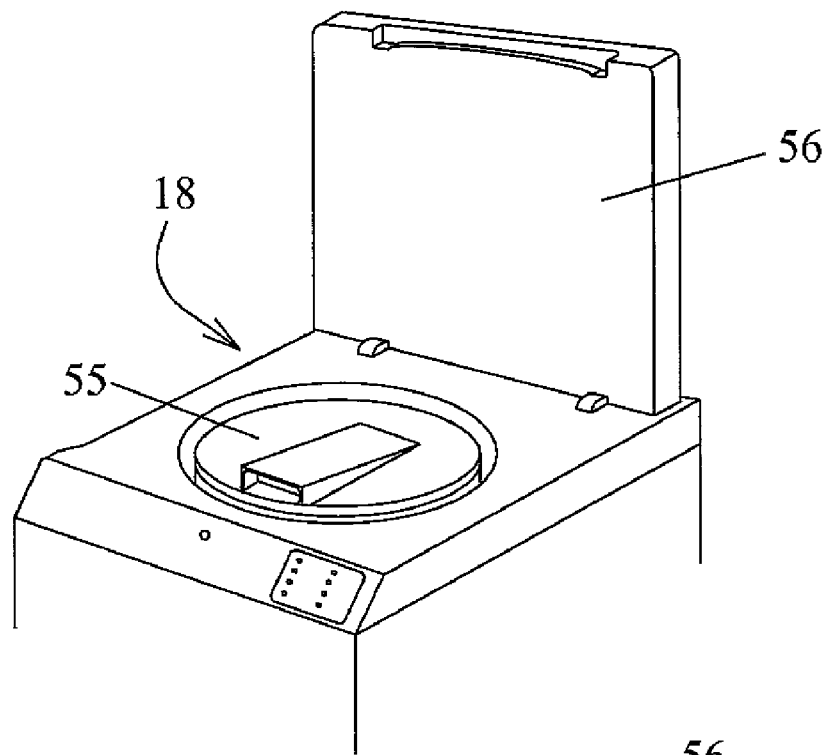

According to the present invention, a system/machine 18 as identified generally in FIG. 1 (see FIGS. 1A, 1B and/or 1C) may be employed to perform one or more separations preferably using centrifugal forces. Details of these and/or like centrifugal forces and the creation and/or application thereof, where necessary for an understanding of the present invention, will be revealed further below and/or may be available from the art, as for example may be understood from similar, previously existing machines/systems such as the COBE® 2991™ or the Gambro® Orbisac™ fluid separation machines or systems which are available from the assignee of the present invention, Gambro, Inc., and/or its subsidiary, Gambro BCT, Inc., both of Lakewood, Colo., USA.

A variety of alternative sets 10 of containers which may be used with the system/machine 18 of the present invention are shown in the drawings, see for example FIGS. 2-8, inter alia. A separation container 11 according to FIGS. 2-8 may be a part of the bag set or system 10 wherein in the primary embodiments hereof, the separation container 11 is annular and/or of a ring type. In some embodiments this may be flat, or it may be a somewhat frusto-conical separation container 11 and may be of a flexible plastic material, which in some instances, may be of the same or a similar type as used in conventional blood or blood component or other biological fluid bags. The separation container can be made, for instance, of two plastic sheets arranged one above and on top of the other, which can then be joined peripherally by one or more annular or substantially annular welds. These welds may be at least peripherally formed at inner and outer circumferential portions to then create an enclosed fluid separation region 11a and an inner central section 11b adjacent an open central area 11c defined by the ring bag 11.

Figure 2:
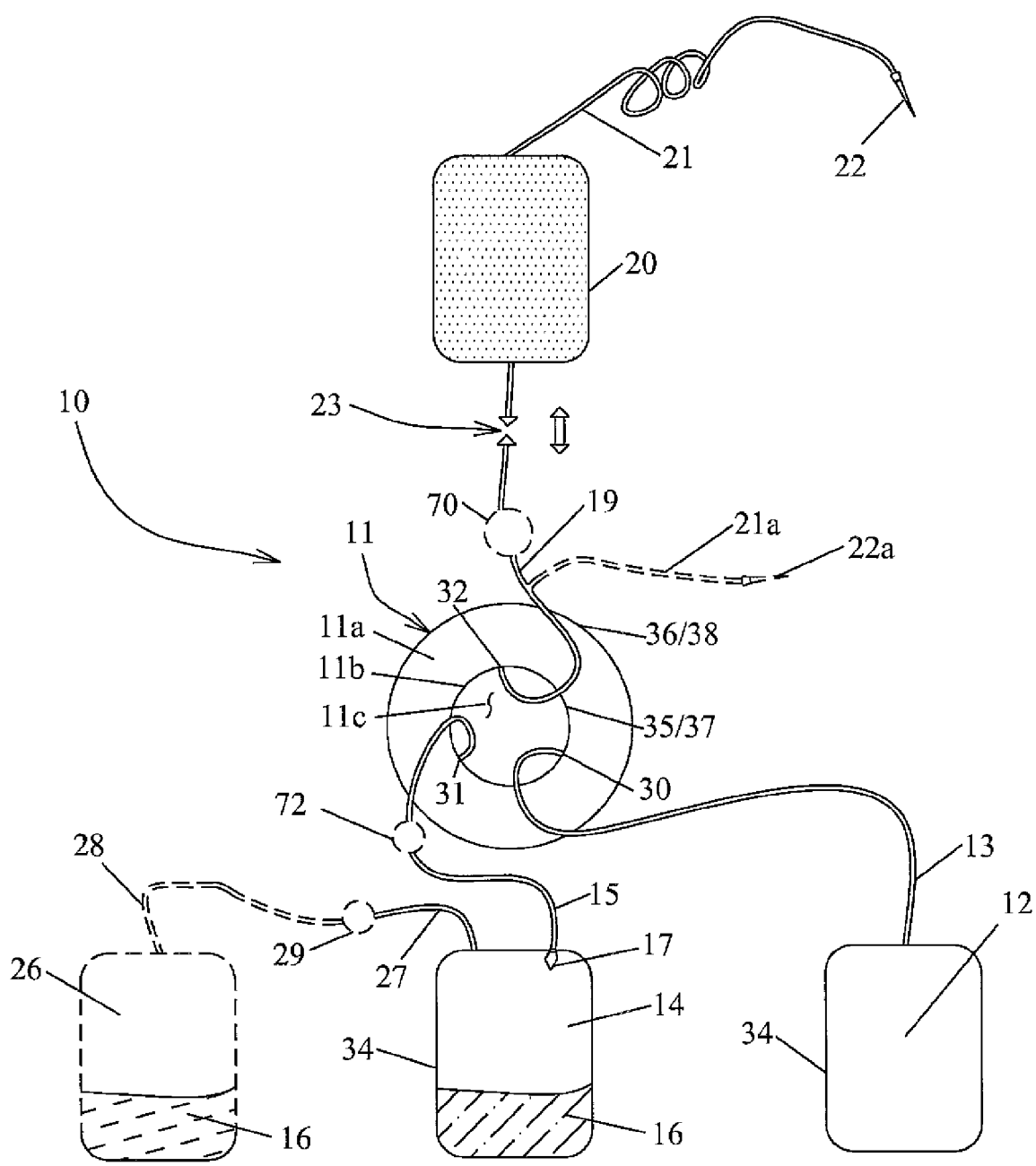
FIG. 2 is a schematic plan view of a separation set according to the invention.
Figure 3:
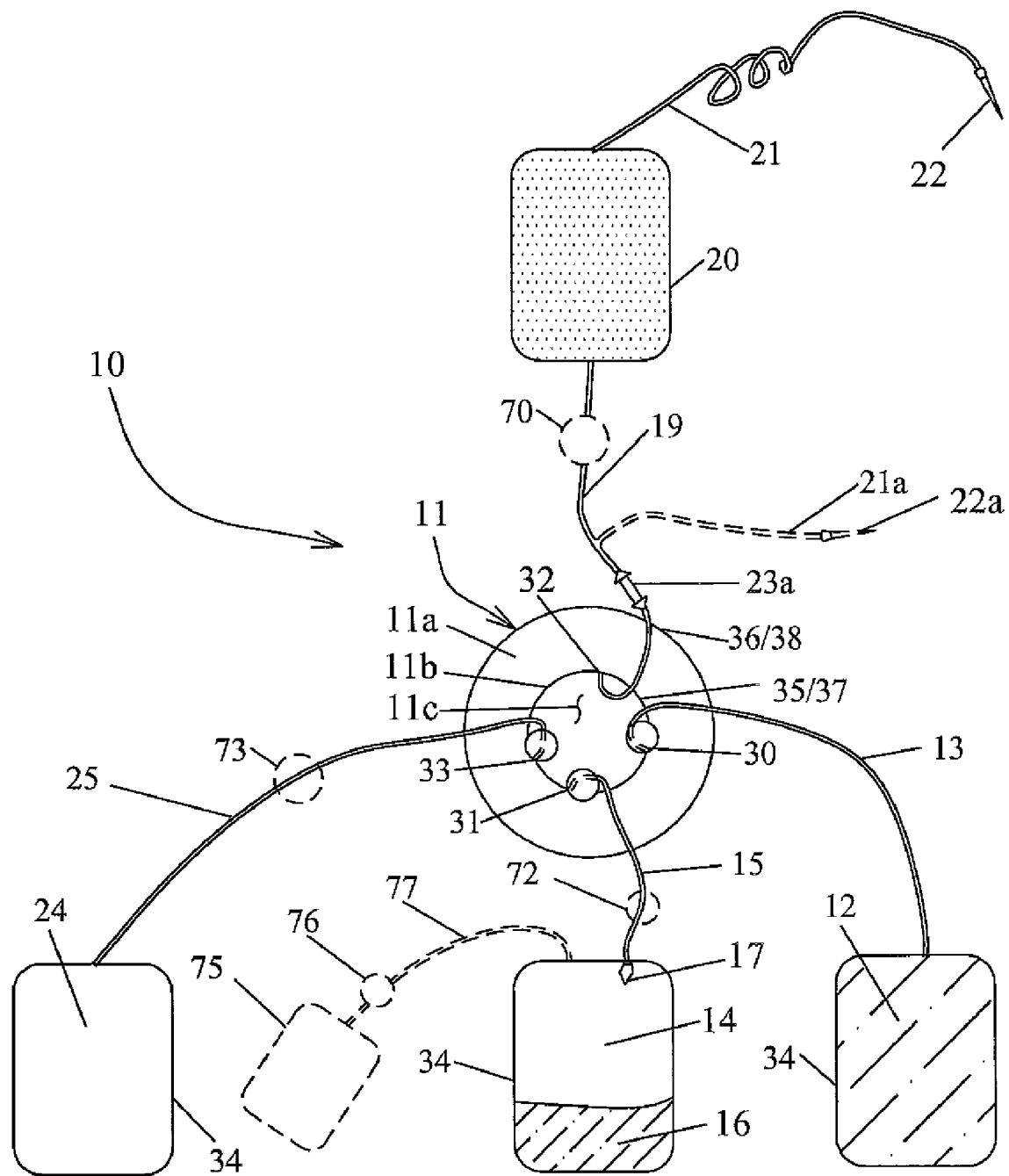
FIG. 3 is a schematic plan view of an alternative separation set according to the invention.

As shown in the relatively basic, substantially schematic embodiments of FIGS. 2 and 3, a first component collection container 12 may be connected by a tube 13 to the separation container 11, and a second component collection container 14 may similarly be connected to the separation container 11 by a second tube 15. Both such connections may be at the inner circumference of ring bag 11 as shown in FIGS. 2 and 3, or though not shown, either or both could be connected to the outer circumference or at any desired radial location therebetween. The finished component collection containers 12, 14 may be shaped in any of a variety of ways and/or formed of any of a variety of materials, though they may in some preferable embodiments be, as shown, substantially rectangular bags of flexible plastic sheet material of substantially conventional type, the plastic sheet material being preferably selected with a view to the type of cells or blood component products which may be chosen to be stored in the respective container. In the two component (2C) set or kit 10 of FIG. 2, these two collection bags 12, 14 are the only end product bags; however, in the three component (3C) set or kit 10 of FIG. 3, a third product collection bag 24 may also be connected by a third tubing line, here line 25, to the ring bag 11. In whole blood (WB) separation, the primary examples described herein, the first collection bag 12 may be adapted to receive plasma, the second collection bag 14 adapted to receive RBCs and the third collection bag 24, in the 3C set, adapted to preferably receive platelets. Note, the third collection bag 24 may alternatively be disposed to receive a buffy coat, though perhaps more typically or preferably, this would be a platelet product. In either of these or like cases, collection bag 24 may thus often be a smaller bag as shown for example in FIG. 6.

In the separation of whole blood and the preparation of blood component products, the bags may all be initially empty, or one or more of the secondary bags, e.g., the second component container 14 may be initially filled with a certain amount of an additive or storage fluid or liquid 16 for the component to be disposed therein, e.g., red blood cells. Examples of such a fluid may include the saline adenine glucose solutions known as SAG solution or SAG-M solution (SAG-M is a SAG solution which further includes mannitol), or other alternative additive solutions including AS-1, AS-3, or AS-5, inter alia. See FIGS. 2 and 3 where the additive solution 16 is predisposed in the bag 14. As an alternative, the storage or additive solution 16 may be predisposed in an optional separate bag, see, for example, satellite bag 26 in FIG. 2 (shown in phantom, dashed lines), which would be connected to or connectable with bag 14 via an additive solution tube 27 leading from bag 14, and a connecting tube 28 (shown in phantom, dashed lines). An optional sterile barrier or filter 29 represented schematically on line 28 in FIG. 2 may also be included, if a spike connection, or the like is used. The additive or storage solution 16 may then be passed from such a satellite container 26 to container 14 via lines 27, 28 (or, in some alternatives, the blood component product passed from bag 14 to the solution bag 26). In some embodiments, the solution bag 26 may be pre-connected to bag 14, i.e., during the manufacturing process of the set 10, or as an alternative, the additive solution bag 26 may be later connected or docked on via sterile docking or spike connection (or the like) and thus not be previously stored within or as part of set 10, but instead added at a different time, before or after blood component separation/processing. Note, shown schematically and more particularly in FIG. 3 is an RBC bag without an additive solution tube 27, but rather as mentioned with the additive solution 16 pre-disposed therein as may be during manufacture of the set 10 or otherwise later added yet prior to use. The component container 14 may in such a case then be temporarily sealed by, for instance, a so-called frangible or a breaking pin 17, or other sealing means such as a peelable or pressure rupturable seal (not shown here, but see description hereinbelow) to keep the solution sealed therein until its use may be desired, i.e., until loaded in the centrifuge and ready to receive a component product such as RBCs. With the platelet bag 24 (see FIG. 3), a storage or an additive solution (such as a platelet additive solution, or PAS (e.g., T-Sol)) (not shown) may similarly be pre-disposed in or adapted to be added to bag 24 for the benefit of the component product to be later added thereto.

In many embodiments such as the ones illustrated, the separation container 11 may be provided with a connection tube 19 which may be connected by sterile docking (or otherwise) to a source of whole blood (indicated at times herein by the abbreviation, WB) such as a separate WB bag 20, see the schematic sterile dock representation 23 in FIG. 2. Contrarily, FIG. 3 shows no docking, but instead what would be an alternative pre-connection of WB bag 20 to separation bag 11 via tubing line 19. In either case wherein a WB bag 20 is used, it would in many embodiments be removed (though not necessarily) prior to centrifugation. This removal option is shown schematically in FIG. 3 by the disconnection arrow(s) 23a, which could represent an energy wave, e.g., radio frequency sealing and cutting mechanism/process. Optional leukoreduction filters 70 are also shown on inlet line 19 (these will be described further below). Bag 20 may in either case be connected by a tubing line 21 to a cannula/needle 22 for connection to a blood donor (not shown). Whole blood collected from a donor into a bag 20 may then be passed from bag 20 into separation container 11 via tubing line 19. Otherwise, as shown (in phantom dashed lines) in FIGS. 2 and 3, intermediate bag 20 may optionally be bypassed or functionally and/or structurally eliminated and the separation container 11 may instead be more directly connected to a needle or withdrawal cannula 22a, provided via a withdrawal tubing line 21a connectable with or pre-connected to or as part of blood inlet tube 19. Blood could thus be donated directly from a blood donor (not shown) to the separation container 11. Note, bag 20 (or separation container 11, if bag 20 is not used) could have an anticoagulant charge (such as CPD or CP2D (citrate phosphate dextrose or citrate phosphate 2-dextrose) or ACD or ACDA (citrate dextrose solutions) or otherwise) pre-disposed or otherwise provided therein or added thereto before (or after) the blood collection therein.

The various different containers may also be provided with filling and/or withdrawal ports, or connections or connectors such as the ports or connections 30, 31, 32 and/or 33 in ring bag 11 (see e.g., FIGS. 2-6 and 7B). These ports may be of a type like those frequently used in or on blood or blood component containers or bags to provide fluid communication therethrough. The separation container 11 may be provided with one or more welded portions 35, 36 which are arranged to define respective inner and outer circumferences 37, 38 of the separation container 11. Thus, the ring bag 11 can have an inner open area 11c substantially defined by the inner weld 35 and/or inner circumference 37, which may provide an advantage as explored further below. Inner weld 35 may have ports 30, 31, and 32, and the optional additional port 33 defined therethrough (see particularly FIGS. 5, 6 and 7B). Such ports 30-33 may be discrete port structures (not separately shown) or may more simply be welded connections of the respective tubing lines 13, 15, 19, and/or 25 into proper fluid communication with the interior of container 11. Port 32 may be used to connect inlet line 19 to separation bag 11. Then, in the two-component version of FIG. 2, the tubes 13, 15 connecting the separation container 11 to the respective first and second component containers 12, 14 (see also FIGS. 3, 4A, 5 and 6, inter alia) may thus be disposed to pass through the inner weld 35 via the respective ports 30, 31. The component containers 12, 14 are similarly provided with welded portions or seams 34 at their outer edges, allowing the passage of the tubes 13, 15 (and/or port structures (not separately shown or identified)) therethrough. Tubes 13, 15 are connected in and through seams 34 by welding (or through ports) not unlike such connections in and through other conventional (or unconventional) biological fluid containers. The third component container 24 in FIG. 3 would optionally additionally be connected in like fashion via tubing line 25 through its respective port 33 to the ring bag 11, see FIGS. 3, 4A, 5 and 6. This third bag would also have a welded portion or seam 34 disposed therearound with one or more tubes (or ports) positioned therein and/or therethrough to provide communication thereinto, see e.g., the connection of tubing line 25 therethrough. As mentioned, the third bag 24 may be disposed to receive a buffy coat, or likely more often, a platelet product, and thus bag 24 may often be a smaller bag as shown for example in FIG. 6.

In FIG. 4, which includes sub-part FIGS. 4A and 4B, a more detailed, yet still substantially schematic view of the ring bag 11 is shown. In both FIGS. 4A and 4B, the ring bag 11 is shown with its parts, the enclosed fluid separation area 11a, the inner circumferential area 11b and the open central area 11c. Also shown in both views are the inlet line 19 with its associated port 32, and respective outlet lines 13, 15 and 25. However, each of the respective ports/connections 30, 31 and 33 are shown connected to the bag 11 only in FIG. 4A. In FIG. 4B, an alternative porting means or structure is shown where a single port or tubing connection 30 is disposed connected to the bag 11 with corresponding branched ports or connectors 31a and 33a emanating from the tubing line 13 connected to port 30. Branched port 31a connects to outlet line 15 and branched port 33a connects to outlet line 25. Note, as will be described in more detail below, the outlet lines are shown as disposed in flow control valve support members 41. Also, an alternative leukoreduction filter 74, for on-line filtration is shown in phantom in FIG. 4B, and this will also be described further below.

Figure 5:
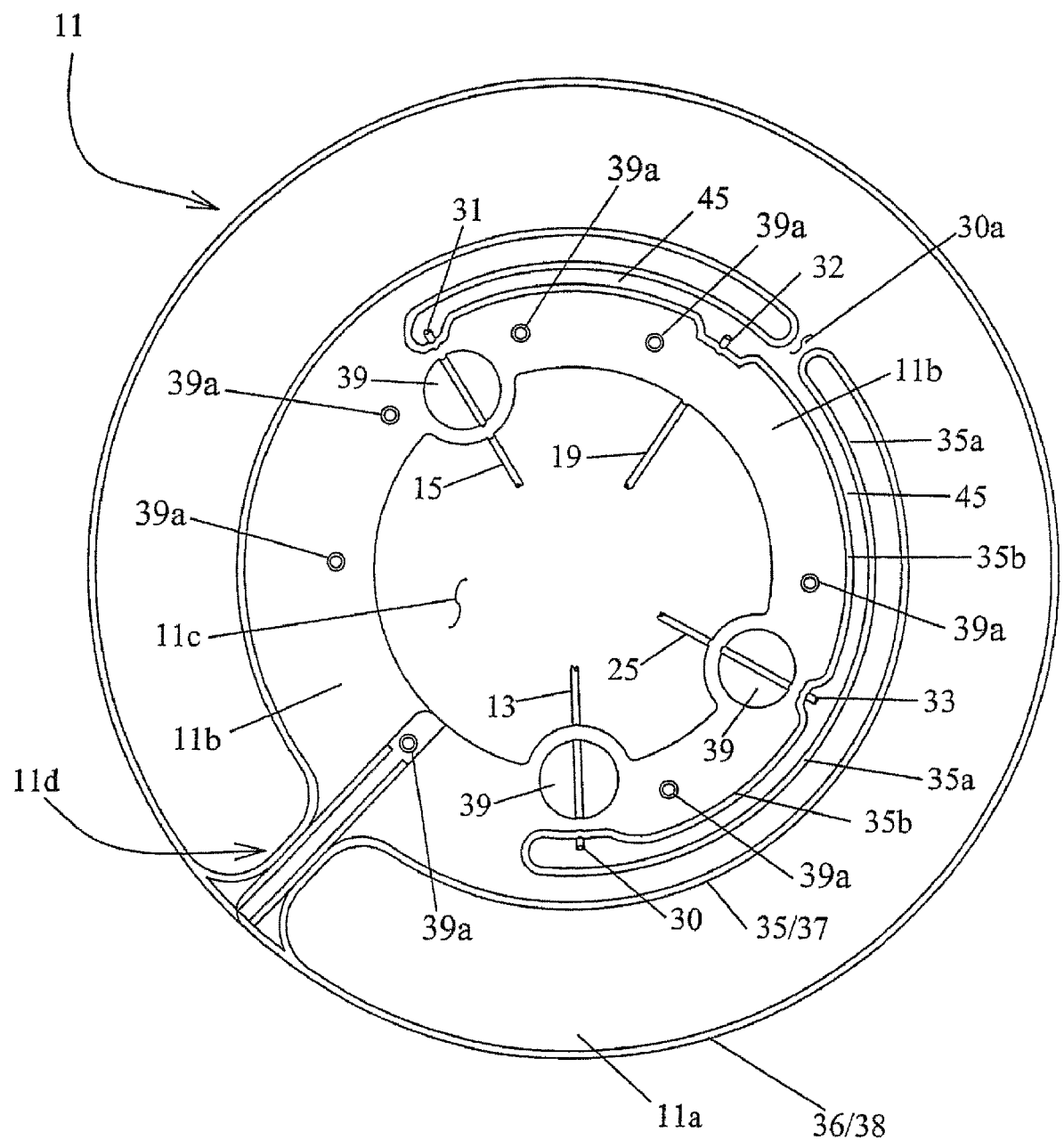
FIG. 5 is a plan view of another embodiment of a separation container according to the present invention.

In the alternative embodiment shown in FIG. 5, the separation container 11 is shown in an enlarged schematic view wherein the annular fluid chamber 11a is shown defined between inner weld/circumference 35/37 and outer weld/circumference 36/38. Note, in this FIG. 5 embodiment the annular fluid chamber 11a is not open in fluid communication around the 360 degrees of the separation container 11. This is in opposition to the wholly open flow area as schematically represented in FIGS. 2-4 and 6. In this alternative embodiment of FIG. 5, this alternative closed communication area is identified generally by the reference numeral 11d. In some embodiments (like that shown here in FIG. 5), this closure may be formed by welding or with a folded over or an otherwise overlapping of relative layers of material.

An overlapping of material from an initially flat bag can be used to create a conical shape of the bag 11 as may be desirable in certain embodiments herein, see FIGS. 7B and 8-14, for example. A conical shape of the container may be beneficial in reducing the sedimentation distance, i.e., radial travel distance, of a quantity of red blood cells in a quantity of blood. This limiting of the radial extent in which the liquid may move, may result in relatively more rapid separation and relatively smaller interfaces between the separated layers than the distances and/or interfaces experienced in relatively flat rotors.

Also defined in this alternative embodiment of FIG. 5 (and see FIG. 6) is a semi-circular inner flow distribution channel 45 defined by opposing outer and inner welded boundaries 35a and 35b. Generally, the distribution channel is shaped so that, when the separation container 11 is spun by a centrifuge, any fluid contained in the channel leaves the distribution channel and flows into the annular fluid chamber 11a. Access to this distribution channel 45 from/to chamber 11a may be had via opening or bay area 30a. Inlet flow through port 32 and/or outlet flows through ports 30, 31 and/or 33 may then communicate with/into and through the distribution channel 45 to and/or from fluid chamber 11a. The characteristics of flow in the various chambers and channels of a ring bag 11 (closed as at 11d or open as in FIGS. 2-4 and 6) will be described further below. Note, the bay area 30a may have a gradually reducing radial inlet bay area, reducing from the radial extent of the inner weld/circumference 35/37.

Figure 6:
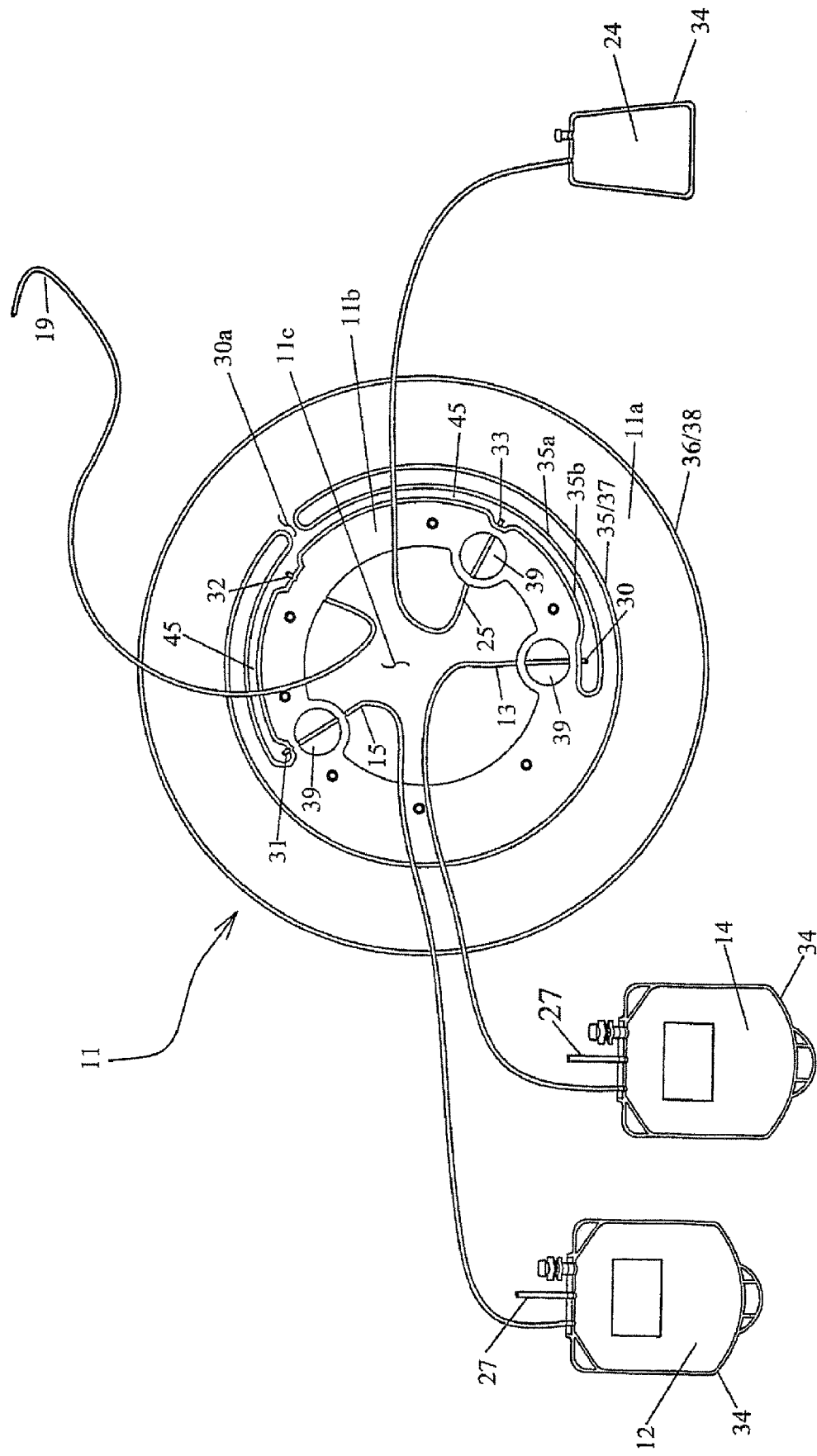
FIG. 6 is a plan view of another embodiment of a separation set according to the present invention.
Figure 7A:
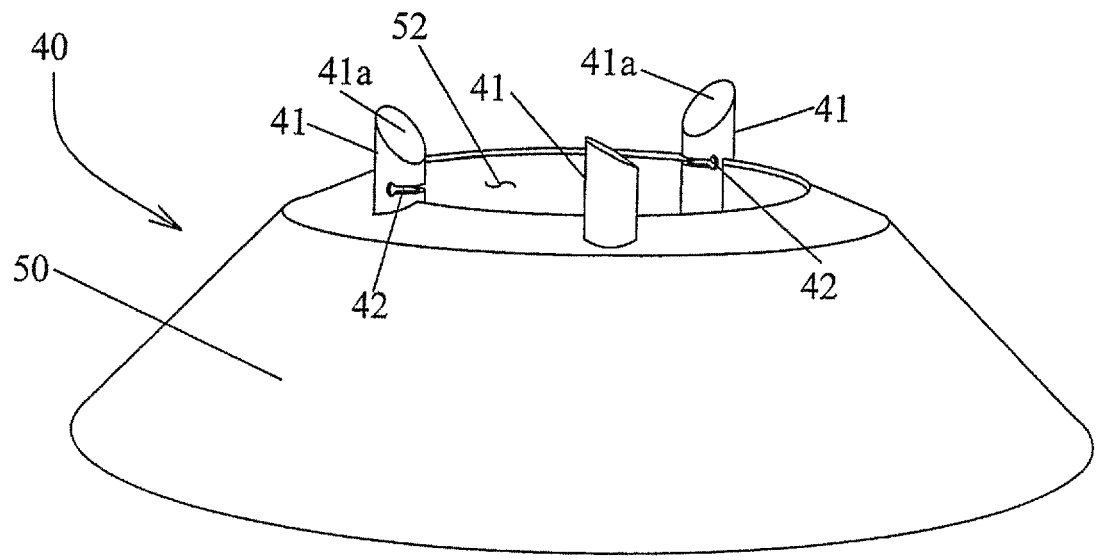
FIG. 7 includes sub-part FIGS. 7A and 7B which are isometric views of a turntable of a centrifuge rotor and a separation set according to the present invention.
Figure 7B:
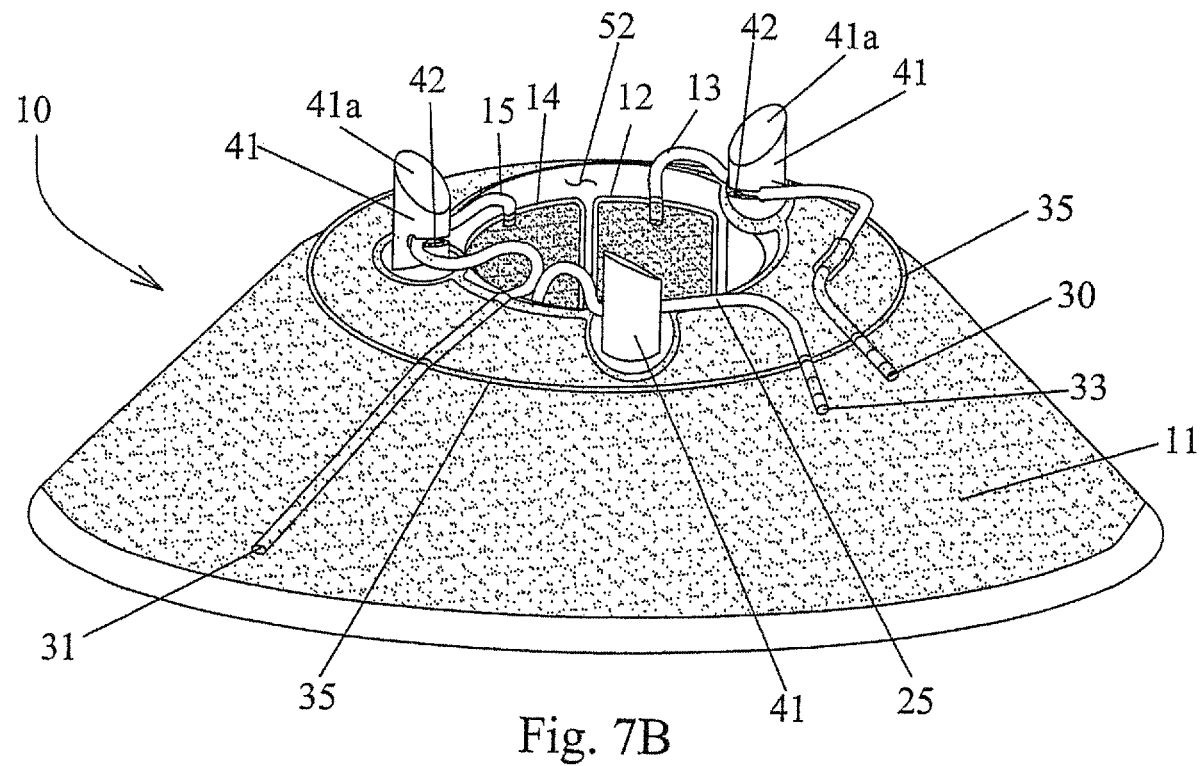
Figure 8:
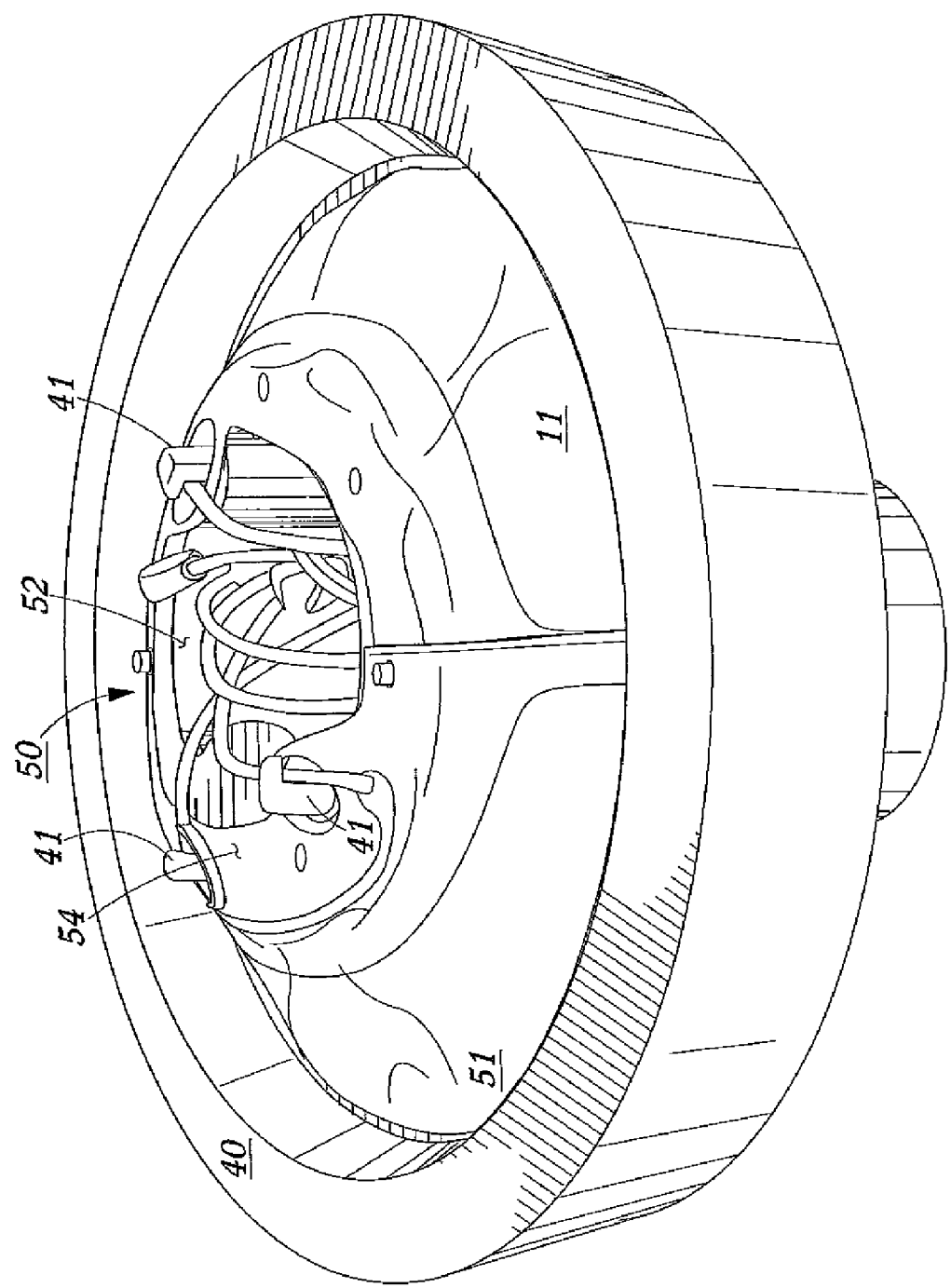
FIG. 8 is an isometric view of a turntable of a centrifuge rotor in which a set according to any of FIGS. 2-7 is shown mounted.
Figure 9:
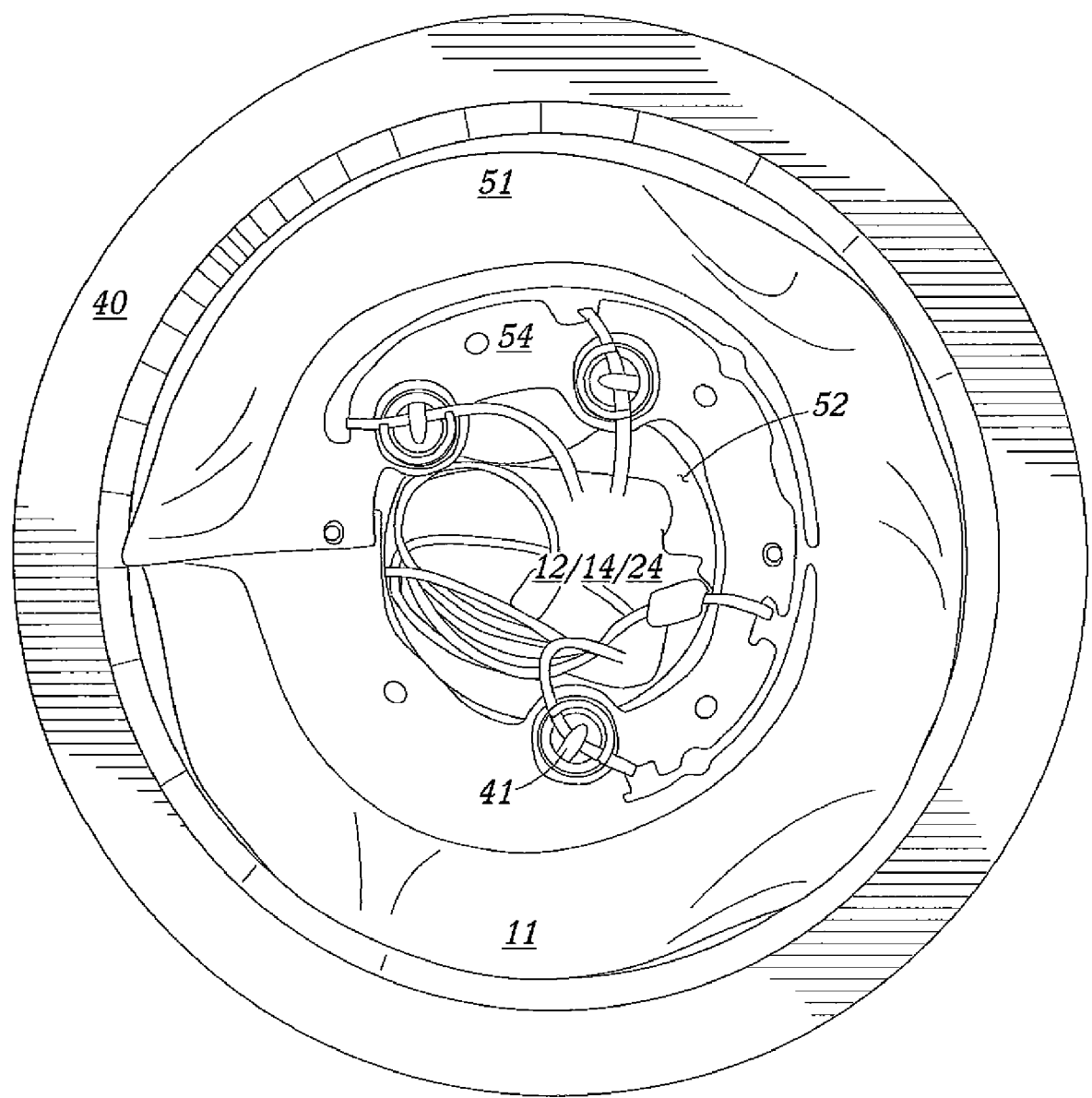
FIG. 9 is a plan view of an embodiment of a system like that shown in FIG. 8.
Figure 10:
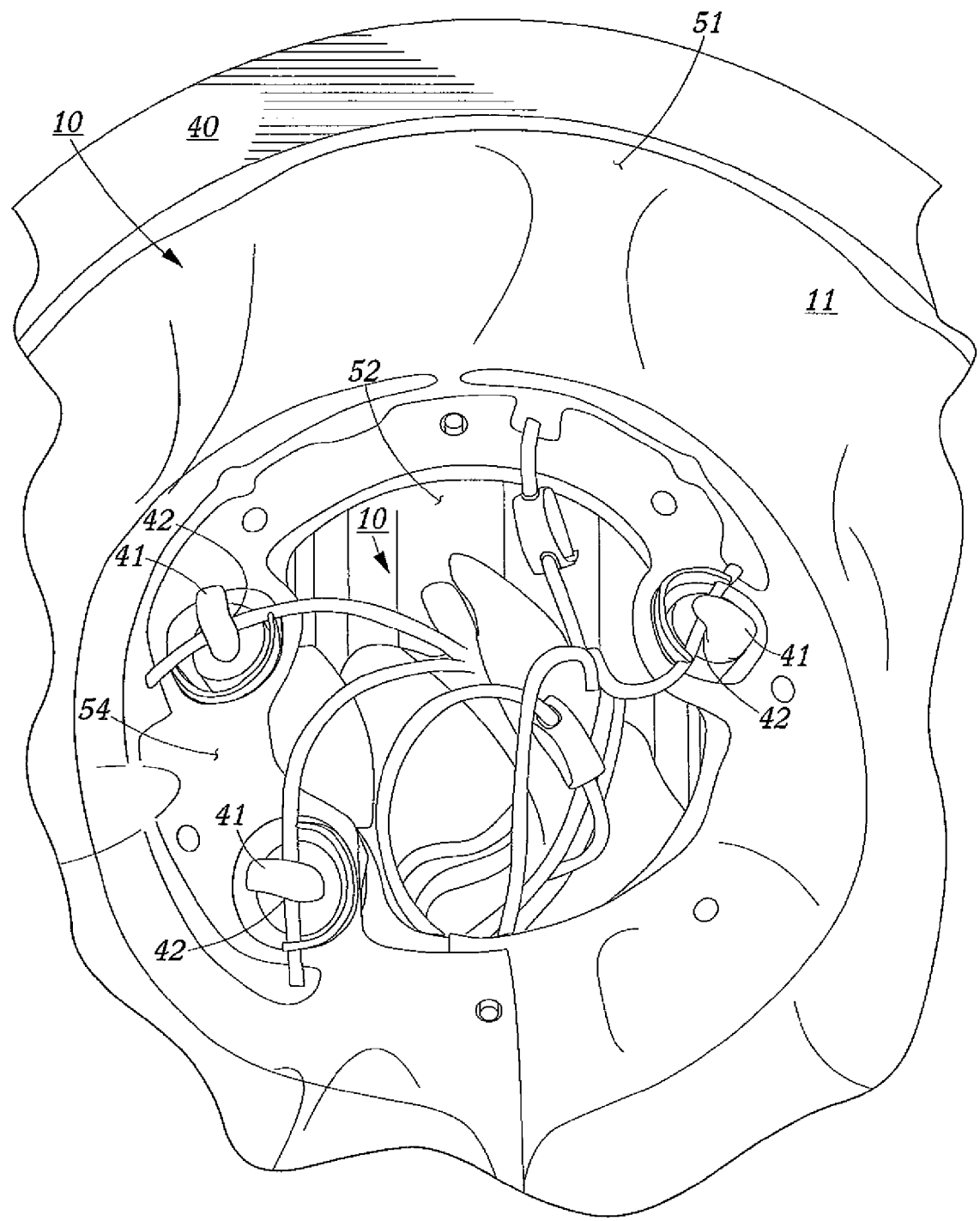
FIG. 10 is a close-up plan view of the loaded separation set of FIG. 9 according to the invention.
Figure 11:
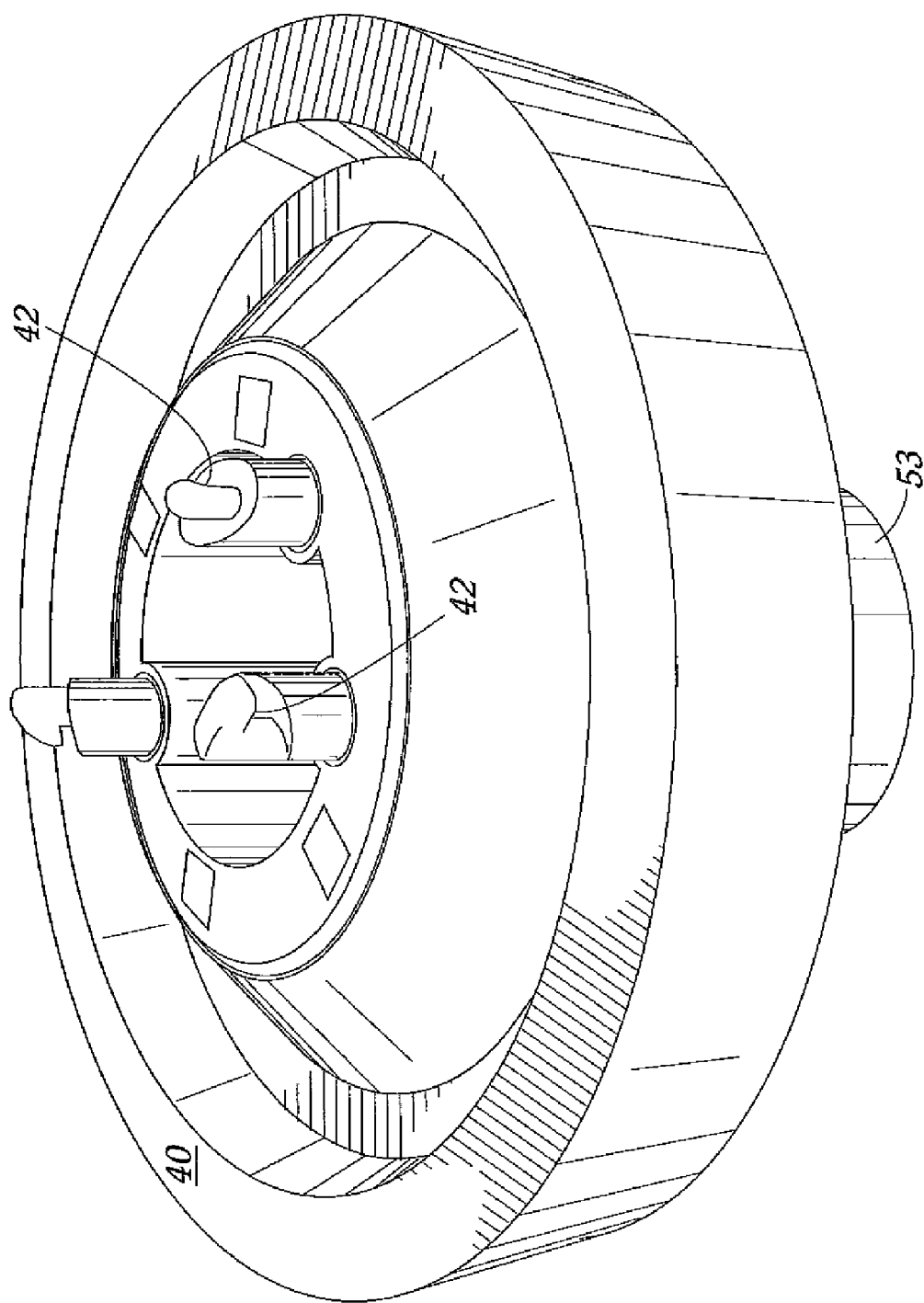
FIG. 11 is an isometric view of an unloaded turntable according to the invention.
Figure 12:
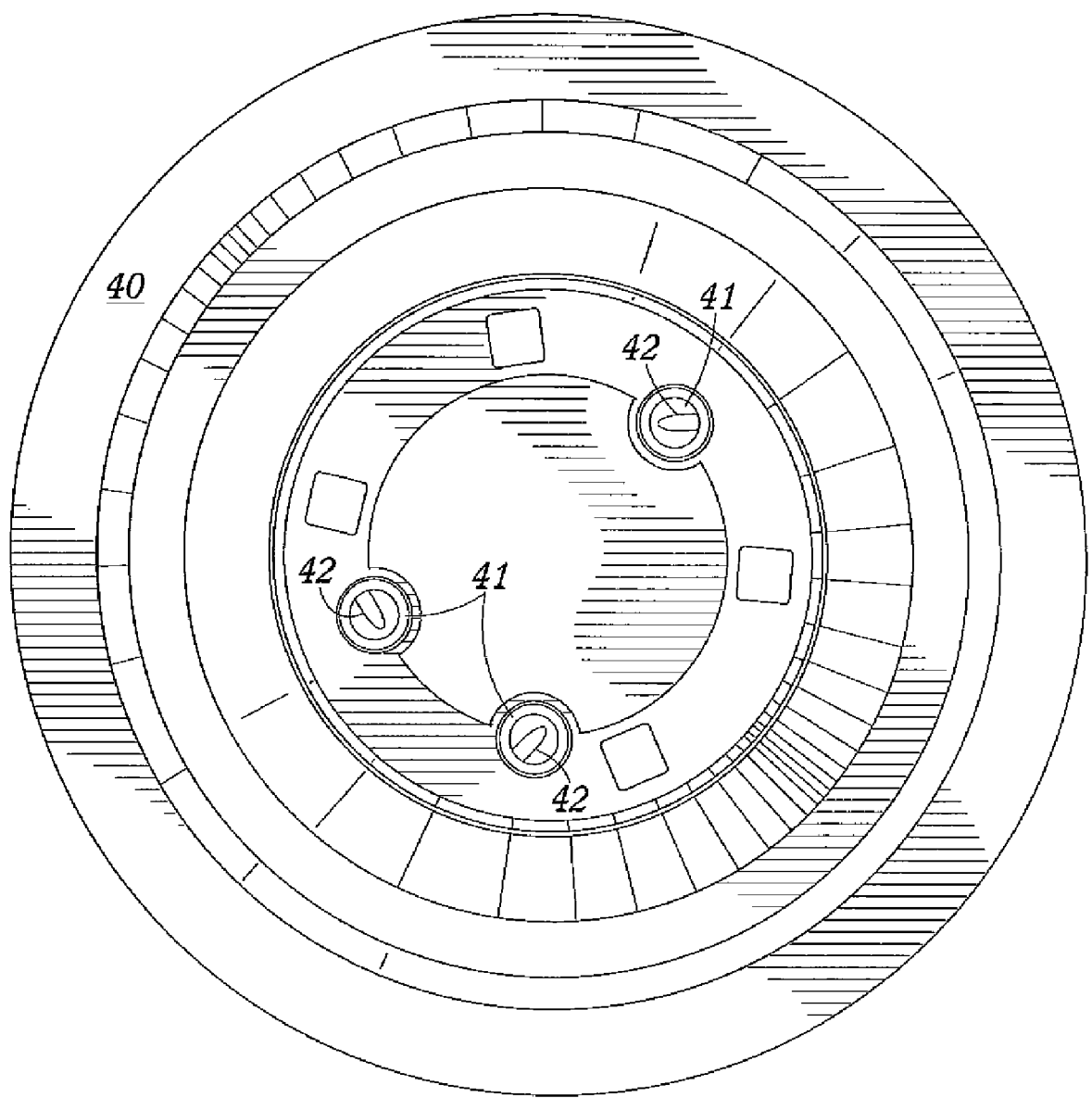
FIG. 12 is a plan view of the unloaded turntable of FIG. 11.
Figure 13A:
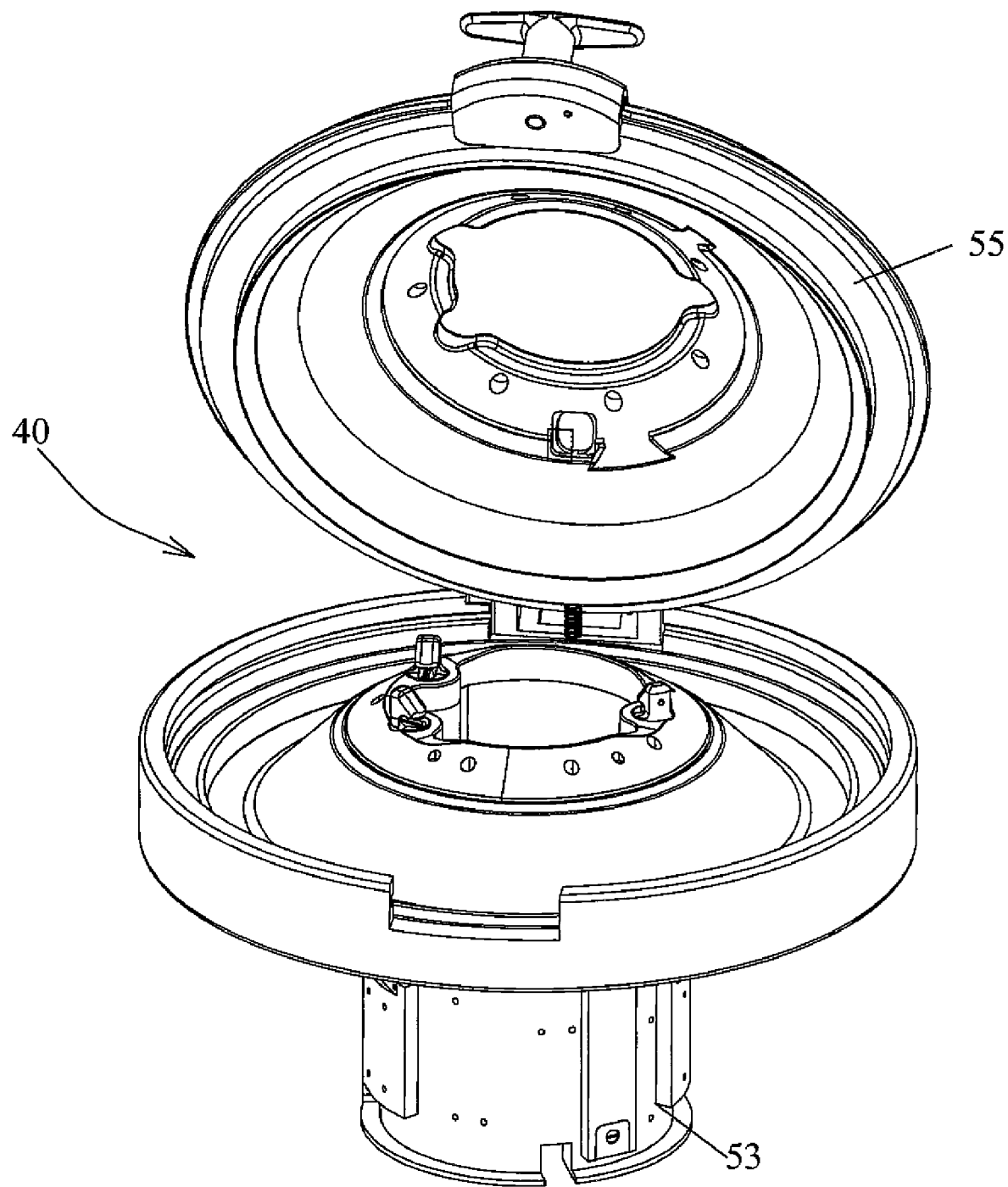
FIG. 13 includes sub-part FIGS. 13A and 13B which are isometric views of a centrifuge rotor with respectively an open and a closed rotor cover.
Figure 13B:
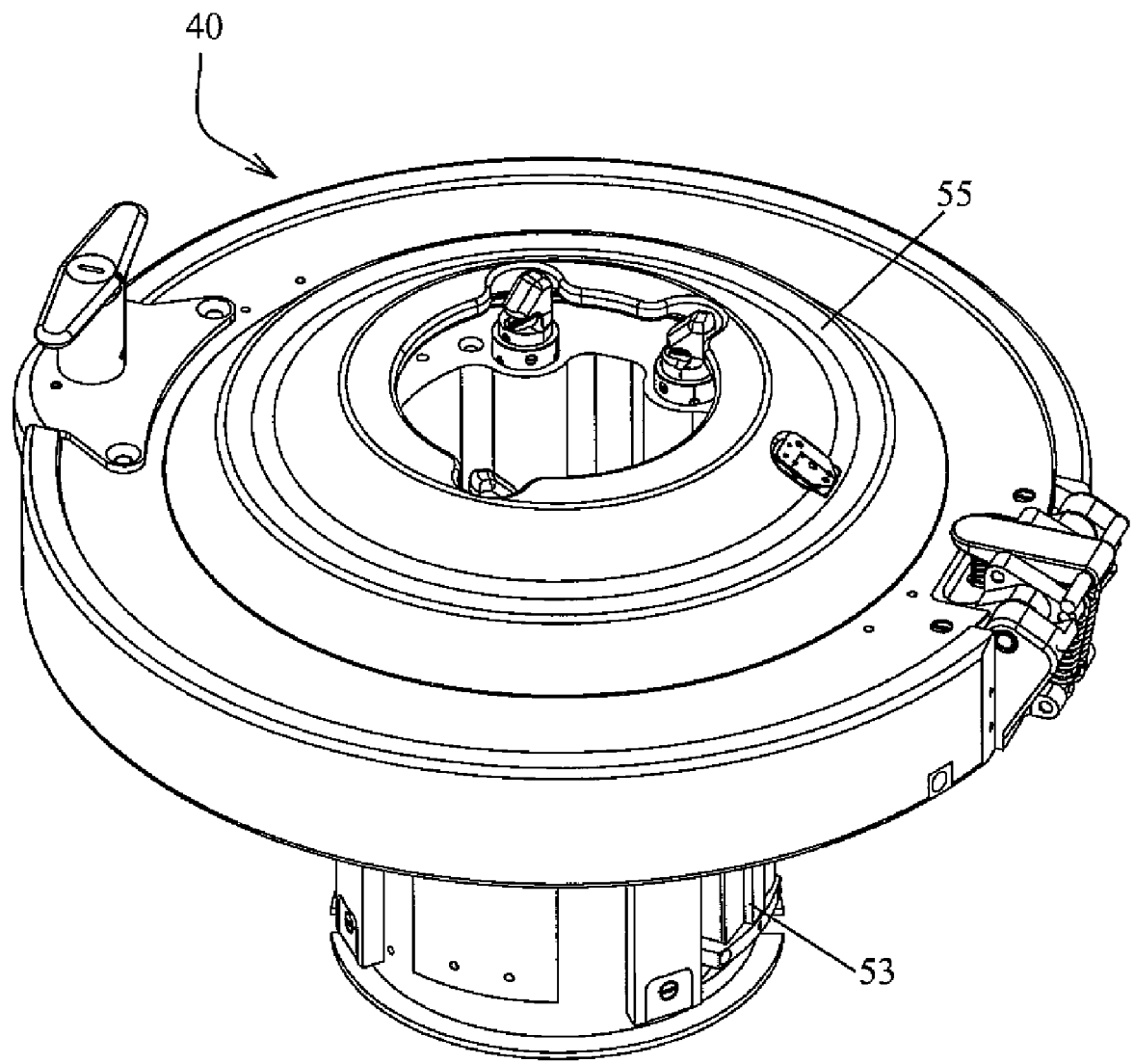

In many embodiments as for example those shown more particularly in FIGS. 5 and 6, the separation container 11 may also be formed with a number of holes or apertures 39 through the container in or adjacent the central section 11b and/or adjacent the inner open area 11c. As mentioned, the opposing top and bottom walls (plastic sheets) of the container 11 may preferably be in some portions welded together, see e.g., welded area 35 (and areas 35a and 35b) in the inner area 11b around the open interior area or space 11c, and the holes 39 may be formed through or adjacent this (or these) area(s) 35 (and/or 35a or 35b). Though not explicitly shown, only a small portion at or near the inner periphery, or a majority or the entirety of the inner area 11b may be of a welded nature. The holes 39 may then be formed through welded plastic or non-welded as the case may be. These holes 39 may then also be adapted to or cooperative with one or more rotor support members 41 (see FIGS. 3, 4 and 7-17; particularly 7, 10, 11, 16 and 17) which are disposed in/on the centrifuge rotor 40 (FIG. 7). Rotor support members 41 may be adapted to be inserted in and through the holes 39 and may thereby have a portion of the welded area 35 and/or a corresponding portion of the inner area 11b disposed thereon and/or therearound such that the rotor support members 41 may receive and thereby support the container 11 thereon. As shown in FIGS. 5 and 6, portions of respective tubing lines 13, 15 and/or 25 may be preferably disposed in, and/or secured within and/or across respective openings 39 so that these respective tubing line segments may be desirably positioned relative to respective support members 41 as described further below. Further alternative additional support apertures 39a are also shown in FIG. 5. These apertures 39a may provide further support in maintaining the separation bag 11 in operable position on rotor 40 (further description(s) hereof are set forth below).

Respective loaded and unloaded rotor turntables 40 are shown in FIGS. 7-15 inter alia. Generally, FIGS. 7-10 show views of the turntable 40 having a separation set 10 arranged or loaded therein in/on, and FIGS. 11-15 illustrate embodiments of an empty or unloaded rotor turntable 40. To now describe in more detail, an unloaded rotor turntable 40 is shown in FIG. 7A and a correspondingly loaded rotor turntable 40 is shown in FIG. 7B. The empty rotor turntable 40 of FIG. 7A schematically depicts a conically declining separation area 50 (taken from the inner portion toward the outer edge). Conically declining rotor turntable embodiments are also shown in FIGS. 7B and 8-14. A planar rotor turntable is shown in FIG. 15, and conically inclining rotor versions are not shown in the figures. Returning to FIG. 7, and particularly 7A, an inner or central open compartment 52 is also shown with three adjacent support members 41. The support members may be positioned in, partially in (as shown) or wholly out of the open central compartment 52. The support members 41 may also each have a valve member 42 disposed therein. The loaded rotor turntable version of FIG. 7B includes a bag and tubing set 10 loaded thereon. More particularly, a separation container 11 is shown loaded on/in the separation area or space 50. The end product containers 12, 14 (and/or 24 (though not seen in this angular disposition here)) are loaded in operative position in the central area or compartment 52 of rotor 40.

Figure 15A:
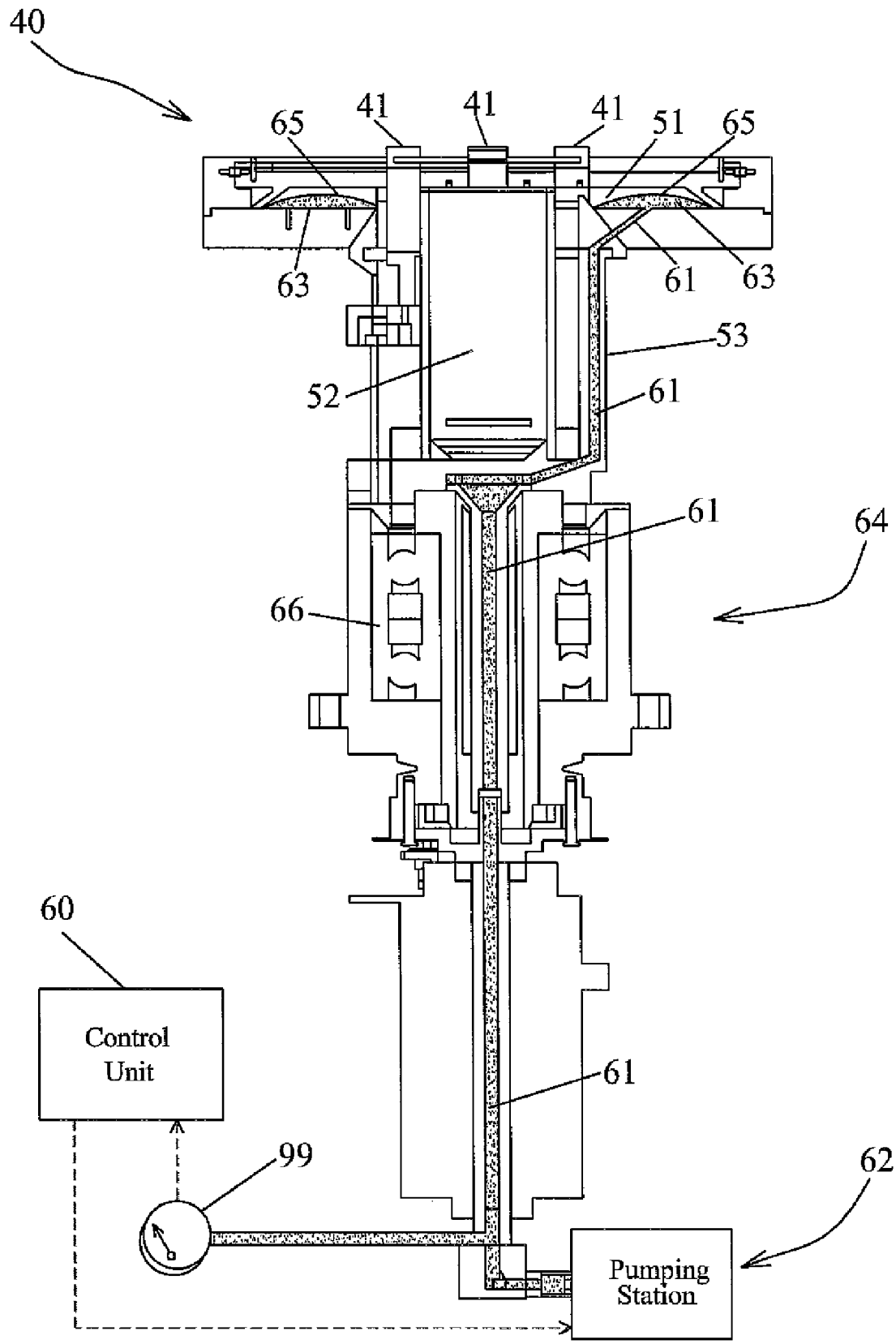
FIG. 15 includes sub-part FIGS. 15A, 15B and 15C which are sectional views of embodiments of a rotor assembly and hydraulic system of the present invention.
Figure 15B:
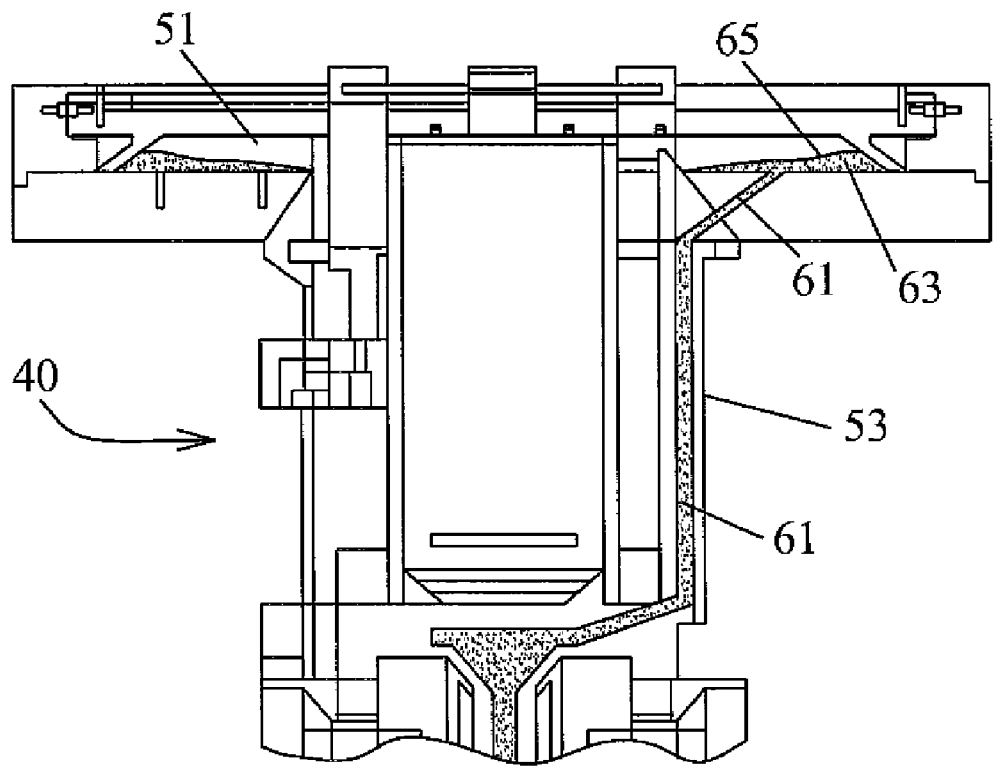
Figure 15C:
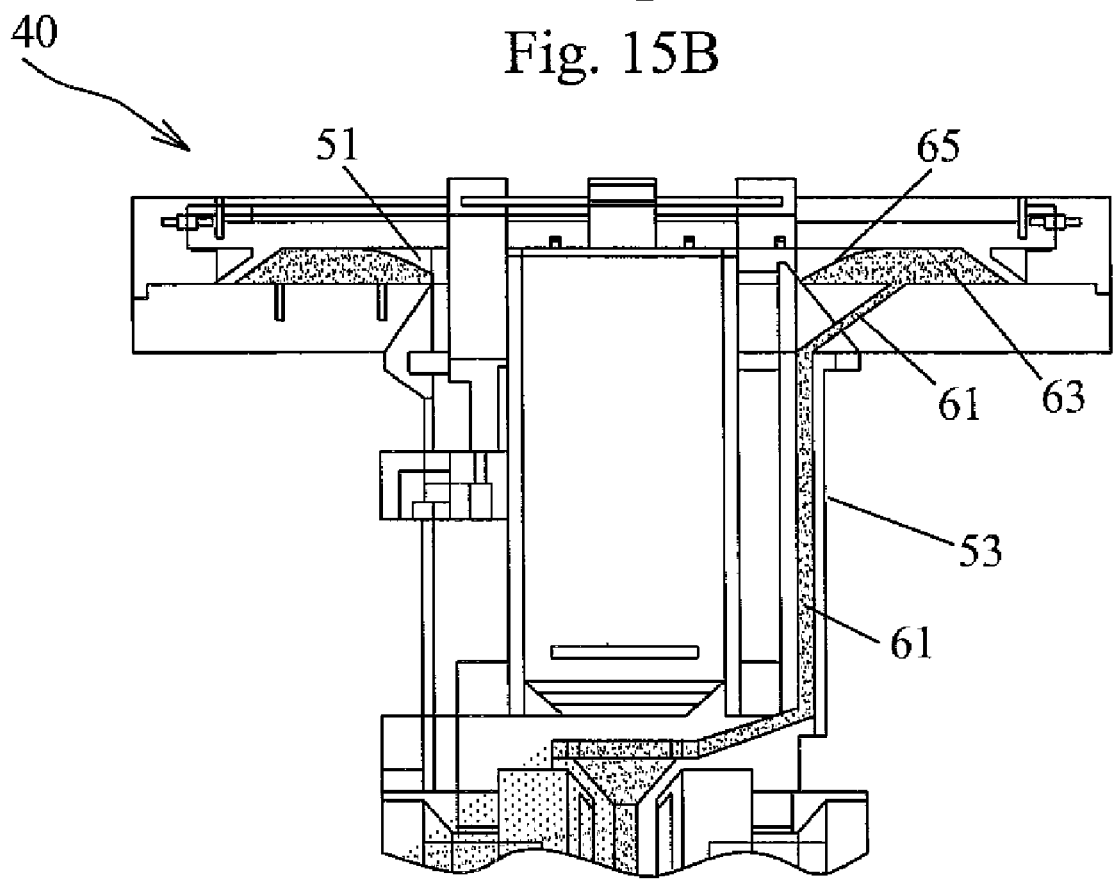
Figures 16A, 16B, 16C:
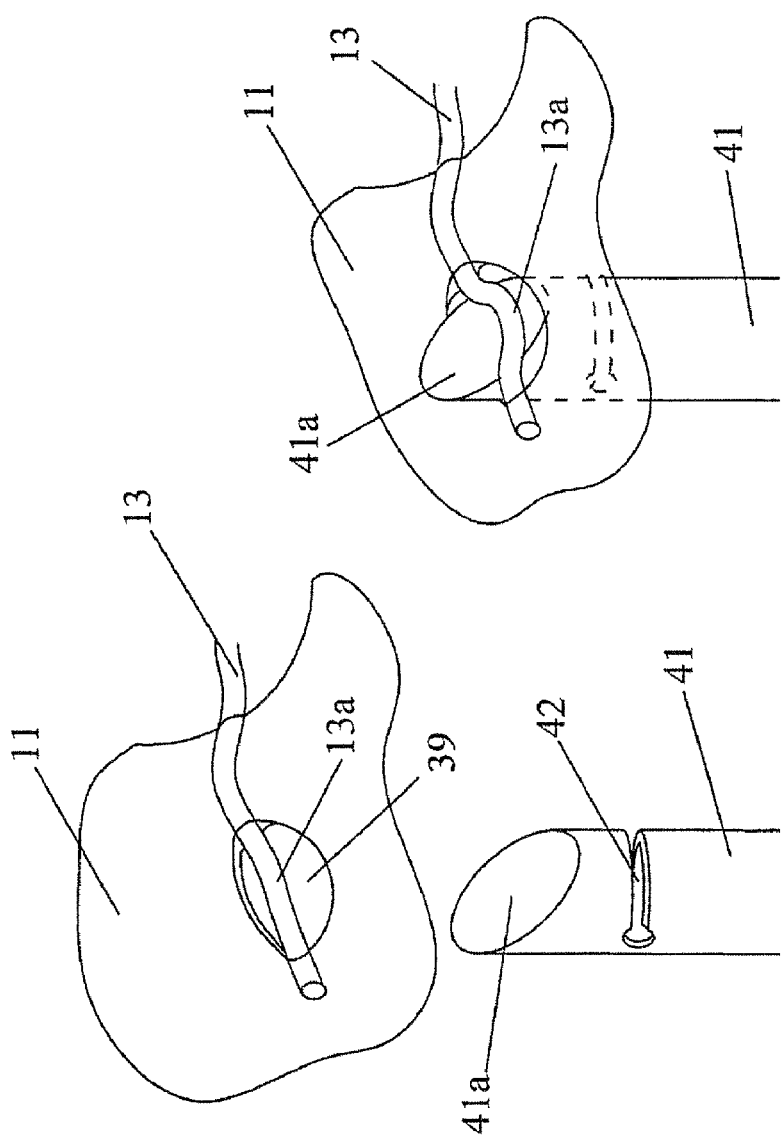
FIG. 16 includes sub-part FIGS. 16A, 16B and 16C which are isometric cut-away portions of valve and welding/cutting members of a centrifuge rotor according to the present invention.
Figure 17A:
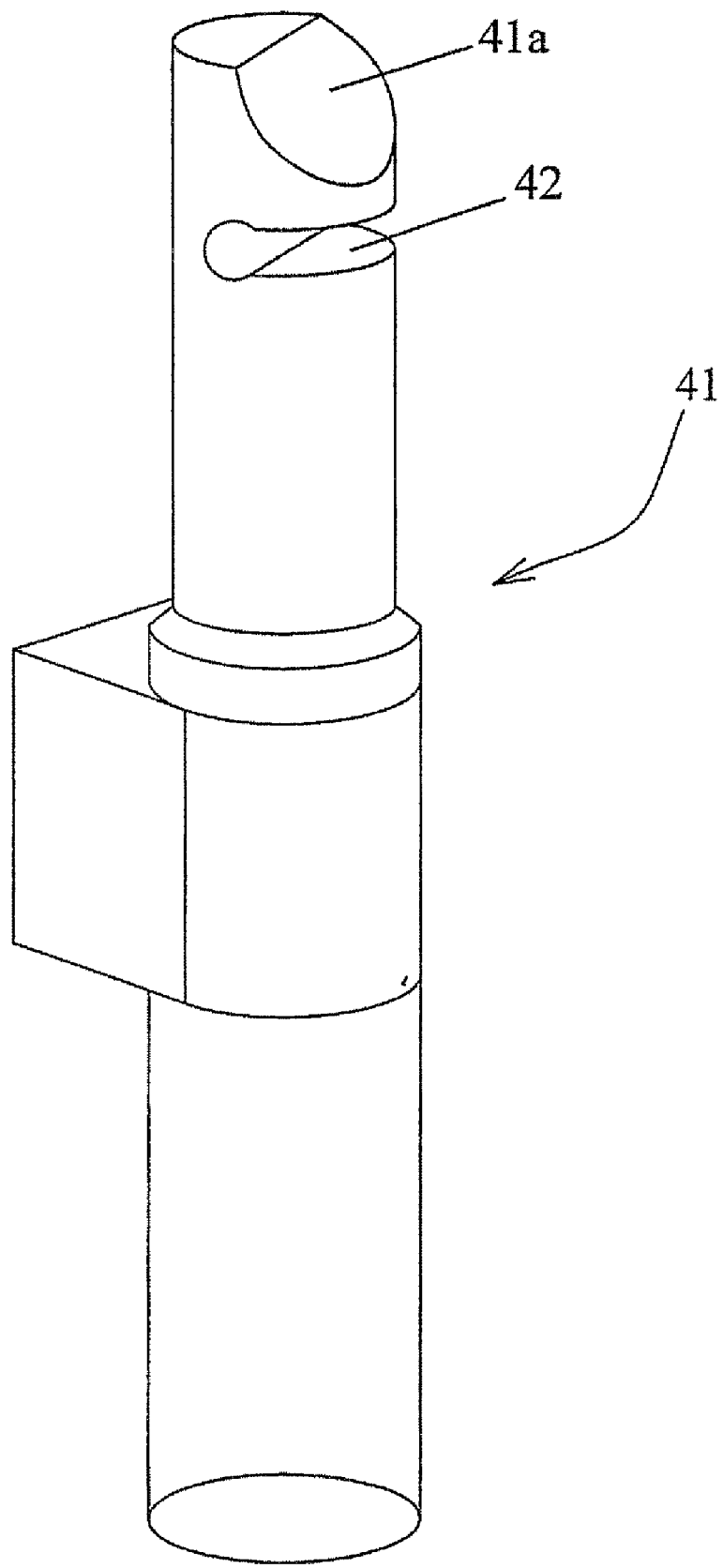
FIG. 17 includes sub-part FIGS. 17A, 17B and 17C which are an isometric view, an elevation and a cross-section of a cut-away valve and welding/cutting members like those in FIG. 16.
Figure 17B:
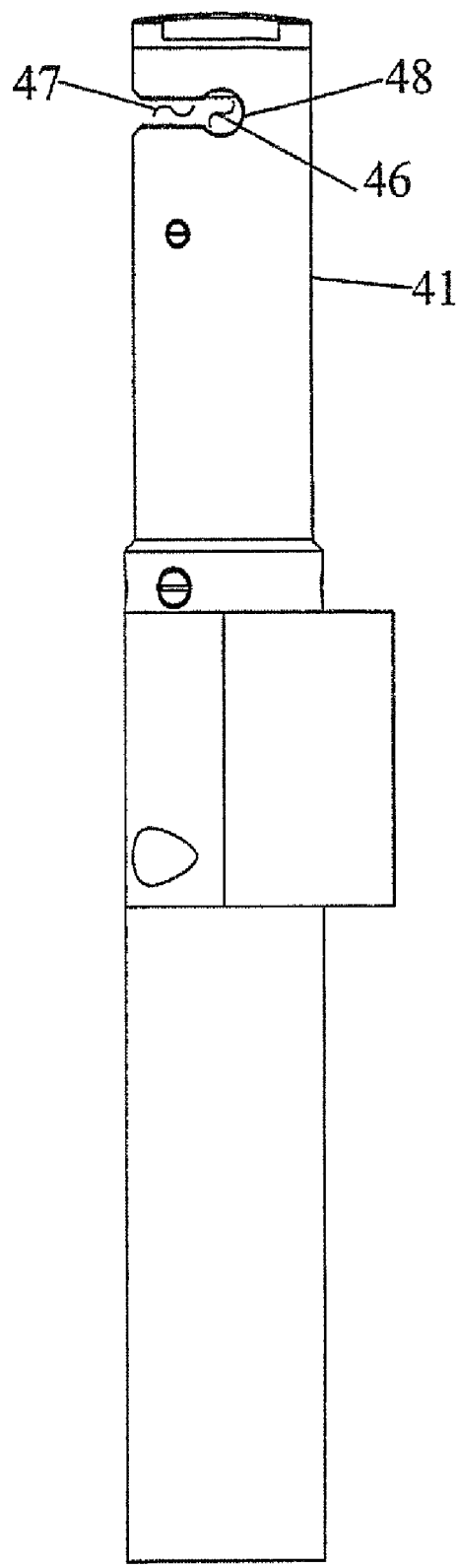
Figure 17C:
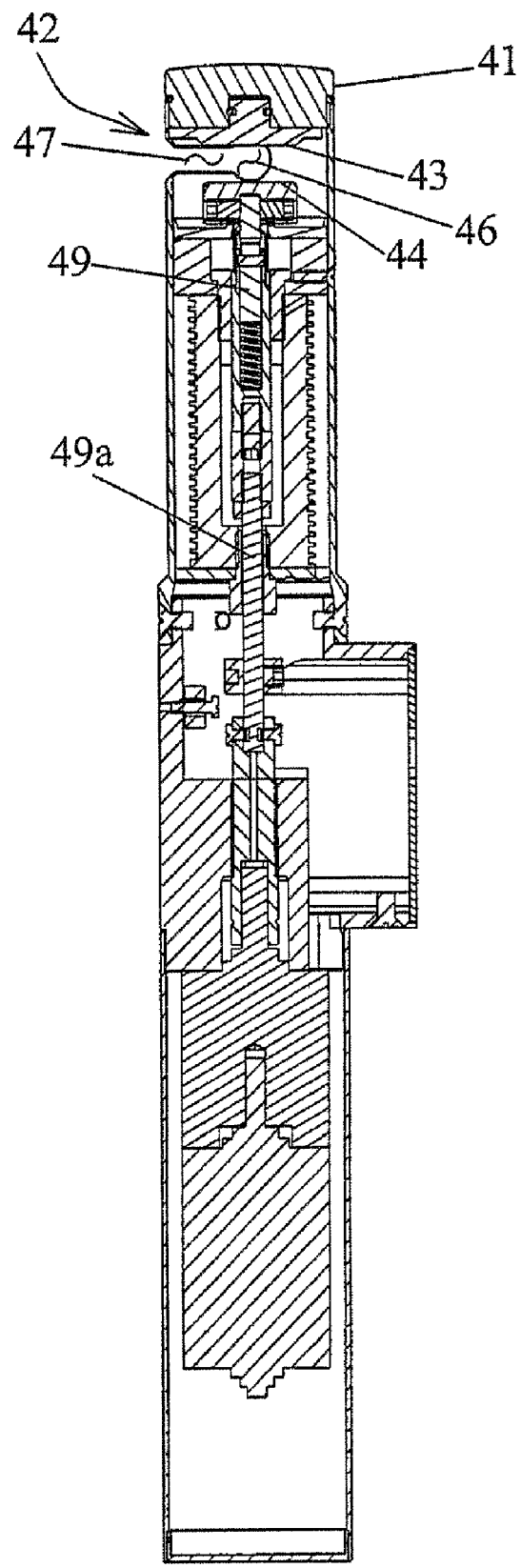

The tubes connecting the respective bags of the separation set 10 may then preferably be engageable by one or more pinch valves 42 (FIGS. 7A and 7B and see FIGS. 16 and 17, described below) which may be mounted in the central part of each of the retaining mounts or support members 41 of the centrifuge rotor apparatus 40. The pinch valves 42 (FIG. 16) may each include two contrarily disposed clamp elements 43 and 44 (see FIGS. 16 and 17, see particularly FIG. 17C) which are operatively coupled such that the clamp elements 43, 44 can be brought together adjacent to each other (not shown) or alternately opened so as to define a certain space 46 between themselves (FIGS. 17B and 17C). The clamps may be substantially flat as shown or may be slightly cupped to facilitate the reception of the respective rounded tubing lines therein. The clamping elements are operative relative to each other from either side of the respective tubing lines 13 or 15 and/or 25 (or potentially even 19, though not shown) when the clamping devices 42 (with clamping elements 43, 44) extend through the respective holes 39 in container 11 and the tubes 13, 15 and/or 25 are reeved into and/or otherwise disposed in the respective valve spaces 46 (as in FIG. 7B, inter alia). Note as shown in FIGS. 16A, 16B and 16C (and see generally FIGS. 7B and 17A), an inclined top face 41a can be used during the loading process to ease the delivery of the tubing line, e.g., line portion 13a of tubing line 13 into proper position in the valve 42. As shown in the sequence of FIGS. 16A, to 16B finally to 16C, a separation container 11 can be brought downwardly to one or more support members 41 aligned with one or more corresponding apertures 39 in container 11. A tubing portion, such as portion 13a depicted here, which is fixedly connected to separation container 11, disposed across the aperture 39 as shown, would then come into contact with the face 41a of support member 41. If the face 41a is inclined such as is shown here, then continued downward movement of separation container 11 will be facilitated by a downward, angular movement of the tubing portion 13a. Further assistance will occur if the tubing line is resilient, and thus may stretch some as shown and then resile back into its normal, substantially straight position as shown in FIG. 16C, where it becomes positioned in the valve 42. Other shapes of face 41a may assist in this sort of process as well, including reduced width and partially flat/partially angulated faces like those shown in FIGS. 8-15.

The clamp space 46 of valve(s) 42 may have a groove-shaped surface 48 (FIGS. 11, 16 and 17) and/or an otherwise open mouth area 47 which can be defined to open the valve space 46 inwardly toward the open inner compartment 52 toward the center of the rotor turntable 40 (as shown somewhat by the representation of FIGS. 7A and 7B), or the mouth 47 and the space 46 can open outwardly facing toward the outer circumference 38 of container 11 (not shown), or they can open perpendicularly thereto (as would be the case for cooperation with the tubing lines as positioned in the holes 39 of FIGS. 5 and 6), or at any other angle relative thereto (as shown for example in FIGS. 9-12, inter alia). The respective tubes 13, 15, and/or 25 (and/or 19) may then be inserted in one or more of the respective valve openings 46 (see FIGS. 7-10, 16 and 17) in connection with the mounting process as will be described in further detail below. The clamp mouths 47 may be triangularly (not shown) or rectangularly shaped (as shown) or have a slightly curvilinear edge portion defined in the opening (not shown) as well as in back at 48, which may result in essentially V-, U- or C-shaped or other shaped groove openings 46 formed between the clamp elements. As shown in FIG. 17, particularly FIG. 17C, movement of element 44 toward element 43 across space 46 can be achieved by movement of a shaft 49 on or against which element 44 can be in contact. A further rod 49a may also be used to contact and move shaft 49.

In several embodiments, the clamps 42 may also have energy wave, e.g. radio frequency (RF) or the like, welding and/or cutting capabilities to selectively weld and/or cut any plastic tubing lines disposed therein. Thus, in general (use) a tubing line could be either clamped, or clamped and welded, or clamped, welded and cut, depending upon the procedure selected. The energy wave would be made to emit from one clamping element, such as element 44 in FIG. 17C toward a receiving element 43. The power and/or energy may be transmitted by and/or through shaft 49 (and/or rod 49a or the like if used).

As introduced above, FIGS. 7-10 show views of the rotor turntable 40 having a separation set 10 arranged in/on the centrifuge rotor 40, and FIGS. 11-15 illustrate embodiments of an empty rotor 40. The rotor 40 is of a type whose separation space 50 comprises an annular separation compartment 51 and a central compartment 52, which are arranged concentrically with the rotary shaft 53 (FIGS. 11 and 15) of the rotor and communicate with each other through the valvular zone 54. The separation space is covered with an optional removable rotor cover 55 (see FIGS. 1C and 13; FIGS. 13A and 13B). As introduced above, centrally in the rotor turntable 40 there is a space 52 where one or more of the secondary, finished component containers 12 (plasma container), and 14 (RBC container) and optionally also 24 (platelet or buffy coat container) may be placed. In accommodating the two component embodiment shown in FIG. 2, or the three component embodiment of FIG. 3, the substantially cylindrical space 52 may by disposed in or adjacent the rotor shaft 53 which may thus define the central compartment 52, and is adapted to receive the first and/or second and/or third component container(s) 12, 14 and/or 24 which can be placed in this space before and may thus be useful during centrifugation. Note, in most embodiments such as those primarily described herein, central compartment 52 is substantially fixedly connected to shaft 53 and thus compartment 52 rotates therewith during centrifugation, as do any of the contents thereof including containers 12, 14 and/or 24.

Figure 1C:
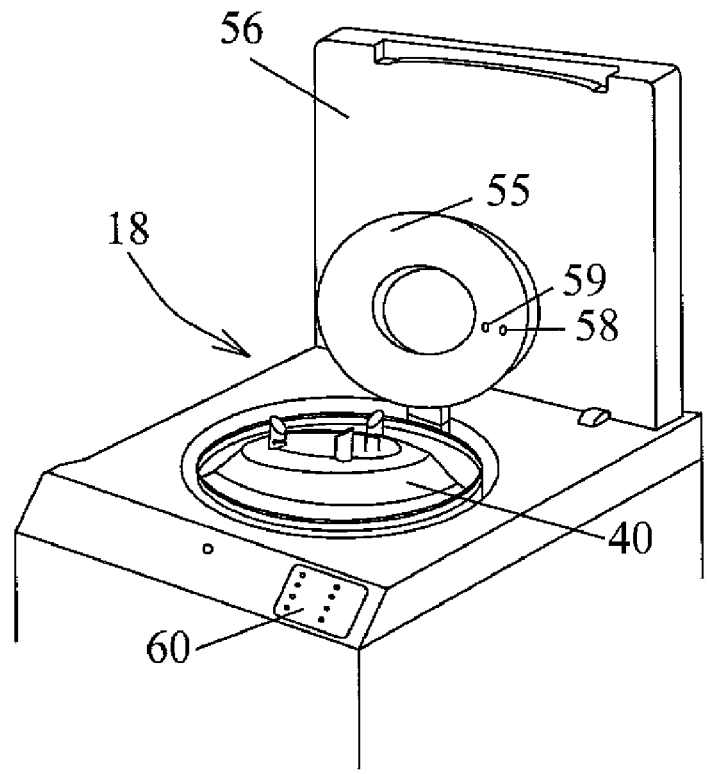

The rotor cover 55 may preferably be made of a transparent material to make it possible to monitor the movement of the separated layers by means of a human operator visually inspecting the interface (likely with the assistance of a strobe light and/or a camera, strobed or otherwise (none shown)) or by one or more sensors 58, 59 (two shown schematically in FIG. 1C) which may be mounted in the surrounding rotor turntable 40 and/or in the turntable cover 55 and/or alternatively in the relatively fixed stationary machine lid 56 (FIGS. 1A-1C). The sensors 58, 59, which can be photocells, are able to detect at least one characteristic of the fluid components (e.g. the color, the turbidity, etc.) in the separation container or in the lines connected thereto. The sensors are mounted in the turntable 40 or in the lid 55 of the turntable so as to face the pathways of the fluid components from the separation container 11 to the respective collection lines 13, 15, 25. Note, in a separation machine adapted to receive the separation container 11 represented in FIG. 5, only one sensor is needed, facing the bay area 30a between the distribution channel 45 and the annular chamber 11a. Note, depending upon placement thereof, the photocells 58, 59 inter alia may be used with or without a transparent material to monitor particular fluid flows. Other sensors (not shown) of other types could also be used and disposed in the housing and/or on the turntable 40. The photocells or other sensors may trip a switch or switches, or generate signals that communicate with and/or can be sent to the control unit 60 (represented schematically in FIG. 1 by the control panel identified with the numeral 60), which is correspondingly mounted in the casing or housing of machine 18. The respective tube valve(s) 42 and/or other features of the overall system as may be described may then be controlled by the control unit 60 The control unit 60 may include in one simple embodiment, an electro-magnet that switches a tube valve 42 to its closed position. In other embodiments, the control unit may include one or more electronic circuit control(s), processor(s) and/or microprocessor(s). It can, in particular, be connected to a memory of the separation machine in which various separation protocols (nature of the composite fluid to be separated, number and nature of the fluid components to be collected, spinning speed, spinning time before separation, etc.) may be stored. The control unit 60 can thus be of a computer nature to not only process the data it receives and not only issue control signals according to programmed or programmable instructions, it may also record data and communicate with other computer or computer-type devices.

Figure 14:
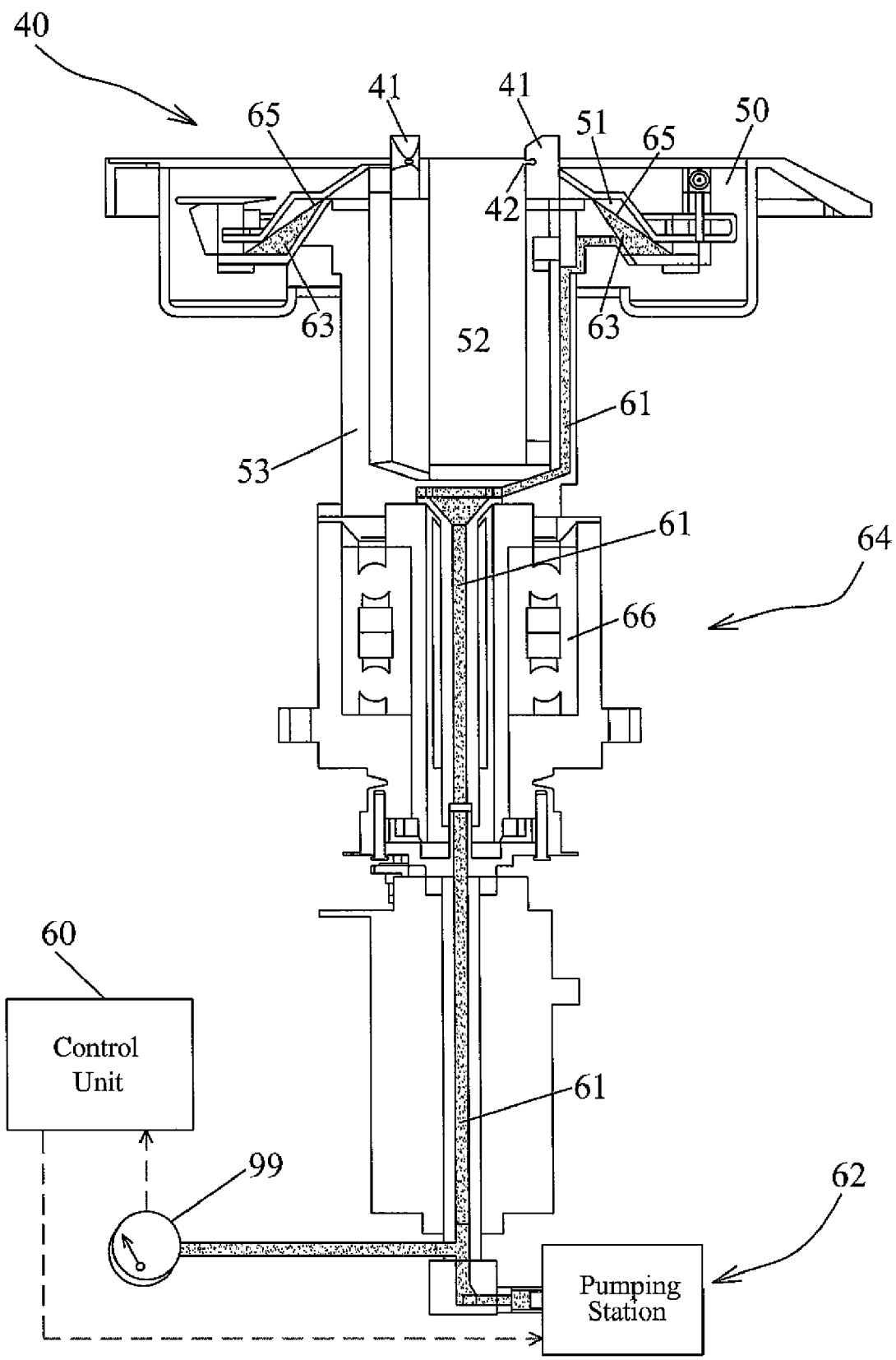
FIG. 14 is a sectional view of a rotor assembly of the present invention.

Moreover, the rotor turntable 40 preferably comprises means for squeezing the separation container 11, i.e. for reducing the volume of the separation compartment during rotation in order to displace or express a separated fraction or component product from the separation compartment 51 into its associated container or bag 12, 14 or 24 in the central compartment 52. In each of the 2/3 component embodiments illustrated in FIGS. 2 and 3, a pumping station 62 is used to decrease the volume of the separation compartment by pumping hydraulic fluid through a duct 61 as shown in FIGS. 14 and 15 in the rotor shaft 53 to an annular inflatable hydraulic chamber 63 which is delimited by a flexible diaphragm 65 secured to the rotor turntable 40. The hydraulic fluid may be pumped through a continuous duct 61 that passes through the centrifuge motor 64, around or along the side of the central chamber 52 and thence into the hydraulic chamber 63. A pressure sensor 99 is connected to the hydraulic circuit that fed the inflatable chamber 63. The pressure information from the pressure sensor 99 is provided to the control unit 60. The control unit 60 may be programmed to use the pressure information to stop the centrifuge and the pumping station 62 when the pressure detected reached a high-pressure threshold corresponding to the separation container 11 being empty. The control unit 60 may also control the pumping station 62 as a function of a comparison between the pressure sensed by the pressure sensor 99 and predetermined pressure thresholds stored in the memory of the separation machine, so as to adapt the flow rate at which the various fluid components are transferred from the separation container 11 into the collection containers 12, 14, 24. This is particularly important for fragile fluid components like red blood cells. FIG. 14 shows this schematically in a conically declining rotor turntable 40 embodiment wherein the separation chamber 51/hydraulic chamber 63 is shown approximately half-filled with hydraulic fluid under the diaphragm 65. In the alternative embodiment of FIG. 15A-15C, a substantially planar rotor turntable 40 embodiment is shown, wherein in FIG. 15A, the separation chamber 51/hydraulic chamber 63 is substantially half-filled (not unlike that shown in FIG. 14, though flat here); and FIGS. 15B and 15C show respectively only a very partially filled separation chamber 51/hydraulic chamber 63 and then an almost completely filled separation chamber 51/hydraulic chamber 63 under the diaphragm 65 as typically would be the respective conditions first at the beginning of an expression operation and then at the end of that process.

As shown also schematically in FIGS. 14 and 15A, one or more slip ring apparatuses 66 may be disposed in and/or around the centrifuge motor 64 to communicate power from a stationary power supply (not shown) through to the rotating rotor 40 and more particularly, to the elements on the rotating rotor 40 which want power for operation during centrifugal rotation. Amongst these may be the clamping valve devices 42 disposed in the rotor support members 41. Power may be supplied to these valves 42 during rotation for the mere clamping/valving function, or also to provide energy wave, e.g., radio frequency (RF) power for sealing and/or cutting any plastic tubing lines disposed therein, if desired. Moreover, power may be supplied to one or more photocells 58, 59 or any other sensors (not shown) disposed in and/or on the rotating rotor 40.

The functions and/or processes of various separation systems (machines 18 and bag sets 10) according to the present invention will now be described, first generally as applied to a composite or whole fluid with component parts, and then paying particular attention to the use of such a system for separating a whole blood donation/collection into component products. With general reference to FIG. 18, a fundamental process will first be described, with details and alternatives to be described below.

Figure 18A:
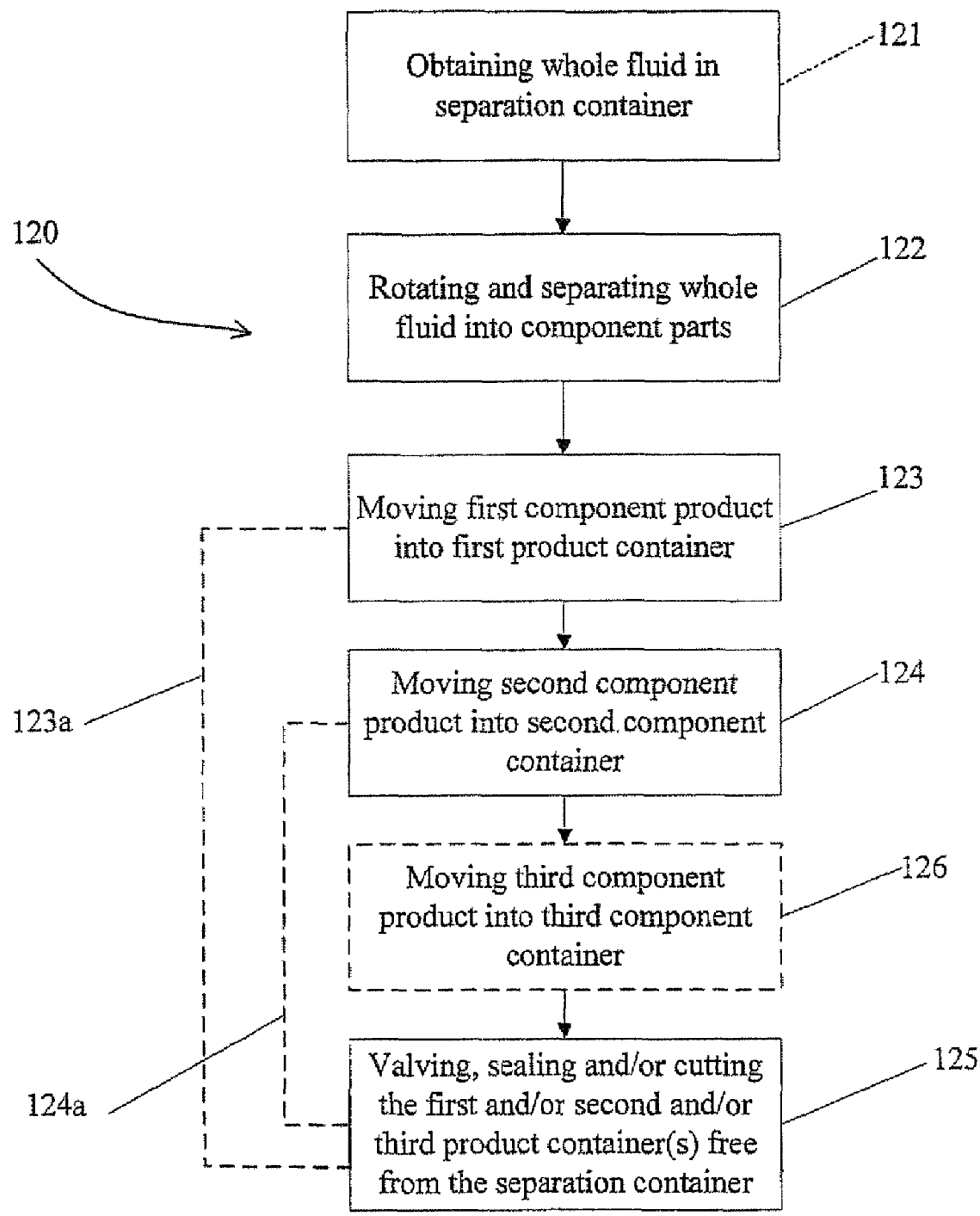
FIG. 18 includes sub-part FIGS. 18A and 18B which are flow charts depicting methods according to some alternative embodiments of the invention.
Figure 18B:
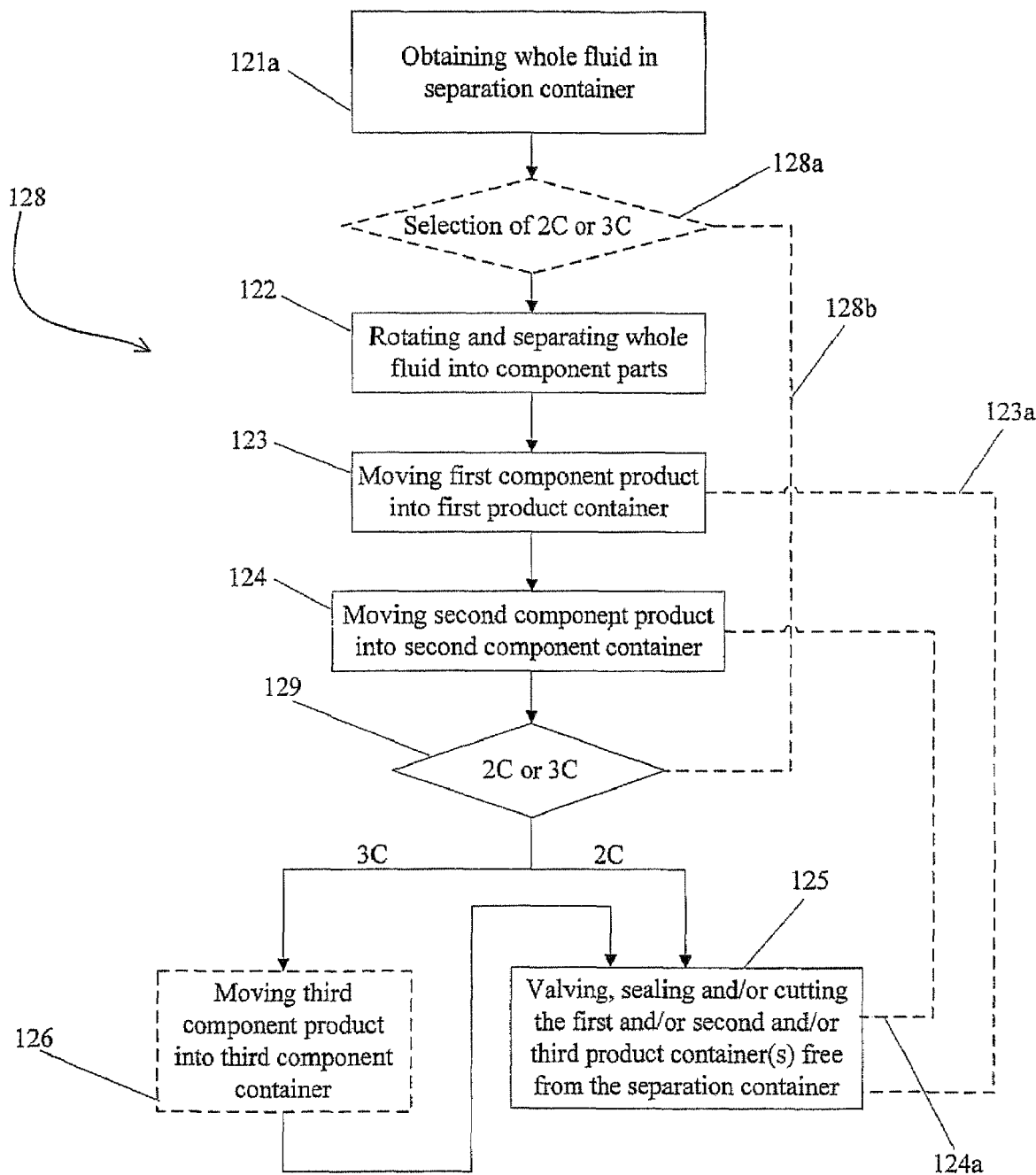

In a first step 121 of the general process 120 shown in FIG. 18 (both FIGS. 18A and 18B), the whole fluid, which is a composite of separable parts, is supplied to the separation container/bag 11. Then, in a second general step 122, the whole fluid is spun and the component parts thereby separated. Next, as shown in box 123, a first component product is moved or expressed out of the separation container 11 to a first product container 12. The second component product is also moved or expressed out of the separation container 11 to its second product container 14. This is depicted by box 124 in the process diagram 120. Lastly, the first and/or second component containers 12, 14 are closed off by valving, sealing and/or cutting the inlets, e.g., tubing lines, thereto. This is depicted by/in box 125. Note, as a general concept, the third, fourth and fifth steps 123, 124, and 125 may occur independently and/or after the cessation of the centrifugation and separation of the second step 122, or more generally here, the rotation/centrifugation of step 122 continues throughout the performance of the other steps 123, 124 and/or 125 and any alternatives and/or intermediary steps thereto. Thus, the rotation/centrifugation and separation step 122 will most often here, cease usually only after completion of steps 123, 124 and/or 125 and any intermediaries and/or alternatives thereto. Cessations of the second step 122 would then constitute the end of the usual process (note, unloading and/or other administrative-type handling processes, marking, labeling, storing and the like post centrifugation process steps, if performed post-processing, notwithstanding). Note, an alternative, optional process line 123a is also shown (in dashed lines) in FIG. 18A to emphasize the alternative that a valving, sealing and/or cutting step 125 may be performed relative to the first component container prior to or during the fourth step 124 and, in any event, prior to and separate from the valving, sealing and/or cutting step for the second product container.

Also shown in optional, dashed line form in FIG. 18A is an intermediate step 126 for the third product movement or expression from the separation container to the third product container. Note, an alternative, optional process line 124a is also shown (in dashed lines) in FIG. 18A to emphasize the alternative that a valving, sealing and/or cutting step 125 may be performed relative to the second component container prior to or during the intermediate optional step 126 and, in any event, prior to and separate from the valving, sealing and/or cutting step for the third product container.

An alternative flow diagram 18B is also shown in which an overall process 128 is shown further including a decision box 129 for the purpose of selecting between a two component (2C) process and a three component (3C) process. If a 2C process is selected, then the process avoids box 126 and goes right to step 125. A pair of dashed line representations 123a and 124a is shown for the purposes described above. Also shown is an optional decision box 128a in dashed lines early in the process flow to indicate the optionality of the choice by the operator generally occurring at or near the start of the procedure (note the alternative is that the decision, or at least its implementation may occur later in the process). A dashed line connection 128b between box 128a and 129 is shown to indicate the potential transfer of the selection data for use in the process flow at step 129 as may be the usual case. The first step here, 121a is indicating the loading of the set which could include the physical loading the set 10 into the rotor 40 and/or the loading of the composite fluid such as whole blood therein. These and other alternatives are described in further detail below.

Some important alternatives to this general process include but are not limited to the following. In the first step 121, the whole fluid is supplied to the separation container 11, however, this may include a fluid, such as whole blood which is first donated and/or collected indirectly to a separate initial collection bag 20, or may rather be directly supplied from the donor to the separation container 11. These alternatives were described above relative to FIGS. 2 and 3, as for example, where a separate un-attached, or alternatively a pre-attached whole blood collection bag 20 may be used for the initial whole blood donation/collection (using the needle 22 and the collection tube 21). Such a bag 20 may, after the collection, if previously separate and unattached, then be connected to the separation container 11. Blood would then be drawn from the bag 20 through a blood inlet tube 19 into the separation bag 11. Otherwise, the blood may be taken directly from a blood donor into the separation container 11 through the alternative collection line 21a and needle 22a. Typically, approximately 450 ml of blood would be collected during a whole blood donation. As mentioned, an anticoagulant may be simultaneously supplied or may have been supplied in advance to the bag 20 and/or the separation container 11. During donation/collection, the bag 20 or the entire separation set 10 (if pre-connected to bag 20 or if collection is direct into the round bag 11) may be placed in a rocking blood cradle as known in the art, to keep the blood in a mixed form. Thus, this first step 121 may include as part(s) thereof and/or prequels thereto, the donation/collection and/or transfer or mere supply to the separation container 11 of the whole fluid.

Then, after or potentially also as part of completion of this first step 121, the separate whole blood collection bag 20, if used, may optionally though preferably will be severed or otherwise disconnected from the set 10 (see disconnect 23a of FIG. 3). If not severed from set 10, then this bag 20 would likely have to be loaded within the rotor 40 with the rest of set 10.

The next consideration is when and/or how these initial step(s) may take place vis-à-vis the machine 18. Filling the separation container 11 may as mentioned occur directly from the donor, or may be filled from a separate container 20, but how these filling processes might take place has not yet been fully described. In one set of alternatives, gravity drainage (from either a donor or a separate bag 20) may be used to fill the bag 11. In such cases, the container 11 will usually need to be disposed at a location lower than the source of fluid (whether the donor or a discrete bag 20). Thus, the container 11 will not usually be disposed in/on the rotor 40 during these gravity filling operations; at least not with a donor, or not unless an arrangement such as might include a bag holding pole (sometimes referred to as an IV (intravenous) pole) (not shown) is set up so that the discrete bag 20 would be held above the separation container 11 which could then either simply dangle therefrom via tubing line 19, or be loaded initially empty in/on the rotor 40. Thus, the first step 121 can take place before, during or after loading of the set 10 and separation container 11 in/on rotor turntable 40. Thus also, the optional disconnection of the separate whole blood collection bag 20, if used, can also take place before, during or after the loading of the separation set 10 in/on the centrifuge rotor 40. As a next set of alternatives, the whole fluid or blood may be pumped (though not shown) from a bag 20 (or even from a donor) into separation bag 11. Such a pumping (though not shown) could also take place before, during or after the process of loading the bag set 10 in/on rotor 40.

Note, loading of the separation set 10 in/on the rotor 40 also includes loading the collection/end-product bags 12, 14 (and/or 24, if used) in operative position in the central compartment 52 as well as placing the annular or ring like bag 11 (simultaneously or prefatorily or subsequently) in operative position in the separation compartment 50 of rotor 40. The component container(s) 12, 14 and/or 24 may be placed in the central space 52 in the rotor shaft 53 and the respective tubes 13, 15 and/or 25 may be placed in respective grooves 48 in the clamping areas 46 of the respective support members 41 of the rotor 40. The optional rotor cover 55 may then be mounted or otherwise closed thereover, if used.

Then as introduced in FIG. 18 (18A and 18B) above, the whole fluid may be spun or centrifuged with the components thereof thereby separated as part of the second step 122. To accomplish this, the whole fluid may be disposed in a centrifuge rotor such as those rotors 40 described herein. Such a rotor 40 may then be started and the speed increased to a predetermined speed of operation. Separation may begin immediately and/or the spin may need to be continued for a period of time to achieve separation to a desired degree. This is an understood concept in centrifugal separation generally and may be dependent upon the characteristics of the fluid, the spin rate (e.g., rpm's) or other features such as the radial distance to be traveled by the separating component(s). Note, though usually the ring bag 11 will have been filled prior to centrifugation, in one alternative embodiment, the filling of the ring bag 11 may take place from a bag 20 (or even a donor (not shown)) not only before but also after the centrifugation has begun. In such a case, the bag 20 would likely be disposed in the central compartment 52 or a like chamber (not shown) in/on rotor 40 and fluid moved therefrom to the ring bag 11. Pumping may be necessary or desired, and/or the centrifugal forces may assist in such a fluid movement.

Then, when desired (as by pre-established timing, or by sensing of the desired degree of component separation), a movement of the separated component product(s) out of the separation container 11 may be initiated. This may be accomplished by beginning the filling of the hydraulic chamber 63 under the membrane 65 with hydraulic fluid as described relative to FIGS. 14 and 15 above. The hydraulic fluid, under pressure, consequently forces the blood component(s) to the nearest available outlet port. Note, this hydraulic fluid pressure/expression can be applied during continued centrifugation. The blood components are then expressed from the bag 11 by the filling of the hydraulic chamber 63. This occurs when the space in the separation compartment 51 of rotor 40, which is initially occupied by the blood component(s), may be automatically (or otherwise) filled by hydraulic fluid being forced from the hydraulic container or source 62 (not specifically shown) to the hydraulic chamber 63 via the duct 61. The blood component(s) are then forced out the respective outlet port(s). The hydraulic fluid preferably fills from the outward portion of the separation chamber inwardly as shown for example by the filling in FIGS. 15B and 15C. Filling from the outer portions inwardly may be resultant from the optional positioning of the hydraulic inlet at or near the external circumference of the rotor 40, or the hydraulic fluid being chosen having a specific weight (density) at least slightly greater than the heaviest component product being separated combined with the operation of the centrifuge forces thereon during introduction of the hydraulic fluid into the separation chamber. Note, though the examples of FIGS. 15B and 15C are in flat rotor embodiments, the principles are substantially the same for any of the conical embodiments as well. The blood-filled section 11a of the conical container 11 of FIGS. 7-14 may then retain a somewhat conical shape during centrifugation and during the component expression stage(s). As mentioned above, the conical shape of the container may be beneficial in reducing the sedimentation distance of a quantity of red blood cells in a quantity of blood, the sedimentation distance being limited by the radial extent to which the liquid may be moved, which in turn results in rapid separation and relatively small interfaces between the separated layers.

As mentioned, separation may occur very quickly, even virtually immediately, or it may take a period of time. After such a period of time (dependent or selectable based on various parameters, such as the densities of fluid components and/or the rotational speed(s) used in centrifugation) the separation may then be completed. However, in most embodiments herein, the rotor turntable 40 will preferably be continued to be rotated to maintain the separation. In blood, the first component having the lowest specific weight, e.g., plasma, will lie in a circular layer closest to the radial central area or inner circumference, then the intermediate weight layer, e.g., buffy coat/platelets, will lie in an intermediate layer, and furthest away from the center will be the heaviest weight components, in blood, the red blood cells. Note, alternatives exist for the relative speed(s) of rotation of the rotor turntable 40. For example, relatively high speeds, for example on the order of 2500-3500 (typically around 3000 or 3200) revolutions per minute (rpm's) may provide a sort of "hard" spin which will quickly force the settling out or sedimentation of heavier weight components (e.g., RBCs from the lighter weight materials (e.g., plasma). Such quickness/speed in separation can be desirable due to shorter overall processing times, however, relative "hard" spins can also force the intermediate layer(s) (e.g., the buffy coat and/or platelets) to pack heavily or tightly against the RBC interface. Such hard packed intermediate components may thus be difficult to separate into a discrete product from the heavier components during a normal expression. In 2C examples, this may not be a problem, the buffy coat and/or platelets previously or postfiltered from the composite fluid, leaving only plasma and RBCs to be processed/separated and collected in containers 12, 14, as fast as possible. However, during many 3C (three component) processes, a "softer" spin may rather be selected on the order of for example less than 2000 or 2500 rpms (for example 1500 or 2000 rpm's). In such cases, the intermediate product, platelets or perhaps more often, the buffy coat may be separated during a first spin rate which may not be as hard as that described above, and thus the platelets/buffy coat may favorably be affected to only a small overall extent and may be mixed to a minimum extent with the neighboring layers during the displacement of those other components to the central section of the separation rotor. Such a softer spin rate may be used for the entire process of initial separation and then expression of the three components consecutively. Note, a softer spin rate may also be used to collect a 2C platelet rich plasma (PRP and RBCs, the PRP potentially being processed separately (by pooling of the like) to capture separate plasma (platelet poor, i.e., PPP) and platelets.

Otherwise, as an example of one alternative process herein, a charge of whole blood disposed within a round, annular separation container or bag in a centrifuge may be spun at two or more different speeds, e.g., a first rotational speed, e.g., 3200 rpm's. Then, after a period of centrifugal separation at this first rotational speed, yet while the rotation is maintained at this first speed, a selected valve may be opened by the system and a flow of a first separated component such as, for example, plasma, may be started out of the round annular container through a connecting tube to a first component container which may be residing in a central compartment of the centrifuge. A substantial amount, though perhaps not all of the first component will be moved out of the separation container to the product container. As this product is a result of a first relative hard spin, it will be substantially pure, platelet poor plasma (PPP).

Then, according to an embodiment of the present invention, one or more selected valves may be opened and closed to consecutively provide for expressing a second component product, e.g., a buffy coat or the red blood cells (with the buffy coat therein or filtered or to be filtered therefrom) in a two component process, to a second container, or if in three component mode, then the third component may be moved to a third component container. However, according to the two or more speeds embodiment(s) of the present invention, after the expression of the first component product, a second, slower rotational speed may be imparted on the centrifuge rotor and the annular separation bag before expression of the second component. This slower speed may then coact with the momentum of the remaining second and third component products to strip the previously settled second component, such as a buffy coat/platelet product, off the interface with the third component layer, for example a red blood cell layer, to re-suspend the second component, e.g., platelets, in a remainder portion of the first component, e.g., plasma. Coriolis forces may be involved (though not necessarily) in this process of stripping and re-suspending the second component. Then, after a period of second component or platelet re-suspension (and third component, e.g., RBC, re-settling out of suspension, if any), but also during continued rotation, the suspended second product, e.g., platelet fluid suspension, may be pressed out of the separation container into a second product, e.g., platelet product container. After this, the third product remainder, e.g., the red blood cell (RBC) remainder, may be moved or expressed into a separate third product, e.g., RBC, product container. The end product containers may then be valved closed and/or sealed off by the system during or after centrifugation, and then, upon stoppage of the centrifugal rotation, the discrete plasma, platelet and RBC product containers may be separately removed from the central portion of the centrifugal chamber.

In reference to FIG. 18A, these alternative speed steps may occur as follows. First, in the single rotational speed examples, the single rotational speed is achieved as part of step 122 and maintained throughout steps 123, 124 and/or 125. In a two-speed example, the first speed would again be attained in step 122 and maintained through step 123. Then, between steps 123 and 124, the second, slower speed would be established, with consequent re-mixing, re-suspending and partial (i.e., RBC) re-settling occurring at least mostly prior to the second component movement expression step 124. Then, this second speed may be maintained to the end of the procedure, e.g., through a third component expression step, if any; or, a further alternative third speed may be selected and used after the second expression step.

In reference to the third and fourth steps 123, 124, further detailed optional steps may include switching of the hydraulic system so that the hydraulic pump (not shown) is started while the rotor 40 continues to spin. One thought or consideration on selection of speed of rotation is that the centrifuge would preferably continue to be spun at a speed that provides sufficient centrifugal force to hold the components separate. Hydraulic fluid may then be pumped into the hydraulic chamber 63 under the diaphragm 65 in compartment 51. The volume of the composite or whole fluid separation compartment 51 is then reduced and the separated component fluid products are forced to flow towards the center of rotation. Plasma may then be the first component of step 123 displaced first from the separation section 11a of the separation chamber 11 and further out through the tube 13 to the plasma container 12 (see e.g. FIGS. 2 and 3). During this first step 122, i.e., while the plasma fills the plasma container 12, the platelet/buffy coat layer continues to move radially more and more inwardly towards the center of rotation and also toward the central areas 11b and 11c of the separation container 11. This movement may preferably take place uniformly from all radial directions (as uniformly forced by the hydraulic fluid) and yet also against the prevailing centrifugal force field. This coaction of the uniform displacement of the hydraulic fluid coupled with the prevailing centrifugal force field provides for the intermediate layer, the buffy coat/platelet layer to remain substantially if not completely intact and reduces the undesirable re-mixing thereof with either of the adjoining layers. Then, the next step 124 may occur, e.g., movement of the second component, e.g., platelets (or buffy coat) out of the separation container 11.

Note, alternative means may also be available to force the flow of fluid such as by pumping or providing a vacuum or suction.

The expression movement of the component products can be monitored by means of the photocell 58 and/or by the photocell 59 positioned in the rotor cover 55 or otherwise disposed in the rotor 40 relative thereto. The photocell(s) may be positioned adjacent the round bag 11 to sense the interface approaching the exit port(s). Alternatively, one or more of the photocell(s) may be disposed adjacent one or more of the tubing lines, or internal separation bag flow channels (e.g., channel 45) to sense when an interface between adjacent products has reached a maximum desired flow point.

Appropriate switching and/or signals may be generated by the photocell(s) such that the control unit or control system 60 can control the flow by controlling the pumping of hydraulic fluid which can be stopped or sufficiently slowed when the buffy coat layer is moved to be positioned near the area of the plasma outlet port 30. And then the platelet/buffy coat interface with the plasma layer is thus disposed near the central area 11c of the separation container 11. The control unit 60 may then also close the tube valve 42 associated with the plasma tube 13.

The centrifuge may in one embodiment then be braked to come to a stop, and if only a single component is to be taken, the lid of the rotor turntable 40 may then be opened and the single component bag 12 or 14 (or 24) of and/or the entire separation set 10 removed. For example, the plasma product could be removed, and the buffy coat and/or red blood cells handled separately herefrom in a fashion either like some of those described here or not unlike others known in the art. The single component, here e.g., plasma, container 12 may either have been separated using the cutting and/or welding functions of the energy wave (e.g., RF) welder option(s) in a valve support member 42/41 or be separated from the separation set after and/or during removal from the bag 12 from the rotor 40 by means of a tube-welding/cutting gun. Note, this or any cutting by means of a welding function (e.g., energy wave or RF welding/cutting) built into valve/support member in 42/41 may be automated and thus performed by the machine (control unit 60), or could be manually performed/operated as well.

Otherwise, processing could alternatively continue from the point where the plasma tube 13 was valved or pinched closed by the corresponding valve 42. In a two-component embodiment, the valve 42 associated with the red blood cell line 15 could then be opened typically by the system (e.g., control system 60) on the interface detection by the photocell (s). The opening and closing of these valves may be substantially simultaneous may occur sequentially with a period of time therebetween. Continued or renewed hydraulic fluid pressure may be used to force flow of RBCs out of the ring container 11 into the RBC container 14 through the tube 15. This could continue until bag 11 is emptied (at least substantially emptied of the RBCs) and then the clamp 42 associated with the RBC line 15 can be shut, typically by the control system 60, and if enabled, a welding and/or cutting function in that clamp 42 can be activated to seal and cut line 15. If separate, and not previously loaded in bag 14, the seal (as by a breaking pin or a pressure rupturable seal (neither directly shown)) may be broken such that the storage liquid 16 may flow or be made to flow from the container 26 through the tube 27 to the RBC container 14 and be mixed with the red blood cell concentrate. The separation set 10 can then (or prior to the movement of the storage fluid 16 thereto) be removed from the rotor 40. Post-processing leukoreduction filtration could be performed at this point, such that the now diluted and somewhat less viscous concentrate of red blood cells can flow down into a further component container (see FIG. 3). If not done earlier, e.g., by the valve/support member 42/41 in the rotor turntable 40 (automated or manually), container 14 may then be separated from the set 10 by the tube 15 being welded together and cut by means of a tube welding/cutting gun. The plasma and the red blood cells may thus have been isolated in separate component containers. The separation set 10 having now been removed, the rotor turntable 40 may then be available for use with a new set 10 of bags 11, 12, 14. In such a two component embodiment, the buffy coat fraction may have been pre-filtered from the whole blood or may be caught in the RBCs (or plasma) to be in-line or post-process filtered therefrom, or may have remained in the separation container 11 (when an elongated RBC exit port 31 (see FIG. 7B) or the like may have been used, and thereby be available for further processing for recovery of valuable blood component products such as platelets and/or white blood cells. For instance, buffy coat fractions from several separations can be combined and centrifuged for recovery of a thrombocyte (platelet) cell suspension as disclosed in WO 95/01842.

In a three component (3C) embodiment, here also after a substantial amount (if not all) of the first component has been removed, and the first component line 13 has been clamped/ valved shut (and/or welded and/or cut), then a second component may be removed from the separation container 11. However, usually before the RBCs are emptied from the separation container, the intermediate component would preferably be removed. In a simplified case, continuing with the same initial spin rate, then the valve 42 associated with the tubing line 25 of the intermediate component, here usually a buffy coat (continued same spin rate), would be opened again typically by the control system 60, and continued or renewed hydraulic fluid pressure may be used to force the flow of buffy coat (and/or platelets) out of the ring container 11 into the intermediate product (buffy coat/platelet) container through the tubing line 25. This would continue on either a manual control, a timing mechanism or until a photocell or cells or other sensors would note the appropriate movement/positioning of the interface of the intermediate component product with the RBCs. Then the clamp/valve 42 associated with line 25 of the intermediate component product would be clamped/ valved shut (and/or welded sealed and/or cut) and the clamp/ valve 42 associated with the red blood cell line 15 could then be opened typically by the system (e.g., control system 60). The opening and closing of these valves may be substantially simultaneous or may occur sequentially with a period of time therebetween. And, continued or renewed hydraulic fluid pressure may be used to force flow of RBCs out of the ring container 11 into the RBC container 14 through the tube 15. This could continue until bag 11 is emptied (at least substantially emptied of the RBCs) and then the clamp 42 associated with the RBC line 15 can be shut, typically by the control system 60, and if enabled, a welding and/or cutting function in that clamp 42 can be activated to seal and/or cut line 15. Such an embodiment could occur at one continuous rotational speed, thus under substantially continuous, substantially constant centrifugal forces.

However, in some preferred alternative embodiments, one or more separate spins or rates of rotation may be imparted on the rotating system. Thus, here a first spin or spin rate would be applied for the first separation and maintained during the first expression, then when a sufficient desired amount of the first product has been emptied from the separation container 11 (as noted by time, operator observation, or sensed by the appropriate photocell(s) or other sensors), then the first component line 13 will be clamped/valved shut (and/or welded and/or cut). Expression is also halted at this point in this embodiment by the halting of the hydraulic fluid pressurization. Then, before any other lines (e.g., lines 15 or 25) are opened, a second spin as imparted by a second centrifugal rotational rate is created, and in one embodiment, this second rate is substantially slower than the first rate. This may have the effect of re-suspending an intermediate product in a remainder portion of the first component product, which will then allow for the removal of such a second component from the separation container 11. Then at this second spin rate, the valve 42 associated with the tubing line 25 of the intermediate component, here usually a nicely re-suspended platelet product, would be opened (here also typically in response to control by the control system 60), and since the initial expression was discontinued, a renewed hydraulic fluid pressure may be used to now force the flow of platelets out of the ring container 11 into the intermediate product, platelet container through the tubing line 25. This would continue on either a manual control, a timing mechanism or preferably until a photocell or cells or other sensors would note the appropriate movement/positioning of the interface of the intermediate component product with the RBCs. Then the clamp/valve 42 associated with line 25 of the intermediate component product would be clamped/valved shut (and/or welded sealed and/or cut), and the valve/clamp 42 associated with the red blood cell line 15 could then be opened typically by the system (e.g., control system 60). The opening and closing of these last two valves may be substantially simultaneous or may occur sequentially with a period of time therebetween. And, then continued or renewed hydraulic fluid pressure may be used to force flow of RBCs out of the ring container 11 into the RBC container 14 through the tube 15. This could continue until bag 11 is emptied (at least substantially emptied of the RBCs) and then the clamp 42 associated with the RBC line 15 can be shut, typically by the control system 60, and if enabled, a welding and/or cutting function in that clamp 42 can be activated to seal and/or cut line 15. Such an embodiment could occur at two or more rotational speeds, However, it may be preferred to maintain at least some rotation on the system to thus subject the fluid components to some substantially continuous, though substantially non-constant centrifugal forces. This will assist in keeping the products substantially separate even though there will be some desirable re-mixing of the intermediate component with the first component remainder.

Note, in any of these 3C embodiments, if the storage solutions were not integrated or otherwise kept separate, and not previously loaded in the respective bags 14, 24, then the seals (as by a breaking pin 17 or a pressure rupturable seal (neither directly shown)) may be broken such that the respective storage liquids 16 for each of the respective products in the bags 14, 24 may flow or be made to flow from the respective containers 26 through the tubes 27 to the appropriate containers and be mixed with the second and third products, e.g., the buffy coat/platelets and the red blood cell concentrate. The separation set 10 can then (or prior to the movement of the storage fluids 16 thereto) be removed from the rotor 40. If not done earlier, containers 14 and 24 may then be separated by the tube 15 being welded/cut by means of a tube welding/cutting gun. Post-processing leukoreduction filtration of the red blood cells (and if substantially pure platelets are available in the second product) could be performed at this point, such that the now diluted and somewhat less viscous concentrates of red blood cells can flow down into a further component container (see FIG. 3). Post-processing of any buffy coat products could then also be performed, for example by pooling with a number of other buffy coats and then re-centrifuging these to obtain a substantially pure platelet product. This platelet or any of the platelet products produced hereby could then be leukoreduced using a platelet post-processing filter or the like. The plasma, platelets and the red blood cells may thus have been isolated in separate component containers. The separation set 10 having now been removed, the rotor 40 may then be available for use with a new set 10 of bags 11, 12, 14 and 24.

Figure 19:
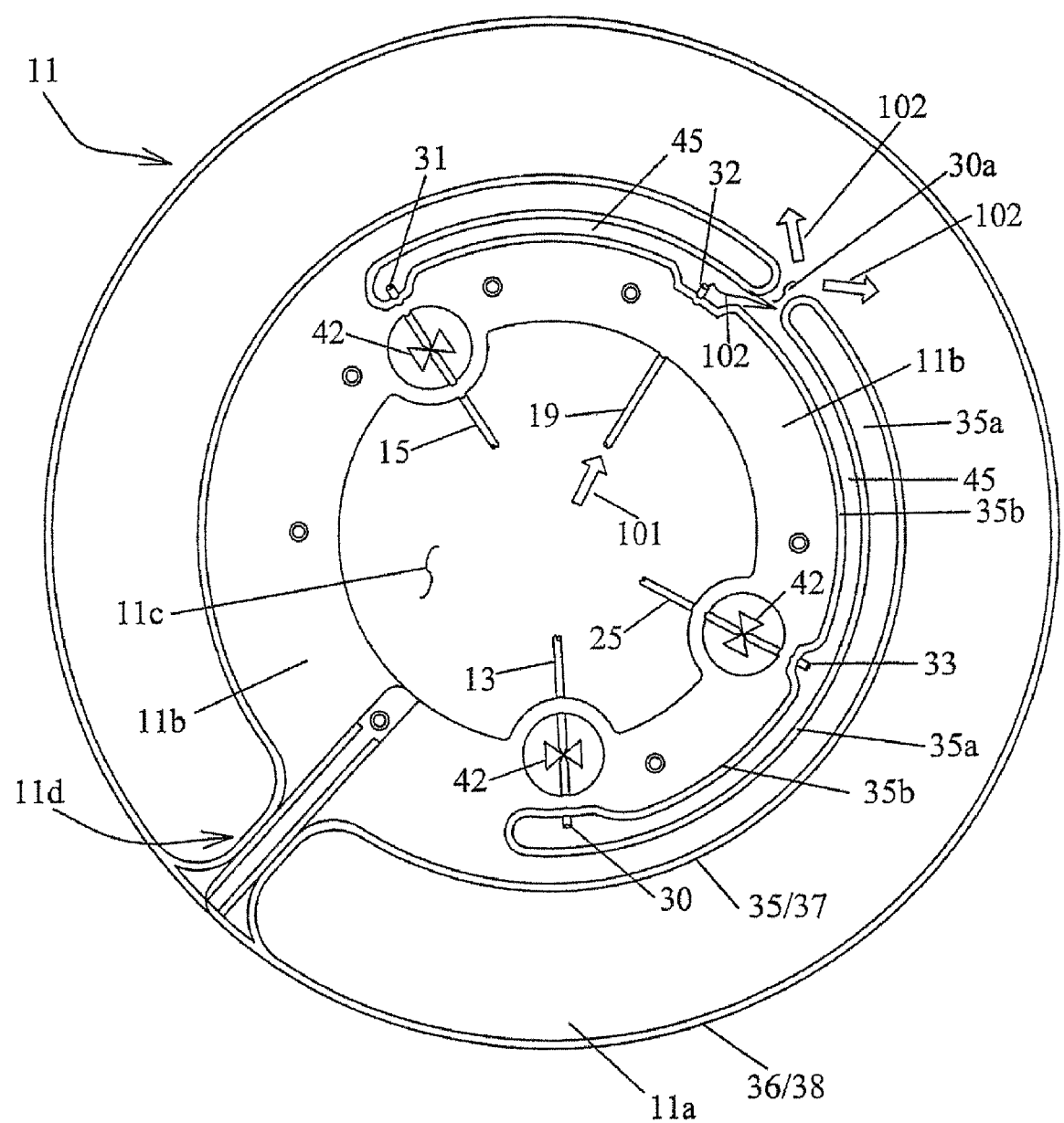
FIG. 19 is a flow diagram showing flow through the separation chamber.
Figure 20:
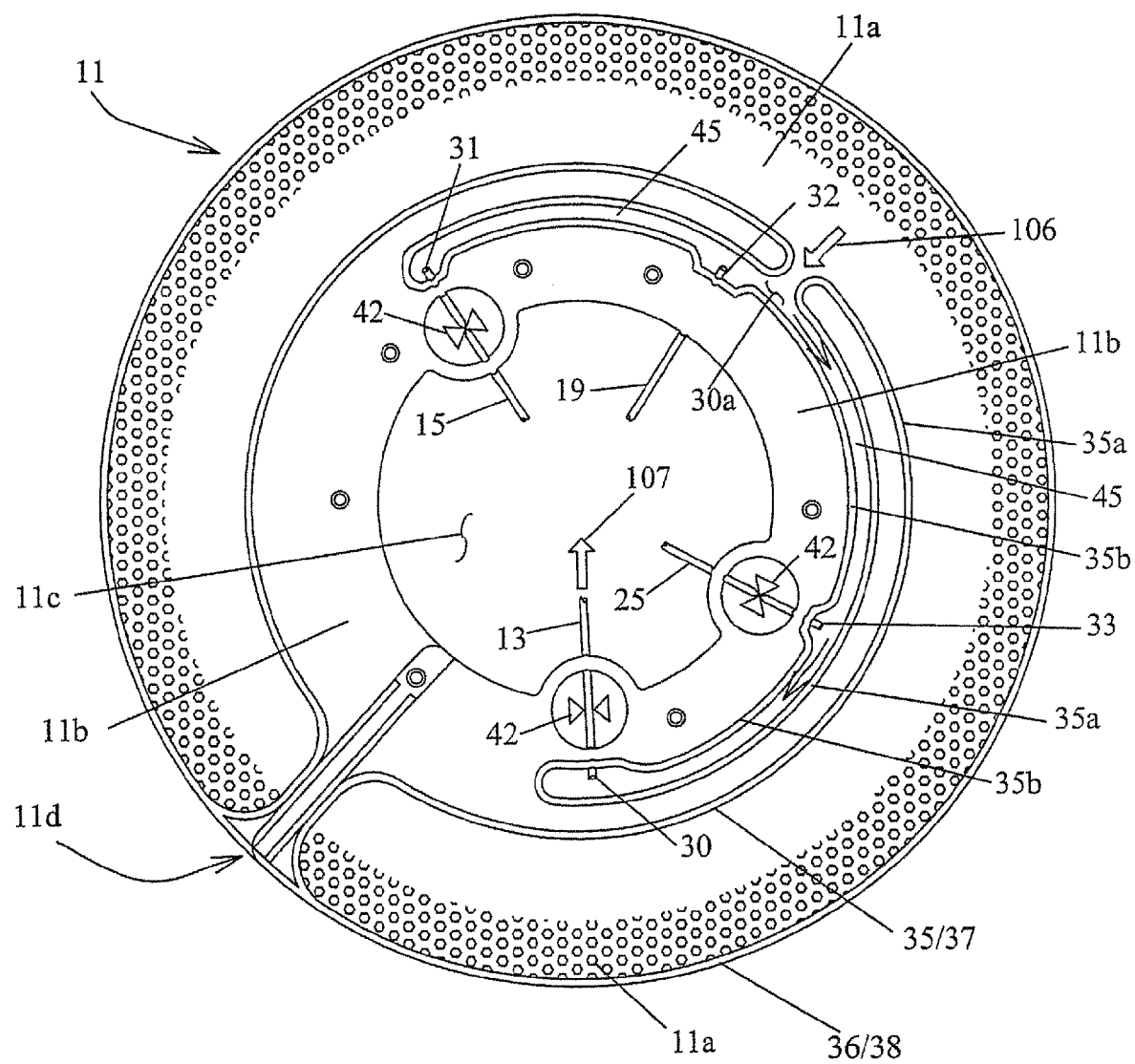
FIG. 20 is a flow diagram showing a further flow through the separation chamber.
Figure 21:
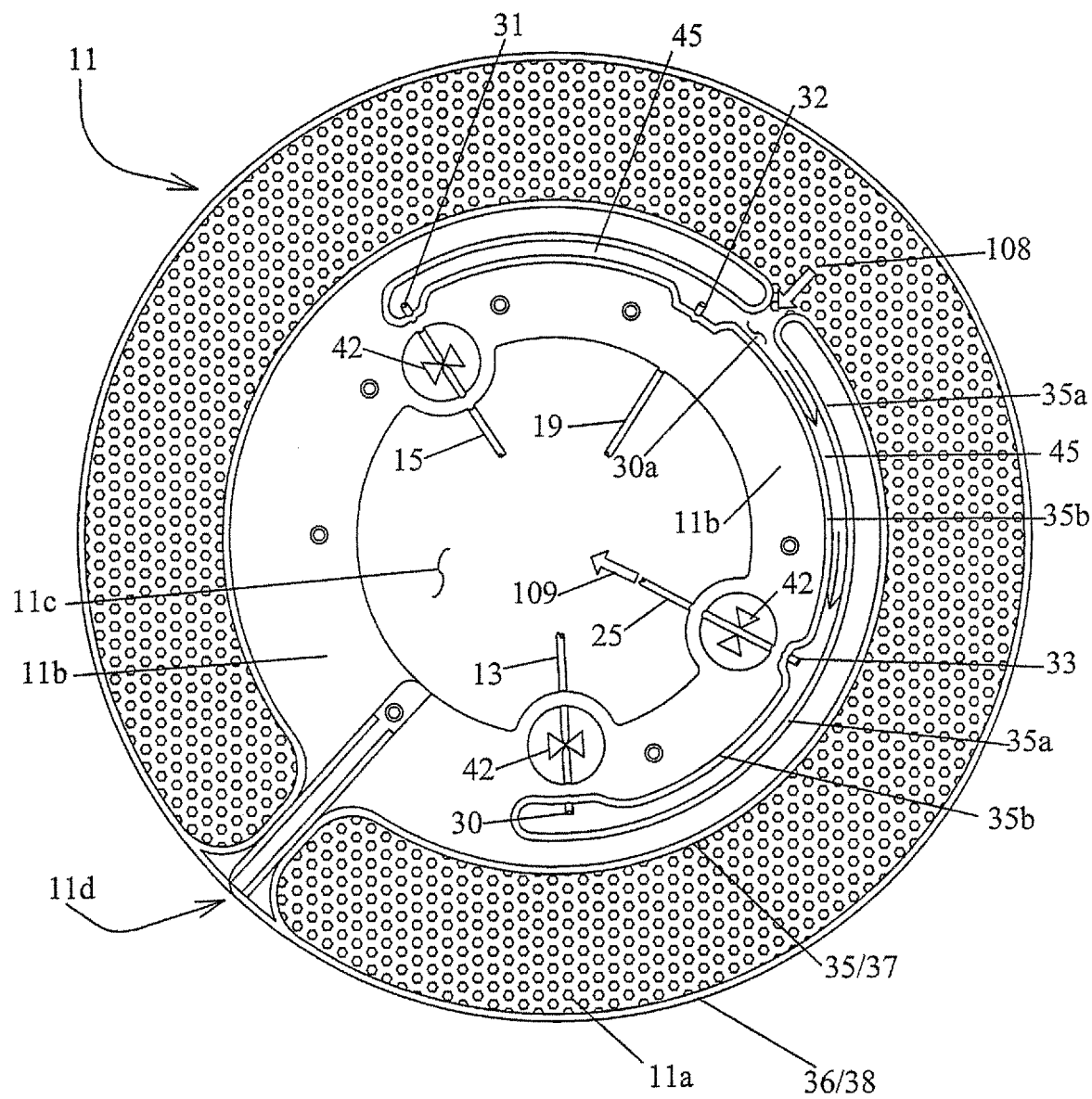
FIG. 21 is a flow diagram showing a still further flow through the separation chamber.
Figure 22:
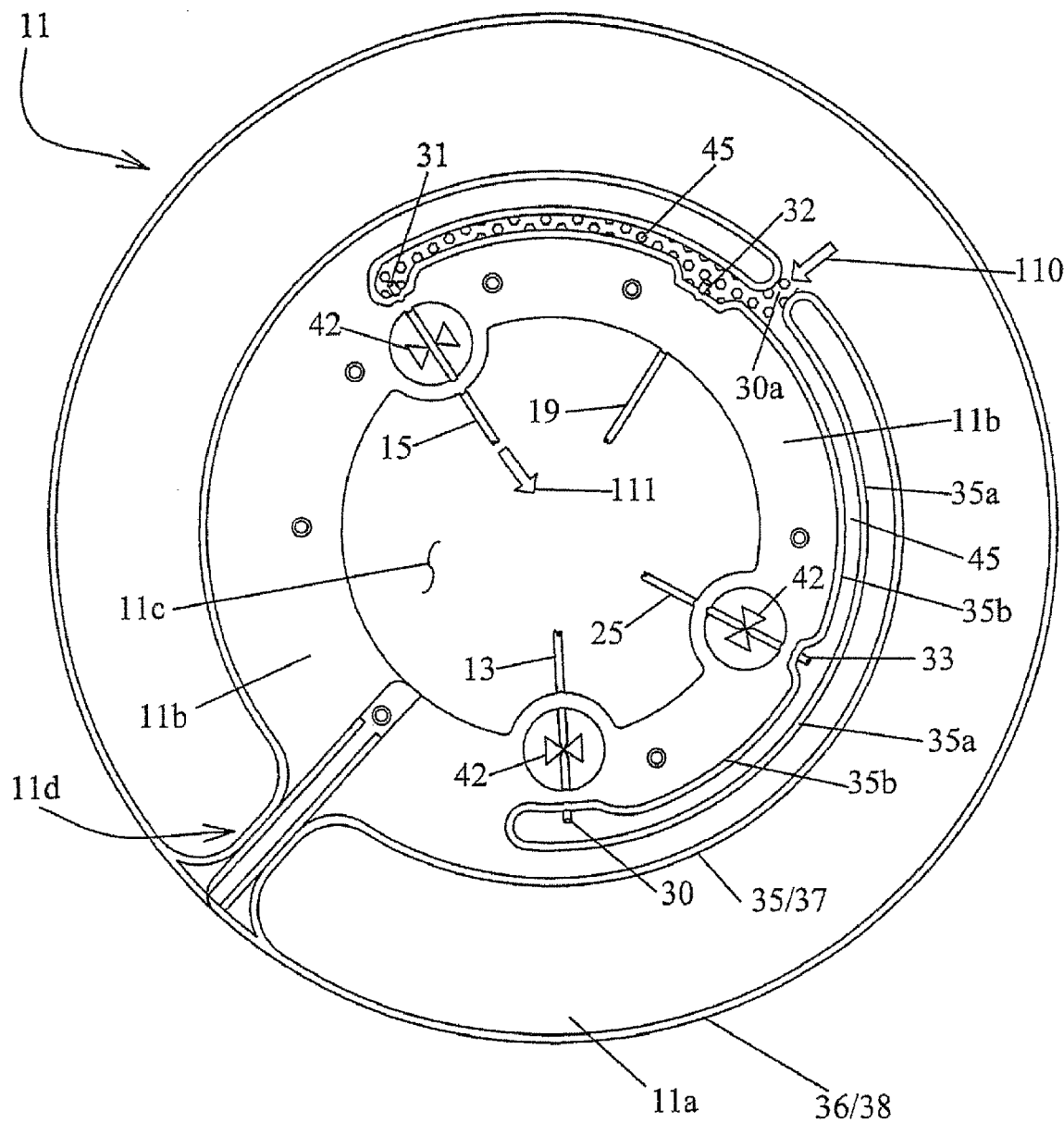
FIG. 22 is a flow diagram showing yet another flow through the separation chamber.

The respective flows in some of these embodiments may be better seen in the FIGS. 19-23. In FIG. 19, a separation container 11 is shown in which an inlet flow 101 is shown schematically entering/flossing through tubing line 19 toward and entering separation container 11. Actual entry is through port 32. In the shown embodiment, port 32 does not enter directly into the separation area 11a of container 11 (though it could). Rather, the inlet flow enters and flows (however briefly) in and through interior channel 45 of container 11. The inlet flow then flows through the open area 30a and passes to separation area 11a. Note, the schematically represented valves 42 shown operatively engaging each of the outlet tubing lines 13, 15 and 25 are all shown closed in FIG. 19. In FIG. 20, the fluid in separation area 11a is shown in a substantially separated form with the heavier elements, e.g., RBCs shown shaded adjacent the outer weld/outer circumference 36/38 while the clear area adjacent the inner weld/inner circumference 35/37 represents the lightest layer, e.g., plasma. The buffy coat/platelet intermediate layer is not separately shown. FIG. 20, thus represents the state of the materials in separation area 11a after a period of separation; and, also shown in FIG. 20 is then the next step wherein a valve 42 which is in operative relationship with the first component product tubing line 13 is shown opened (while the other valves 42 remain closed) and flow arrows 106 and 107 are shown indicating the flow of the first component, e.g. plasma out of the separation area 11a through the channel 45 and then out of the separation bag 11 through port 30 and tubing line 13. FIG. 21 shows what would be the typical next step or steps in either a two component process and/or a buffy coat or other intermediate phase collection. In FIG. 21, the valve 42 in operative association with first component line 13 is now closed, and the valve 42 in operative relation with the intermediate component line 25 is opened so that flow of intermediate phase materials, e.g. platelets/buffy coat may proceed from the separation area 11a into and through channel 45 to and out through port 33 and tubing line 25. Flow arrows 108 and 109 show this flow. Then, in FIG. 22, both of the valves 42 on lines 13 and 25 are closed and the valve 42 on line 15 is open so that the final product can flow from separation area 11a, through opening 30a, channel 45 and out through port 31 and tugging line 15 as shown by arrows 110 and 111.

Figure 23:
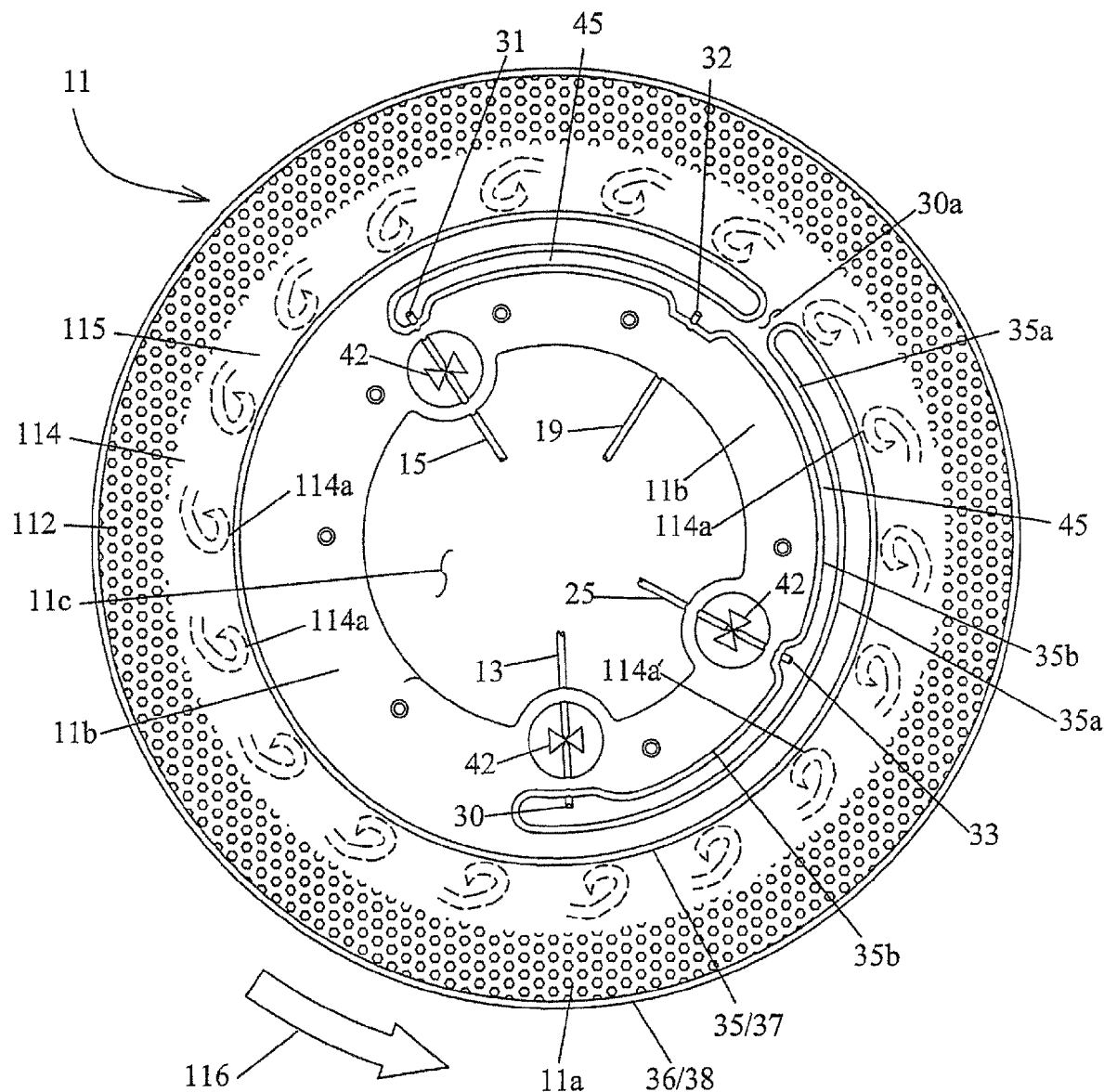
FIG. 23 is a flow diagram showing still yet another flow through the separation chamber.

In the alternative embodiment drawing of FIG. 23, an intermediate step of slowing the centrifugal rotational speed is shown. Here the heaviest phase product 112 is shown adjacent the outer circumference, the lightest phase product remainder 115 shown adjacent the inner circumference and the intermediate phase, e.g., platelets 114 being re-mixed by the coaction of the slowed spin rate with the momentum of the products within the separation area 11a. The deceleration rate at which the rotation speed is decreased is a selected so as to cause an optimal suspension of the third fluid component into the remaining portion of the first fluid component.

To this point, one or more rather generalized systems have been shown and described. Alternative specific systems will now be described in still more detail. Example systems are two component (2C) or three component (3C) systems for the separation and collection of respectively RBCs and Plasma (with a potential buffy coat remainder) and RBCs, platelets (or buffy coat) and plasma. In some embodiments, the initial collection may be into a separation container 11 or a discrete (pre-attached or non-pre-attached) whole blood bag 20 either of which optionally having an anticoagulant therein. Note, a discrete, separate WB bag 20 may, but need and may preferably not have any further ancillary bags or other devices attached thereto for the general reason of simplifying the collection process as described. Otherwise any standard whole blood (WB) kit as available on the market at this writing, could be used for initial collection, whether involving conventional three or four bag systems (in a 3 bag system, there is a whole blood collection bag and two component bags, typically destined to receive RBCs and plasma; while in a conventional 4 bag system, there is an additional bag for storage solution such as AS-3 for addition to the RBCs). In such systems, preferably after collection the whole blood and AS-3 (storage solution) containers will be sealed and the remainder bags removed therefrom (which may be discarded as not particularly useful for the processes described herein). And then, the whole blood container 20 may be connected as by sterile docking onto the 2C or 3C disposable set 10.

In some embodiments, a leukoreduction filter 70 (see FIGS. 2 and 3) for whole blood (in 2C processing, this could be platelet sacrificing while in 3C processing this would preferably be platelet sparing) filter can be used in a whole blood, pre-centrifugation, pre-processing filtration. Other filtration options (in-line and/or post-processing are discussed below. This may occur at the machine (with set 10 loaded) but maybe should be more preferably hanged away from the machine 18 so that there is less or no machine tie up. Gravity drainage then occurs through the whole blood filter 70 (platelet sacrificing; 6 to 8 minutes; platelet sparing similar timing, though perhaps faster because less selectivity necessary; compared, for example, to 12 to 30 minutes in the current manual process). Then the operator can seal and cut and thus disconnect the WB bag 20 and filter 70 (see disconnect 23a) from the set 10.

In a whole blood automated two-component (2C) process according to the present invention, the following are exemplary detailed steps in one preferred embodiment and approximate times for their execution:

| | |
|---|---|
| Load whole blood filled disposable separation container 11 | 30 seconds |
| Acceleration of centrifuge rotor 40 | 30 seconds |
| Sedimentation/Separation to 80 crit (hematocrit) | 60 seconds |
| Plasma expression (150 ml/min) | 90 seconds* |
| RBC expression (150 ml/min) | 90 seconds* |
| Deceleration of centrifuge rotor 40 | 40 seconds |
| RE welding (single seal) | 10 seconds |
| Unload products and disposable from rotor 40 | 30 seconds |

-continued

| | |
|---|---|
| Add Storage Solution: Sterile docking | 0.5 minutes |
| Spiking and filtering the added storage solution | 2 to 4 minutes |
| Total time per unit | 7.0-8.5 to 10.5 minutes. |

The asterisks (*) next to the plasma and RBC expression steps indicate that these times can be compared to 5 to 8 minute periods for conventional manual expression processes which leads to a comparison of 13.0 to 18.5 minutes automated using the present invention versus 17 to 38 minutes manual/conventional per unit of blood with leukoreduction.

A summary of features of the automated process includes the removal/reduction of the operator involvement; minimized rework (5 to 10%) due to issues such as inadvertent re-mixing; improved quality (consistency) and automated monitoring of process for quality (volumes, centrifuge stops, poor seals). In the presently described system, WB filtration is feasible with commercially available technology. Note also that although integrated solutions are available to be used herewith (see descriptions herein), they are not necessary.

In a further alternative whole blood automated three-component (3C) process, the following are exemplary more detailed steps in one preferred embodiment with approximate times for execution. A similar, alternative whole blood (WB) filtration (platelet sparing) could be performed pointing this example as well with an optional filter 70 in line 19 (FIG. 3). This pre-filtering and consequent filling of the round bag 11 offline (while not spinning in the centrifuge) may take approximately 6-8 minutes and could then be followed by loading the thus prefilled round bag into machine 18 (approx. 30 seconds). Then, the centrifugation can start by first accelerating the centrifuge 40 (30 seconds); followed by separation and/or sedimentation (sedimentation time: approximately, 60 sec., 80 Crit). Then the initial spin can result in (leukoreduced (LR) if pre-filtered) RBC and (LR) plasma (a further alternative is sedimentation to 90 Crit taking approximately 240 sec.). Then, various alternatives are available, as by expressing plasma (60 sec.) and expressing RBC (90 sec.) in either order, or simultaneously, however, this may need a radially outwardly disposed RBC outlet; thus leaving the buffy coat in the round bag 11.

Then the next step could be loading a PAS solution into the same round bag 11, probably including decelerating the centrifuge rotor 40 (e.g., to 1800 rpm (20 sec.)). Such a second spin (1800 RPM) with adding PAS (15 sec.) could be similar to a buffy coat process known and/or described before except for the continually spinning rotor here, with a sedimentation time of approx. 180 sec. In particular, the next step could be expressing additional LR plasma, and then expressing LR Platelets into bag 24 preferably with the PAS. (Note, bag 24 could have been the original container of PAS which solution was moved into the container 11.) Expressing platelets (90 sec.), expressing extra plasma (approx. 30 sec.), decelerating the centrifuge (30 sec.), RF welding (10 sec.), and unloading the set (30 sec.) may be the primary steps. Total process time may be approximately 10 to 12 minutes.

In addition, some alternatives for leukoreduction of the blood components include:

1) using whole blood filtration by filter 70 prior to separation of components (either platelet saving or platelet sacrificing, as described thus far);
2) using an in-line filter generally post-process (i.e., post-centrifugation), optionally pre-attached to the disposable set, likely with a separate final bag (see the phantom set with satellite bag 75, filter 76 and line 77 connected or connectable to bag 16 in FIG. 3) or a dockable post-process filter (not shown) to leukoreduce after component separation/processing;

3) using an in-line filter 72 (FIGS. 2 and 3, shown in phantom on line 15 could also be disposed on line 25 or even 13) or 74 (see FIG. 4B) that will leukoreduce during the separation process.

Thus, Leukoreduction of the component products of the present invention may also be easily performed in a variety of ways. In the embodiments generally described to this point, the whole blood may be leukoreduced prior to centrifugal separation using a whole blood leukoreduction filter. As introduced above, a platelet sparing leukoreduction filter may be used to allow for a greater recovery of platelets in a platelet product. Alternatively, a platelet-sacrificing filter could be used, and only two end products, i.e., plasma and RBCs, obtained. As a further alternative, leukoreduction filtration may be achieved after separation either in a conventional manner after removal of the end-product containers from the centrifugal system (e.g., by hanging for gravity drainage, or filtration may occur in the centrifugal system during the expression of respective products, e.g., platelets and/or RBCs (and/or plasma), from the centrifugal separation container 11. In such a case one or two (or more) leukoreduction filters may be used. For example, a single platelet and RBC sparing leukoreduction filter (see e.g., filter 74 of FIG. 4B) may be disposed in the flow path from the separation container to the end product containers. Platelets and RBCs (and possibly also plasma) may flow sequentially through such a single filter. Or, if two (or more) filters may be used, these may each be respectively disposed in separate exit flow paths (see filters 72, 73 of FIG. 3B) from the separation container 11 to the respective end product containers 14 and 24 (and potentially also 12). Thus, discrete distinct types of filters may be used for the respective products, e.g., platelets and RBCs. As a result, the present invention may thus provide highly pure plasma, red blood cells and/or platelets (or buffy coat) component products.

In certain in-line filtration options, the filtration may occur or be made to occur under pressure. As such the process of expressing a separated component product from the separation area 11a of container 11 may provide the pressure to push the component through an in-line filter. The hydraulic fluid is under pressure being pumped from its source 62, and being in virtual contact with the contents of container 11, separated only by the membrane 65 and the flexible container 11 wall, the pressure is communicable/communicated across the flexible membrane 65 and flexible wall of container 11. These pressure forces cause the movement of the fluid and thus cause the pushing of the fluid through the filter. As a first example is the optional in-line leukoreduction filter 72 on RBC outlet line 15 of FIGS. 2 and 3. Thus, during expression caused by the pressurized hydraulic fluid from source 62 pushing the component product(s) out of the separation container 11, also consequently pushes such component product(s), here RBCs through the in-line filter 72. Note, centrifugal forces may also affect the flow of fluid through such a filter during an on-line process.

Such in-line filtration may be amenable to one, two or three component processing. Thus, only one component may be filtered, e.g., RBCs (see FIG. 2), or both the RBCs and plasma in a two component example using for example the RBC filter 72 and a plasma filter (not shown). Or, two of three components could be filtered, e.g., RBCs and platelets each using e.g., the discrete filters 72 and 73 shown in FIG. 3. And, pressure could be applied during expression and continued centrifugation to push any or all of these fluids therethrough. In another example, see FIG. 4B, a single filter 74 for example, could be established for two or all three products. In such a case, the pressure could be applied to force first, the first component product, e.g., plasma, therethrough via port 30 and tubing line 13. Then, at the appropriate time, the valves will be switched so that the second component flowing behind the first component product will also flow out of chamber 11a through port 30, tubing line 13, filter 74 and then through branch connection 33a to and through outlet line 25. This could be the end of the process in a two component process, e.g. plasma and RBCs following therebehind, or this could represent the two end components of a three component process whereby the first component might be a plasma product not needing or otherwise decided as not being subjected to filtration and thus the other two components would be platelets and RBCs in either order though typically in the order of density, first platelets and then RBCs. Finally, in a three component process, typically first would be the lightest phase component, e.g., plasma, pushed through the filter 74, then the intermediate phase, e.g., platelets, and ultimately, the heaviest phase product, the RBCs. However, it should be noted that some leukoreduction filters may not be appropriate for such a situation in that they may not be platelet sparing, thus a platelet sparing filter would have to be used.

Moreover, different push through flow rates may have to be used, for example, the lower concentration light phase, low density types of components may be pushed through at fairly high rates of speed, whereas a heavier phase or a fraction more concentrated with component parts to be filtered may not be as efficiently filtered at high pressures or high flow rates. In a more particular example, the pressure and/or the flow rate may be controlled (e.g., by control system 60) to provide a relatively high flow rate (perhaps driven be a relatively high pressure) for the first component of a blood separation, e.g. plasma, out of the separation container 11 and through a potential filter (e.g., on line 13 or otherwise). Then, if in a two component process and leukoreduced RBCs are the goal, then, perhaps a somewhat lower pressure and/or speed may be desirable to filter all of the white blood cells and like buffy coat constituents therefrom. Note, it could be in some embodiments particularly depending upon the type of filter chosen, a rather higher pressure may be desired for the heavier phase RBC component, even though this may not result in a correspondingly high flow rate (i.e., the filter may slow the flow). However, if in a three component process, the more likely scenario may typically involve a slow, lower pressure expression for an intermediate phase material such as the platelets. This will be because of the substantially high concentration of white blood cells and like materials (i.e., white cell rich) in the intermediate phase that are desired to be filtered from the platelet product. A slower and/or lower pressure expression hereof may thus provide a more effective filtration of this product. Note, this second filtration with discrete filtration speed and/or pressure control could occur in pushing the product through a separate outlet line 25 (see e.g., FIG. 3), or through the same initial outlet line 13 and filter 73 as the plasma was (as shown e.g., in FIG. 4B). Then, in continuing this three component example, the RBCs could then be pressed out of the separation container 11 through a separate outlet line 15 and associated optional filter 72 (FIG. 2 or 3) or through the contiguous line 13, through filter 73 and then branch 31a and line 15 (FIG. 4B). Note, this third expression may be at a higher rate of flow and/or pressure than the platelet expression, and may as described in the two component example be as high, not as high or higher than that of the plasma expression. Here also, the pressure may be higher but the flow slower due potentially to packing in the filter. Note, if the same filter is used for two products, e.g., both platelets and RBCs, platelets and plasma, or all three, then a platelet sparing filter would preferably be used.

Note, optical controls may be used as e.g., from one or more photocell(s) 58, 59 in conjunction with the control system 60. Otherwise, other sensors may be used, as for example, pressure sensors sensing the pressure in the fluid flow or representative fluid chamber (e.g., sensing hydraulic fluid pressure as representative of pressure in hydraulic chamber 65 which is substantially the same as the pressure in the blood separation chamber 51, which is substantially the same as that in the respective outflow line 13, 15 or 25. Then, discrete different pressures might indicate the type of fluid flowing through a particular filter, and/or whether the applied hydraulic fluid pressure may need to be increased or decreased to better affect flow through the filter. For example, certain pressure indications for either platelet filtration or RBC filtration may indicate whether effective flow conditions (too fast or too slow) might be occurring, or whether for example there may be too much of a slow down indicating too much packing of material (such as platelets or RBCs) in the filter. Then, an appropriate corrective action, by flow and/or pressure control, may be performed.

Note also, the filters in an in-line situation may be different mechanically over conventional gravity filters. This may be desirable due either to the forced flow therethrough which may be at a pressure greater than gravity, and/or due to the higher forces experienced in a spinning centrifuge environment, there may be the equivalent of many G (gravitational) forces in the centrifugal force field depending mostly for example where along the radius the filter may be disposed. In some embodiments, it may therefore be desirable to have greater packing of filter material in the filter to counter the effects of the forced or pushed flow therethrough. Also, it may be desirable to strengthen the housing characteristics to avoid over pressures inside from breaking the housing. And, it may prove desirable to fix the filter in place inside the central compartment 52, perhaps at a minimum radial location away from the center of rotation, thus, lessening the centrifugal force impact on the filter body itself as well as on the filtration process. Note, it may further prove beneficial in an in-line filtration embodiment to have the filtration flow, i.e., the actual flow of filtering component product through the filtration medium, proceed from a radial outward inlet toward a radial inward outlet.

Figure 24:
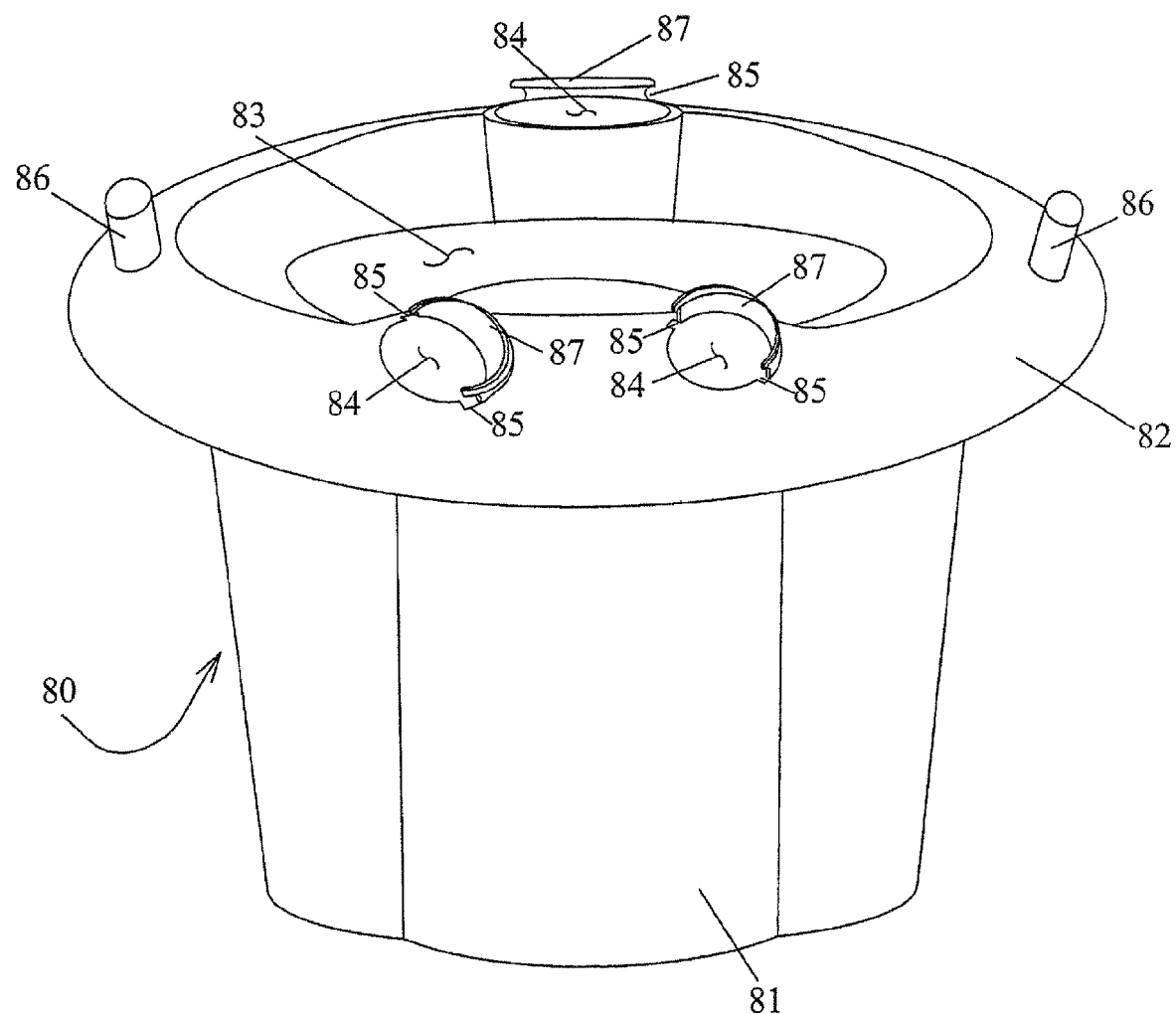
FIG. 24 is an isometric view of a separation set loading device according to one embodiment of the invention.
Figure 25:
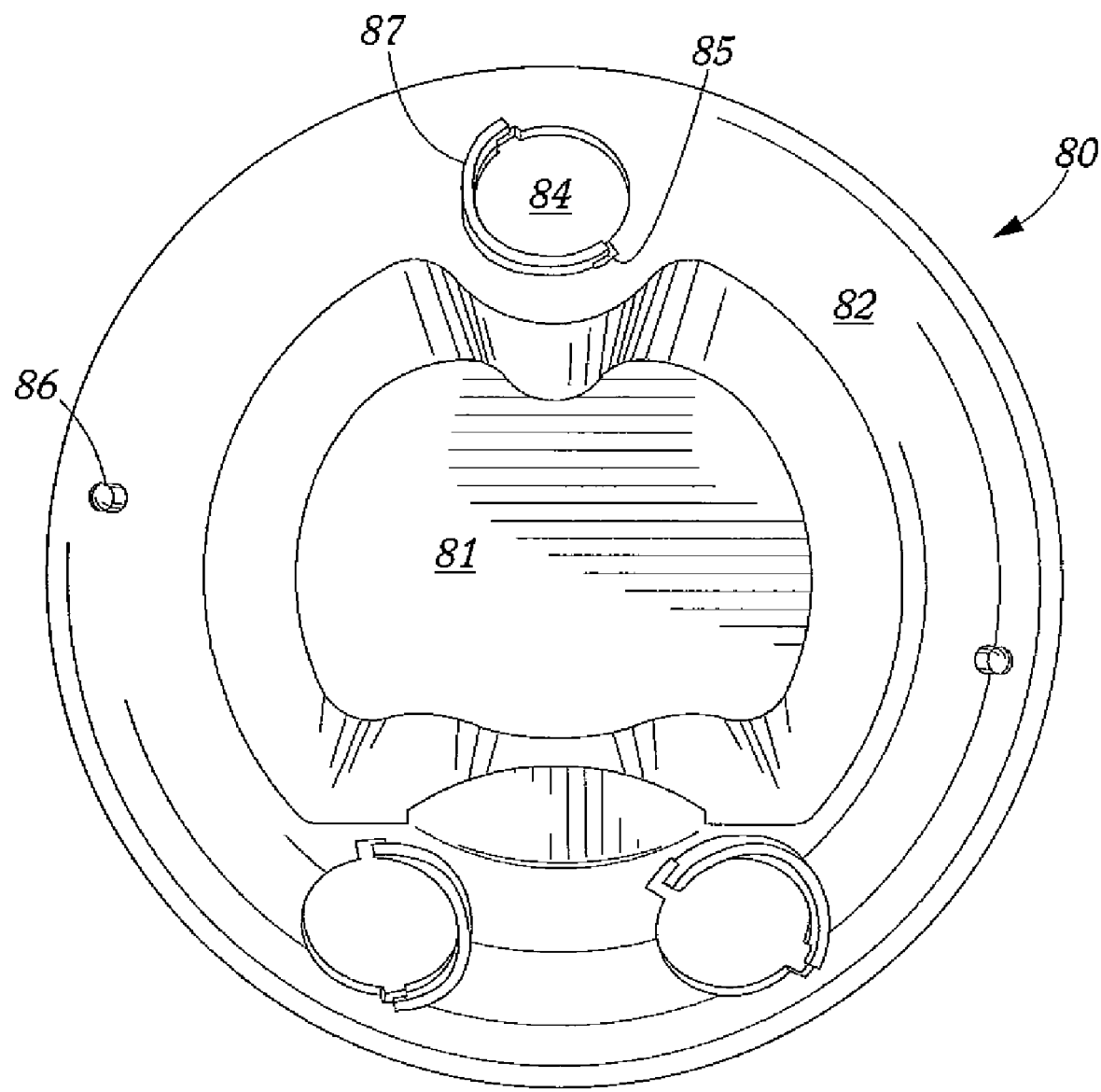
FIG. 25 is a top plan view of a separation set loading device according to an embodiment of the invention.
Figure 26:
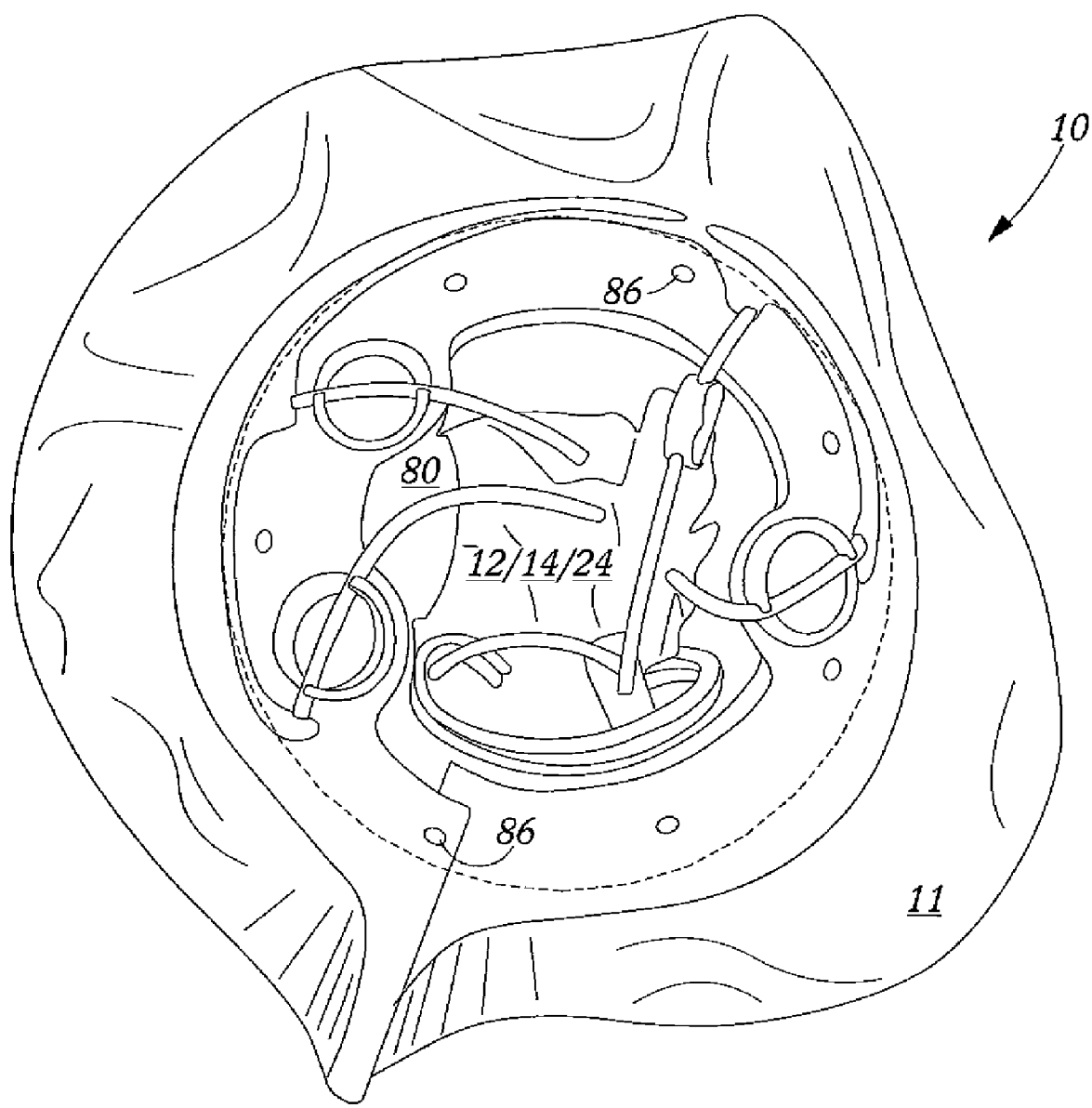
FIG. 26 is a top plan view of a ring-like separation container and separation set loaded in a loading device like those shown in FIGS. 24 and 25.
Figure 27:
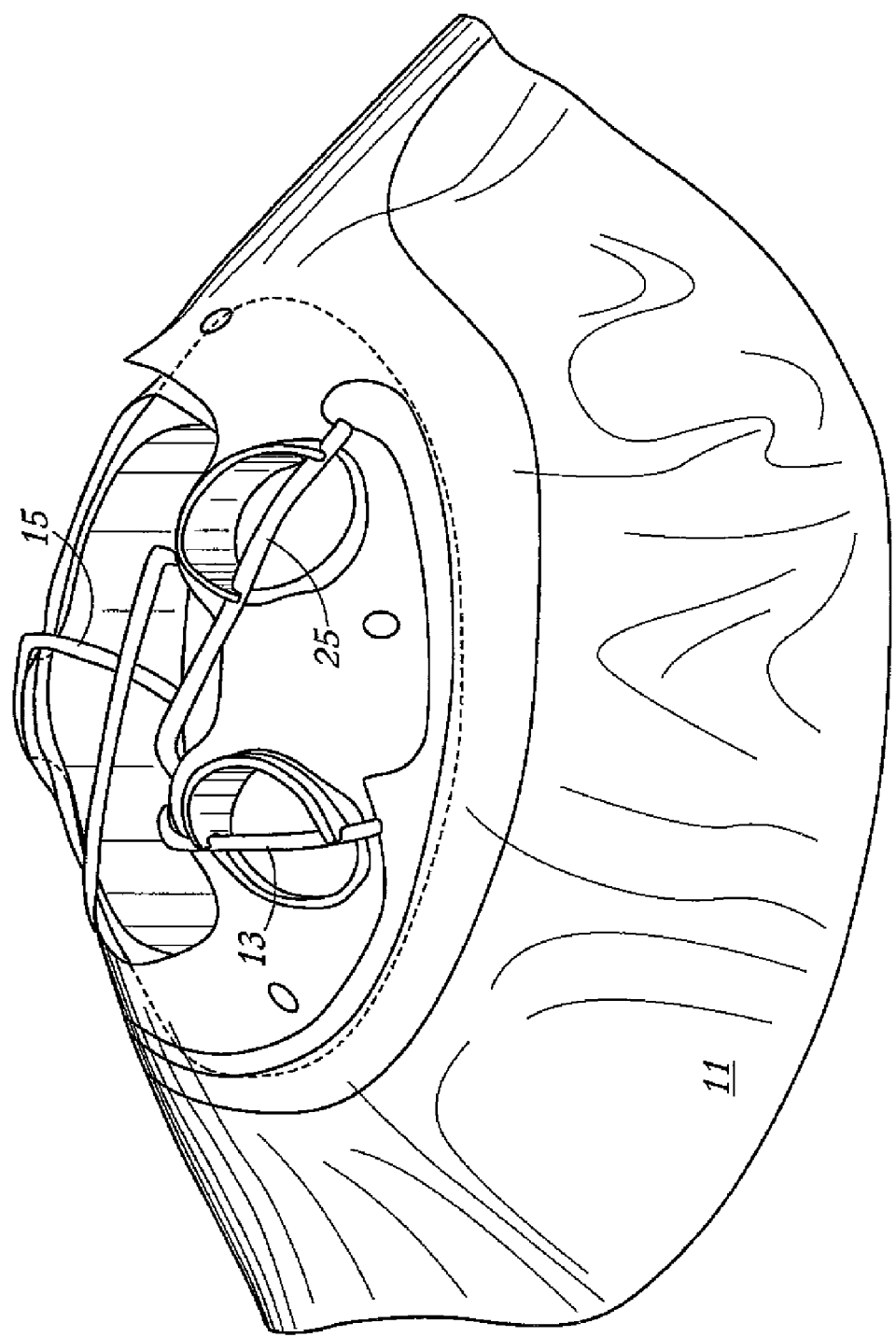
FIG. 27 is an isometric view, like that in FIG. 24, of a loading device in which a set like that in FIG. 26 is mounted.
Figure 28:
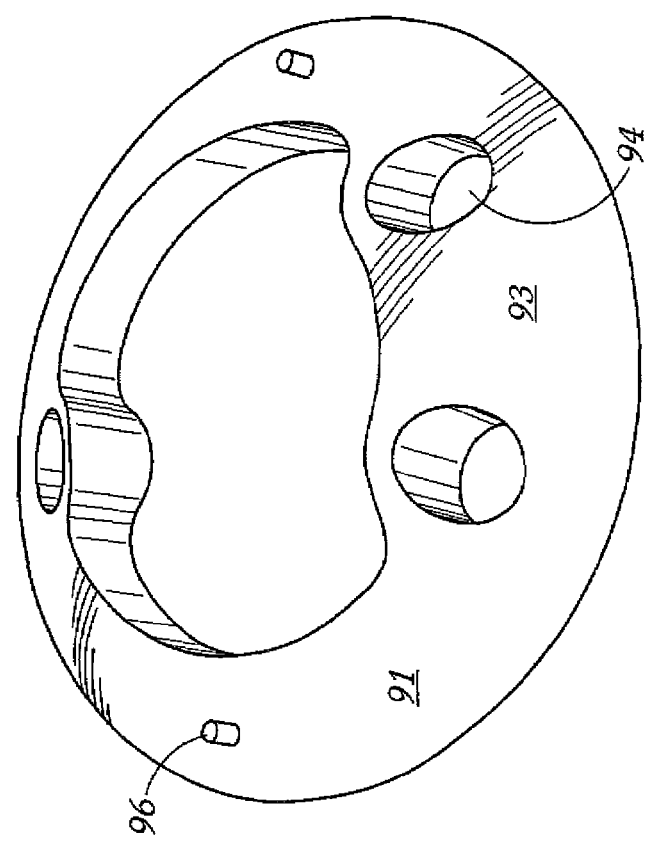
FIG. 28 is an isometric view of two other embodiments of separation set loading devices according to the present invention.
Figure 28:
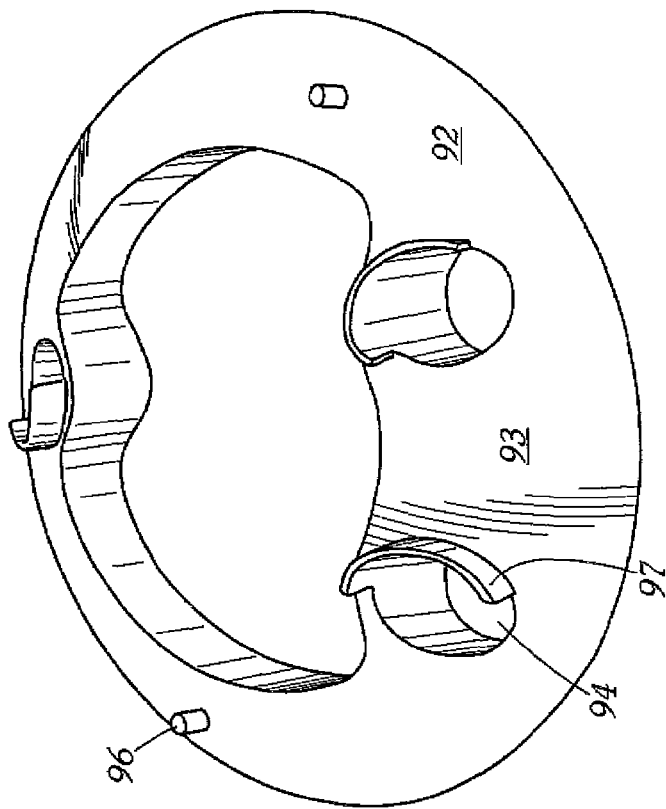
Figure 29:
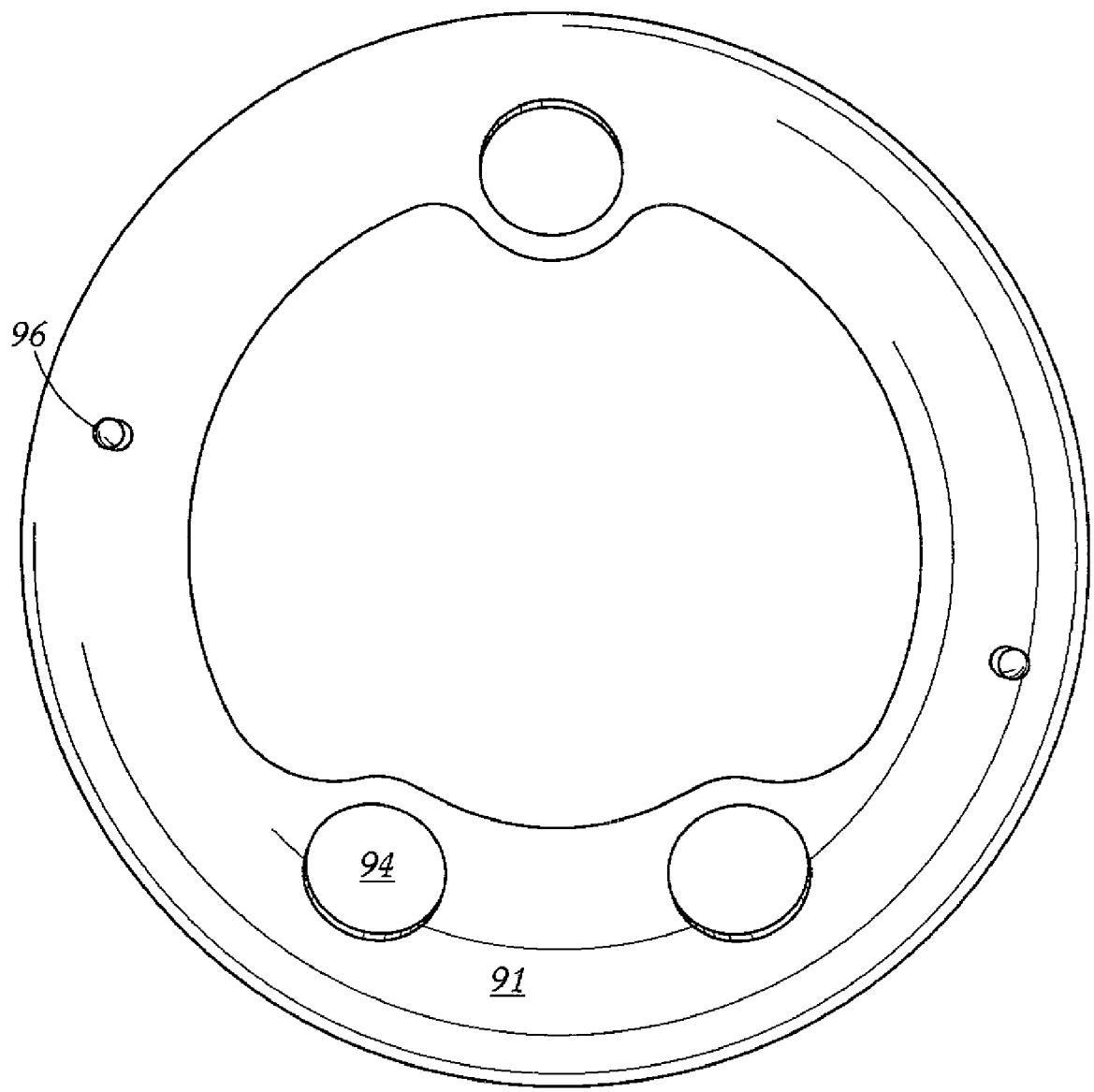
FIG. 29 is a plan view of a separation set loading device according to the present invention.
Figure 30:
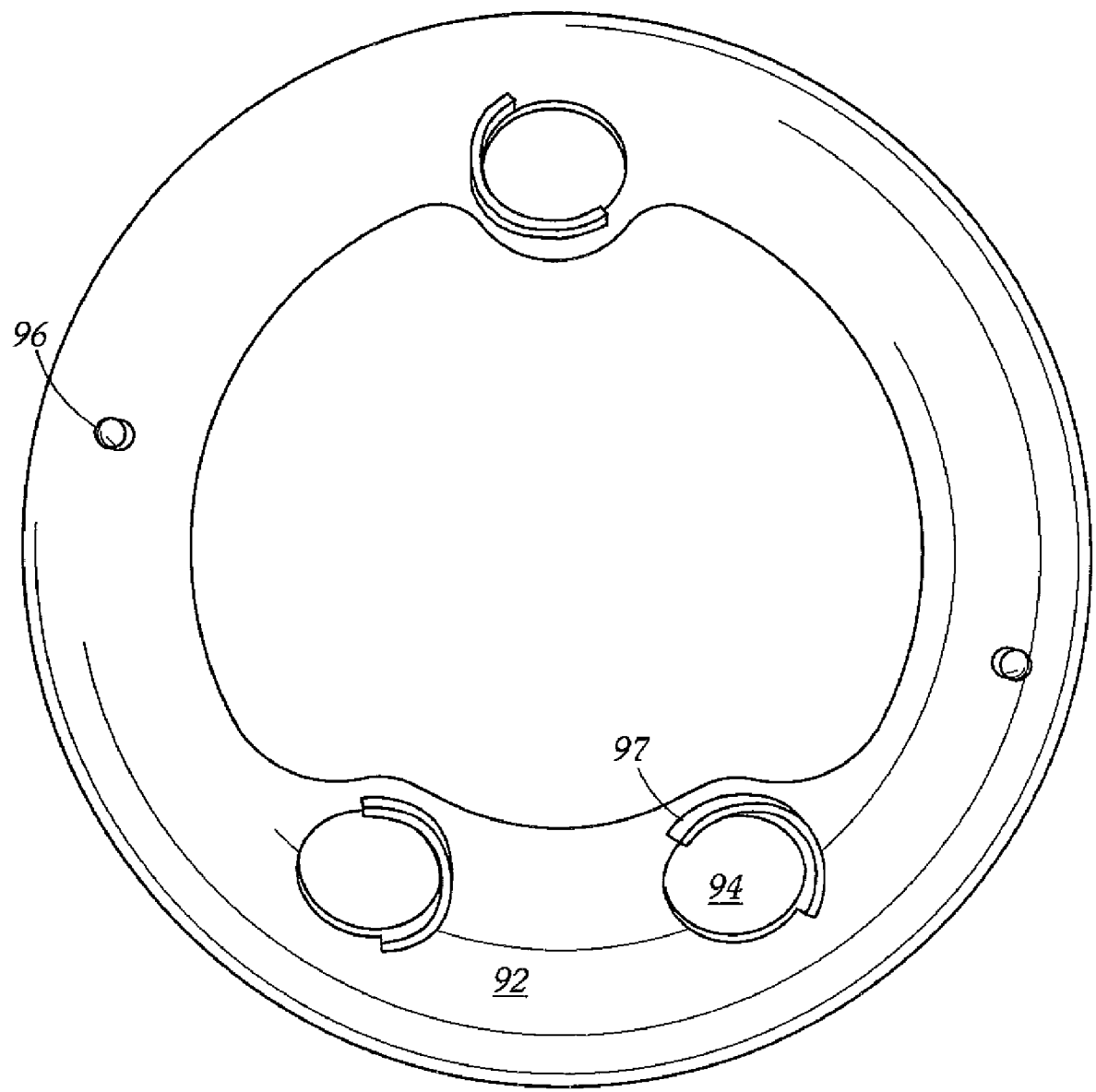
FIG. 30 is a plan view of a separation set loading device according to the present invention.
Figure 31:
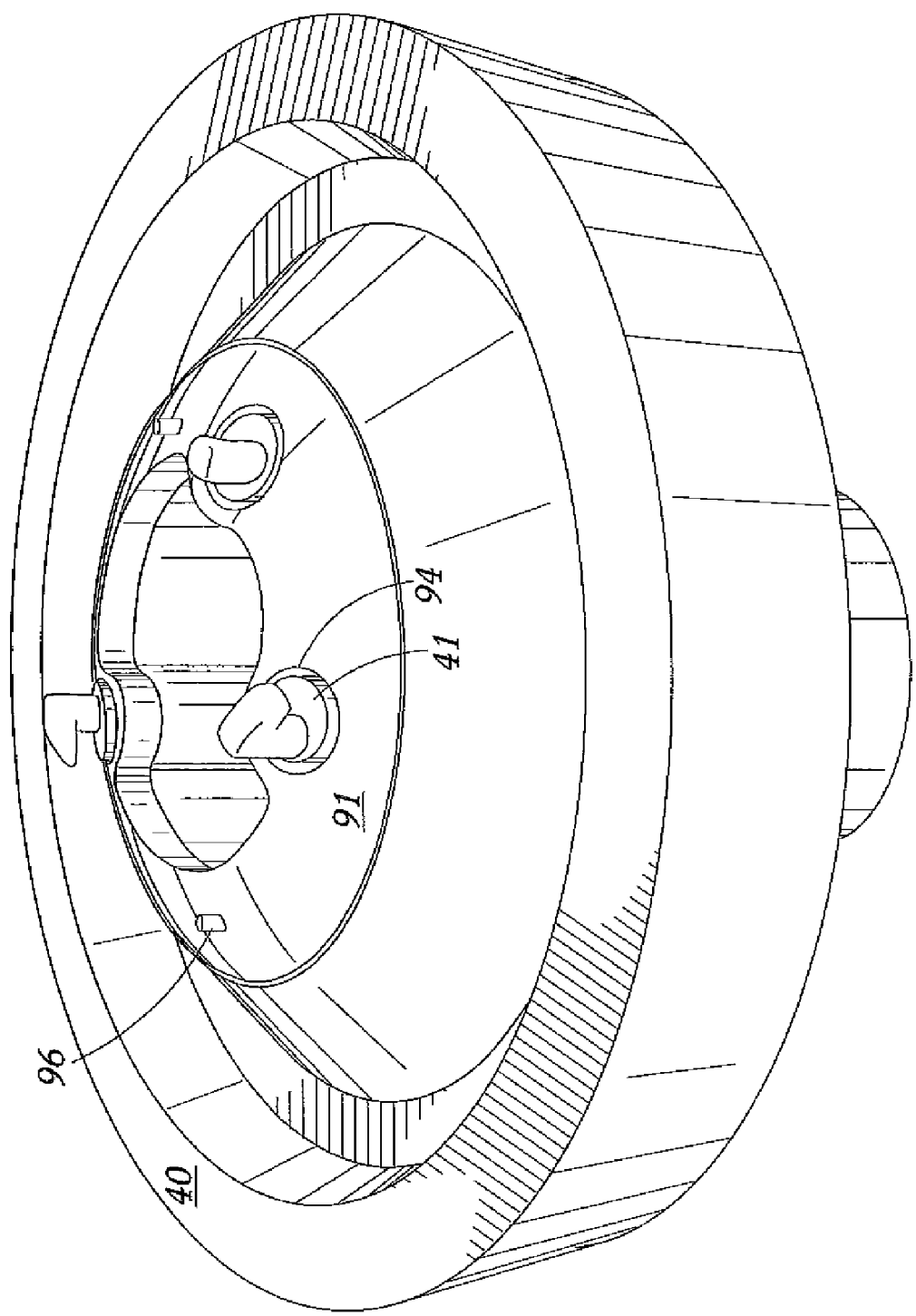
FIG. 31 is an isometric view of a rotor with a loading device like that in FIG. 29.
Figure 32:
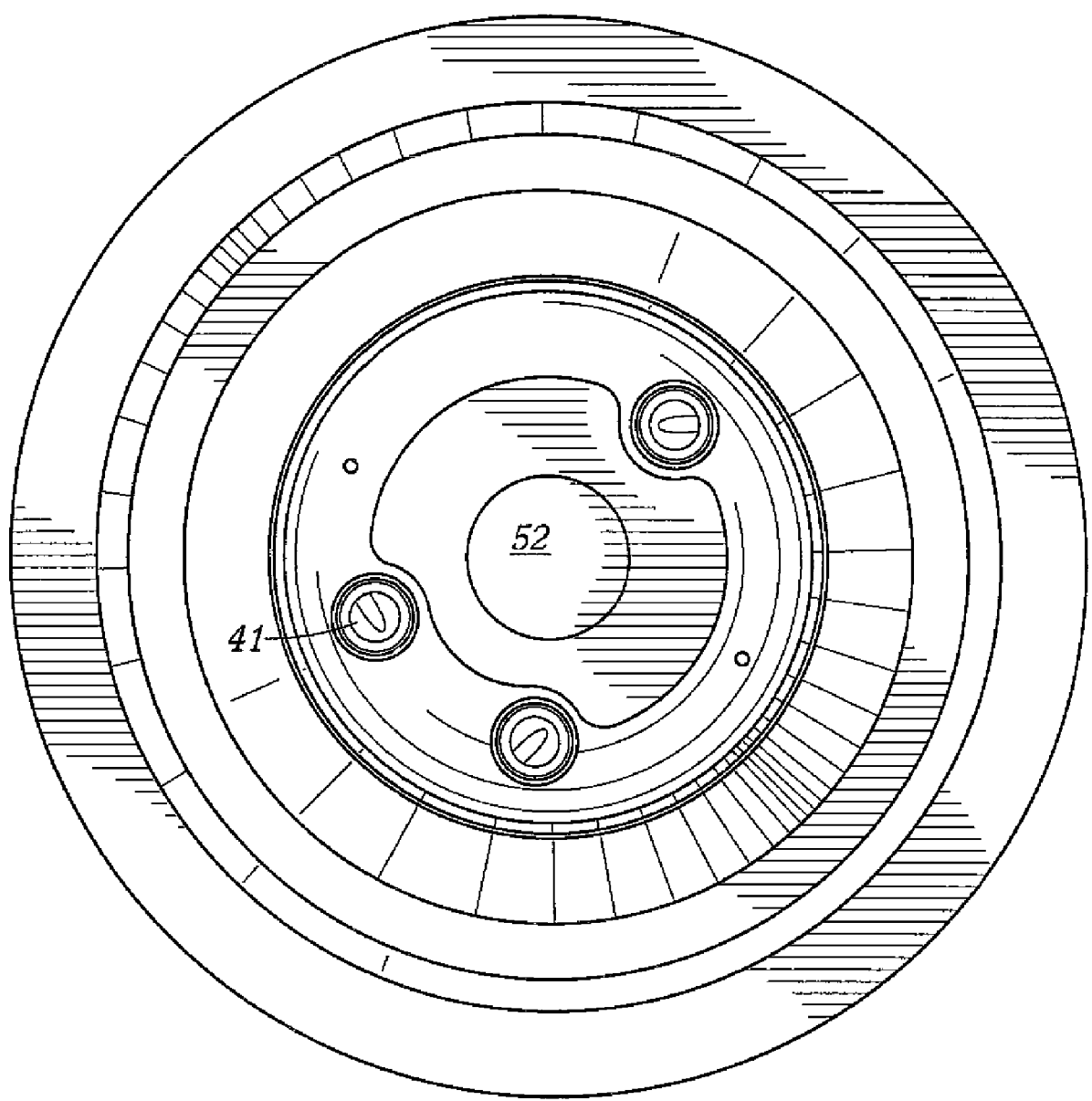
FIG. 32 is a plan view of a rotor and loading device like that in FIGS. 29 and 31.

FIGS. 24-32 show alternative structures that may be used in the process of loading the system/machine 18. In FIGS. 24 and 25, a loading device 80 (which may also be referred to as a "bucket" or a "cassette" or a "bayonet" or a "loading jig"; inter alia) includes a container portion 81 and a circumferential portion 82. The container portion 81 is adapted to receive one or more storage containers (e.g., containers 12, 14 and/or 24) of set 10 as shown in FIG. 26, through an open upper end 83. The lip portion 82 may include one or more apertures 84 which are adapted to fit over and receive inserted therein the support members 41 of rotor 40. The aperture 84 may also have associated therewith, one or more grooves 85 which may be adapted to receive respective tubes 13, 15 and/or 25 therein, particularly to assist in loading the tubes 13, 15 and/or 25 in respective clamps 42 of rotor support members 41 of rotor 40. See, for example, the loading process of FIGS. 16A, 16B and 16C (described above) which demonstrates a sort of resilient movement of the tube outward (FIG. 16B) upon continued downward movement (from the position starting in FIG. 16A) until the tube reaches the valve 42 and resiles therein (FIG. 16C). Optimal ridges 87 may assist here. Two further optional prongs 86 are shown which may be used to assist in holding a container 11 on the loading device 80 as shown in FIGS. 26 and 27. The loaded loading device 80 may then be inserted into the cavity 52 of rotor 40 and thereby place the set 10 in operative position relative to rotor 40 as shown, for example, in the previously described FIGS. 8, 9 and 10.

Alternatives to the loading device 80 may include devices such as rings 91 or 92 as shown in FIGS. 28-32. These devices 91, 92 may form a sort of lip area 93 not unlike that presented by the cassette 80, and thus simulate the lip area 82 of cassette 80 without the bucket or container portion 81. Respective holes 94 in devices 91, 92 are not unlike the apertures 84 of bucket/cassette 80 and provide the same features of receiving the support members 41 (see e.g., FIGS. 31 and 32). Prongs 96 are here also provided and again are not unlike those prongs 86 of bucket 80, to thus receive and hold a container 11 (not shown, in FIGS. 28-32), thereon. A distinction of device 92 over 91 is in the ridges 97 surrounding the holes 94, which may thereby provide additional support to the tubing lines 13, 15 and/or 25 (not shown) that may be disposed in operation (not shown) adjacent thereto.

In the above-described set of bags (FIG. 2, 3, 5), at least one the collection bag 16 may contain a storage solution, which must be prevented to flow into the separation bag 11 at any time. On the other hand, a volume of composite fluid (WB) that is to be separated, may transferred into the separation bag 11 before the set of bags is loaded on the turntable 40 of separation machine, with the valves 41 of the machine clamping the lines 13, 15, 25 connecting the various collection bags 12, 14, 24 to the separation bag 11. Unless the lines 13, 15, 25 are pinched by clamps before this transfer there is therefore a risk than part of the composite fluid flows into the collection bags 12, 14, 24.

This problem can be solved by providing the set of bags with frangible seals or reversible weak seals, properly located at the level of the collection bags 12, 14, 24 and at the level of the separation bag 11. For example, when the supply line 19 for transferring a volume of composite fluid into the annular chamber 11a of the separation bag 11 of FIG. 5 is directly connected to the annular chamber 11a, the opening 30a connecting the distribution channel 45 to the annular chamber 11a may be reversibly sealed by the weak seal so as to prevent any flow of the composite fluid into the collection bags 12, 14, 24 upon filling the separation bag 11 with a volume of composite fluid. When the supply line 19 for transferring a volume of composite fluid into the annular chamber 11a of the separation bag 11 of FIG. 5 is connected to the distribution channel 45 (as is the case in FIG. 5), such reversible weak seals may be formed within the distribution channel 45, so as to isolate the collection bags 12, 14, 24 from the area of the distribution channel where the line 19 opens.

In more details, if integrated solutions (e.g. anticoagulants and/or storage solutions for RBCs and/or platelets) are desired to be incorporated and made parts of pre-packaged sets 10 (or the like), it appears that, all whole blood bag sets that contain liquids (and hence have to be steam sterilized) will more often preferably contain frangible connectors or some other separation means to contain the liquids/solutions in certain parts of the sets 10 and not allowed to thereby reach undesirably into other parts. Nevertheless, frangible connectors are difficult in implementation because of the following concerns, inter alia: potential breakage in production, sterilization, transport, centrifugation and/or use; risk of piercing outer tubing or bag, hence creating leakage and contamination risk; repetitive strain injury; not generally automatable;

cost; potential for hemolysis due to incomplete opening, and/or the presentation of sharp edges in/adjacent an RBC chamber/container or flow path.

However, the pressure obtained in a normal blood bag centrifuge at 4-5000 rpm can come up to 50 bar, and no means have yet been introduced which can stand these high pressures in a conventional cup-type of centrifuge, apart from frangibles.

Nevertheless, in the present invention, whole blood system, a different situation may be presented. Pressures at the outer radius/outer circumference 38 at 3200 rpm may be below 17 bar. More importantly, the connections where frangibles (between round bag and RBC bag and between round bag and plasma bag) may be used can all be located in or adjacent the center cavity area 11c, where pressures are always much lower. Secondly, all the lines where a frangible may be needed also pass through a (closed) valve during initial centrifugation. Thirdly, a controlled pressure (from the hydraulic system) may be applied on the system (up to 2 bar for example). Fourth, pressure profiles can be monitored. These considerations might open alternative possibilities for pressure-activated closure devices or frangibles. However, as an additional issue, steam sterilization, if used, often involves working pressures up to 4 bar, and thus this might present a further issue with straightforward fixed-pressure release valves.

Hence, the present invention may include alternative embodiments in which a weak seal, such as an incomplete RF (radio frequency) weld, is created on a tubing or a bag flow channel (e.g. flow channel 45). Such a weld may be in the form of providing the initial adhesion of the tubing or channel walls together, but not completely welded so that the adhered portions may be later separated from each other without compromising the integrity of the tubing or flow channel. Such a weld may be made with conventional RF welding apparatuses. Or, in another embodiment, a standard mechanical clamp or some more customized compression device (neither shown) may be put on the tubing (e.g., tubing line 15 and/or tubing line 25 to bag(s) 14 and/or 24 which might contain pre-packaged integrated fluid solutions as introduced above) pinching the tubing closed before steam sterilization. Note, such a conventional clamp may be what is commonly known as a TLC type, inter alia. Then, during sterilization, this clamping/pinching might result in or provide a soft weld at that point in the tubing line. In one embodiment, the standard clamping may be combined with a device designed to compress the tubing soft weld in a direction perpendicular to (or 90 degrees) the original clamping direction of the standard clamp. After sterilization, the clamps may typically be removed, and a closed tubing will result that cannot be opened with slight pressure (tested on steam sterilized prototypes). Rolling the weld between an operator's fingers or putting pressure on the soft weld perpendicular thereto can result in opening of the soft weld and hence opening of the fluid pathway.

These steam-sterilization-induced soft welds could either be relatively sharp welds of approximately 1 mm large in conventional blood tubing set dimensions such as induced by typical blood tubing set clamps currently used on/in such conventional blood tubing and bag sets, or could be broader, 5-10 mm large welds. Such larger models may be used to generate clamping pressures lower than those obtained by the more conventional clamps. An example clamp may be a sliding block with a groove smaller than twice the tubing wall thickness, which provides for sliding the block over the tubing to pinch the tubing closed.

Application of a set 10 having any such soft weld (RF or steam induced or otherwise) formed therein could be as follows: First, remove the clamps if used (not shown) (either in manufacture or at the situs of use. Then, load the round bag and satellite storage bag system 10 into the rotor 40 of the machine/system 18. Note, the soft welds here will be disposed between the valves 42 and the round bag 11. Next, close the rotor lid 55 and have the system/machine 18 close the valves 42 (e.g. using the control system 60). Then, pressurize the round bag using the hydraulic system (or otherwise) (also e.g., using the control system 60). Then, as a result, the soft welds (which may also be referred to as frangibles herein) between the round bag 11 and each valve 42 will be pressurized and thereby be broken into open position. The pressure build-up and sudden drop, when air/liquid comes into the piece of tubing between the soft weld/frangible and each valve, can be monitored to positively confirm opening of frangible. Note, the focus in such a process has mainly been on the connections between the round bag 11 and the storage bags (e.g., 14 and/or 24), as other challenges with a closure mechanism/frangible between the round bag 11 and a collect bag 20 with a possible filter 70 might be distinct, and these may not have the same control on pressure applied, e.g., from the system through the filter 70.

The advantages of such a system could be that the system might then be inexpensive; automated, thus involving no or very limited operator time, noting also that with automation there will also be no or very controlled possibility to forget or override. This system could also eliminate/relieve repetitive strain injury and present no or again extremely limited risk for hemolysis.

It may, in some embodiments of the clamp/steam induced soft weld, be a good idea to leave the conventional clamp in place until the set is to be loaded into the rotor 40. This would assure that, if the set should experience high temperature during shipment or storage, the seal would remain intact. Also, since the operator must remember to remove the clamp prior to loading into rotor 40, it should be designed so that it is impossible (or at least highly unlikely) that the set could be loaded with the clamp still in place.

A fear of the seal opening due to high temperature suggested a test whereby the tubes were boiled for 15 minutes (submerged in the water), and the seals were totally unaffected. It seems a certain temperature between 100 and 120 C would have to be exceeded in order to heat-open the soft weld. A clamp/spacer could be used in some way in the rolled up round bag (as for example, in a cone configuration) that clamps the different tubing needed, and which would be removed in one movement when loading the loading device (bucket or cassette) 80/90. In such a case (clamp weld survives 100 C) the tubing can be clamped with fixturing at the steam sterilizer (i.e., steam sterilizer tray) that would be removed when the product is removed from the sterilizer for packaging.

There may be a way to automate this frangible concept further. A simple "frangible opening device" which is no more than a local heater around the frangible could be used. This frangible could either be the kind of steam induced as described or a soft seal.

Another test of steam-induced weak seals involved application of 80 psi that did not break them. These were then left 5 minutes at 120 C (dry heat, without any pressure), resulting in those seals opening up all by themselves. A technical implementation could be in having a steam-induced seal (or a soft seal) between the valve and storage bag, very close to the valve. Just where the tubing leaves the valve, there would be a small heat resistance. Once the valves are loaded and closed, a short heat pulse could be used to open the soft weld weak seals, and there would be ample time for the tubing to cool down prior to the first blood contact.

A still further alternative for heat opening a steam induced weld is to use the RF welder/sealer 42. Thus, the soft weld or soft seal could be placed into position with the soft weld/seal exactly between the RF sealer electrodes, and applying the high frequency without closing the valves or at least without pressurizing the tube. This may suggest coming closer to the PVC. With the current rotor turntable 40, this looks possible without risking that liquids move from the bag to the round bag or vice versa (in this embodiment, there would preferably be provided no possibility to close the valve while the frangible is being heat-opened). This embodiment would have the advantage that no extra space would be required in the rotor/disposable.

Further scope of applicability of the present invention will be apparent to the skilled artisan from the detailed description given hereinabove. However, it should be understood that the detailed description and specific examples, while indicating preferred embodiments of the invention, are given by way of illustration only, since various changes and modifications within the spirit and scope of the invention will become apparent to those skilled in the art from this detailed description.

The invention claim is:

1. A device for loading into the rotor of a centrifuge a set of bags for the separation of a composite fluid into at least two fluid components, the set of bags comprising a separation bag connected by a tube to at least one collection bag for a fluid component, the separation bag having an annular separation chamber delimited by an outer and an inner circumferences; and a support member connected to the inner circumference of the annular chamber and at least partially closing the space defined within the inner circumference of the annular chamber, the rotor comprising a turntable for supporting the separation bag; and a central compartment for containing at least one collection bag, the loading device comprising a loading container having an annular rim extending outwardly, the container being shaped so as to fit within the compartment of the rotor whereas the annular rim rests on the turntable of the rotor.

2. A device according to claim 1, wherein the rim of the loading container has an outer circumference that does not exceed the inner circumference of the separation chamber.

3. A device according to claim 1, wherein the rim of the loading container comprises at least two protruding elements for cooperating with two corresponding apertures of the support member of the separation bag so as to help position and secure the separation bag to the loading container.

4. A device according to claim 1, wherein the rim of the loading container comprises at least one aperture corresponding to at least a head of a valve member mounted on the rotor at the periphery of the central compartment of the rotor and protruding above the turntable of the rotor.

5. A device according to claim 4, wherein the valve head has a seat for receiving a portion of tube, and wherein a portion of the tube connecting the at least one collection bag to the separation bag is secured to the rim over the aperture so as to be pre-positioned with respect to a tube seat of a valve member.

* * * * *